(12) United States Patent
Dong et al.

(10) Patent No.: US 7,517,853 B2
(45) Date of Patent: Apr. 14, 2009

(54) SOMATOSTATIN-DOPAMINE CHIMERIC ANALOGS

(75) Inventors: Zheng Xin Dong, Holliston, MA (US); Michael DeWitt Culler, Hopkinton, MA (US); Yeelena Shen, Franklin, MA (US)

(73) Assignee: Ipsen Pharma S.A.S., Paris (FR)

( * ) Notice: Subject to any disclaimer, the term of this patent is extended or adjusted under 35 U.S.C. 154(b) by 391 days.

(21) Appl. No.: 10/553,014

(22) PCT Filed: Apr. 8, 2004

(86) PCT No.: PCT/US2004/010891

§ 371 (c)(1), (2), (4) Date: Oct. 11, 2005

(87) PCT Pub. No.: WO2004/091490

PCT Pub. Date: Oct. 28, 2004

(65) Prior Publication Data

US 2006/0258572 A1 Nov. 16, 2006

Related U.S. Application Data

(60) Provisional application No. 60/462,374, filed on Apr. 11, 2003.

(51) Int. Cl.
*A61K 38/12* (2006.01)

(52) U.S. Cl. .................................... 514/11

(58) Field of Classification Search ............... None
See application file for complete search history.

(56) References Cited

FOREIGN PATENT DOCUMENTS

WO 02/100888 12/2002

OTHER PUBLICATIONS

Jenkinson, D. H. et al., "International Union of Pharmacology Committee on Receptor Nomenclature and Drug Classification. IX. Recommendations on Terms and Symbols in Quantitative Pharmacology," Pharmacol. Rev., 1995, 47(2):255-266.
Basu, S. et al., "The neurotransmitter dopamine inhibits angiogenesis induced by vascular permeability factor/vascular endothelial growth factor," Nature Medicine, 2001, 7:569-574.
Reubi, J.C. et al., "Distribution of somatostatin receptors in normal and neoplastic human tissues: Recent advances and potential relevance," Yale J. Biol. and Med., 1997, 70:471-479.
Saveanu, A. et al., "Demonstration of enhanced potency of a chimeric somatostatin-dopamine molecule, BIM-23A387, in suppressing growth hormone and prolactin secretion from human pituitary somatotroph adenoma cells," J. Clin. Endo. & Metab., 2002, 87:5545-5552.
Tangbanleukal, L. et al., "Prolactin mediates estradiol-induced inflammation in the lateral prostate of Wistar rats," Endocrinology, 1993, 132:2407-2416.

*Primary Examiner*—Andrew D Kosar
(74) *Attorney, Agent, or Firm*—Yankwich & Associates; Alan F. Feeney; Tony K. Uhm

(57) ABSTRACT

The invention features somatostatin-dopamine chimeric analogs and methods relating to their therapeutic use for the treatment of neoplasia, acromegaly, and other conditions.

2 Claims, 17 Drawing Sheets

Figure 2:
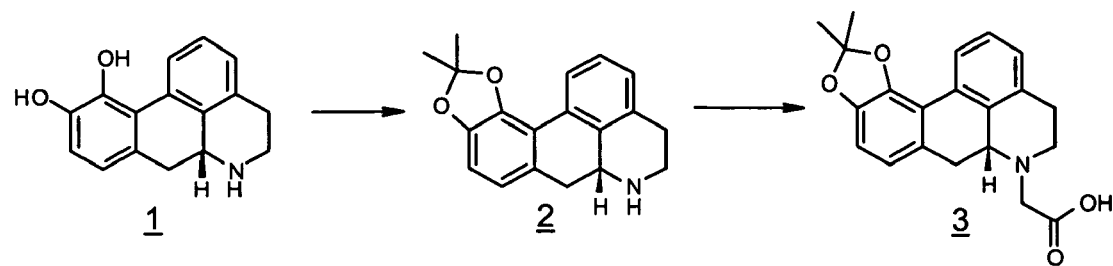

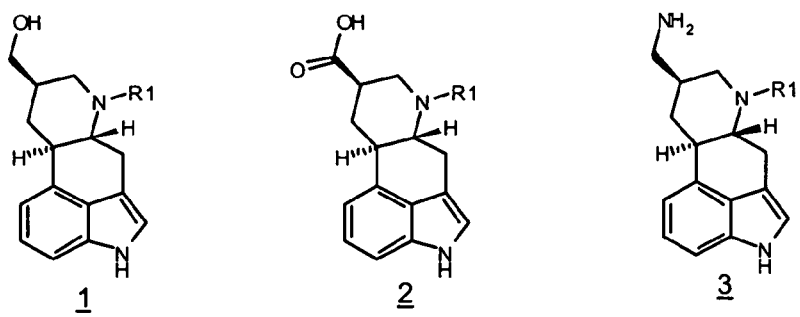
Scheme 1
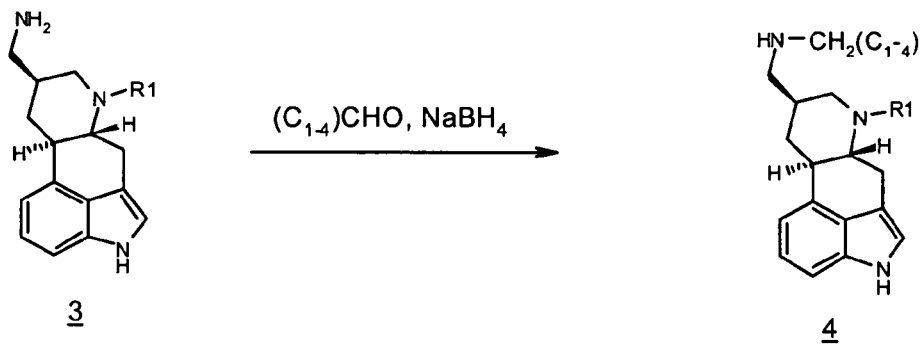
Scheme 2
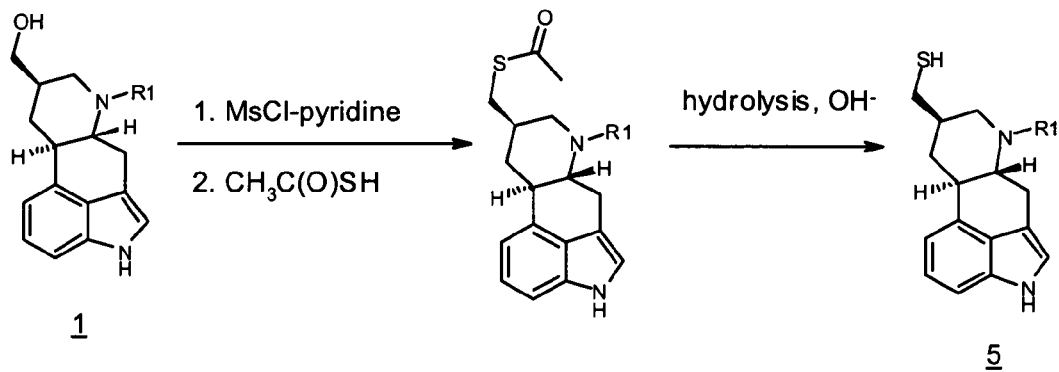
FIG. 1-A

Scheme 3:
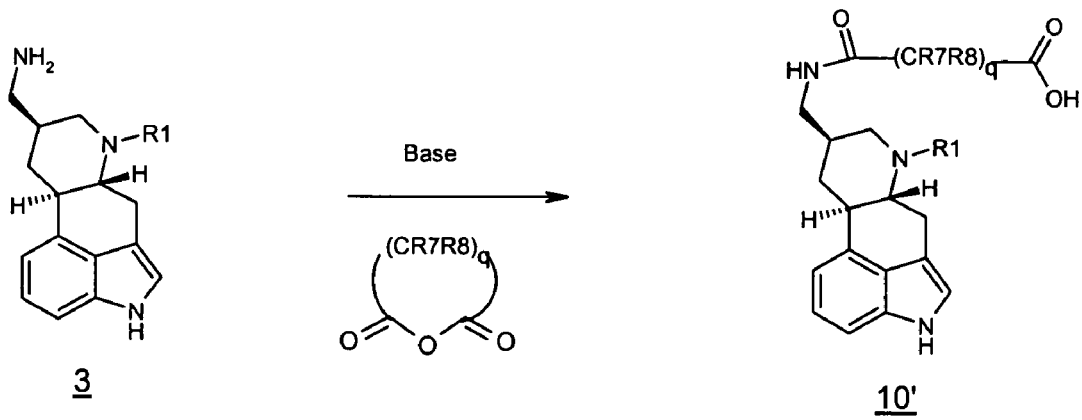
Scheme 4:
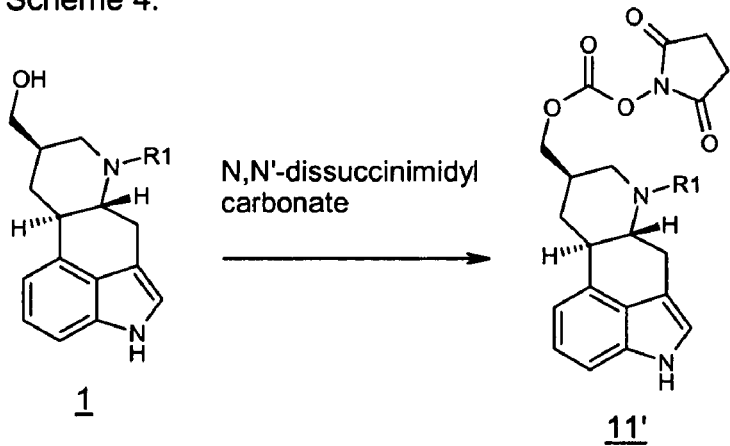
Scheme 5:
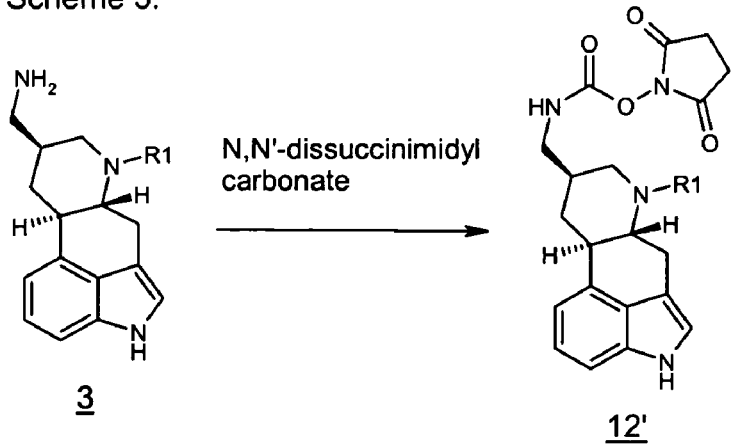
*FIG. 1-B*

Scheme 6:
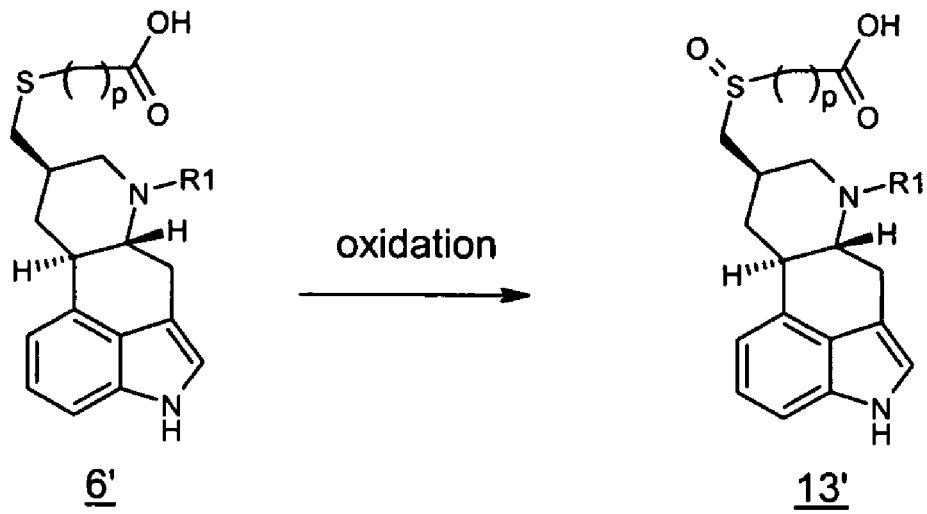
Scheme 7:
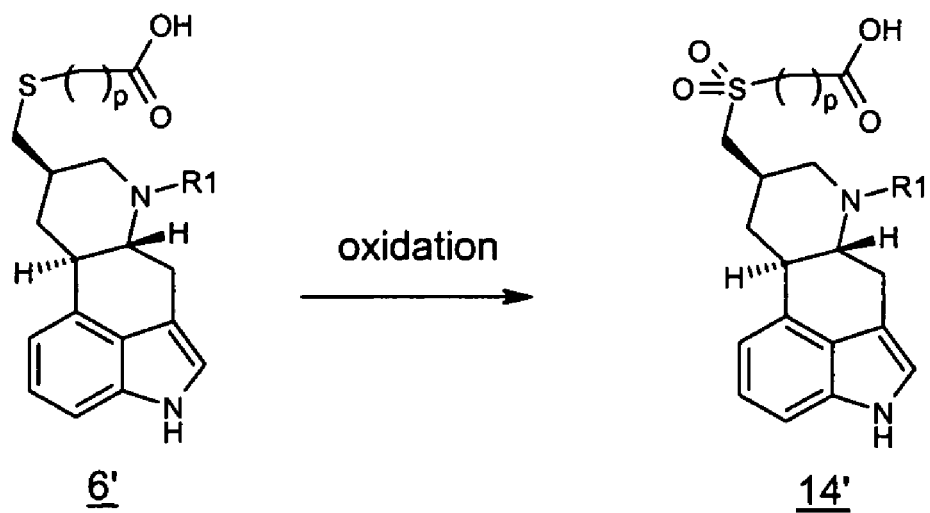
FIG. 1-C

Scheme 8:
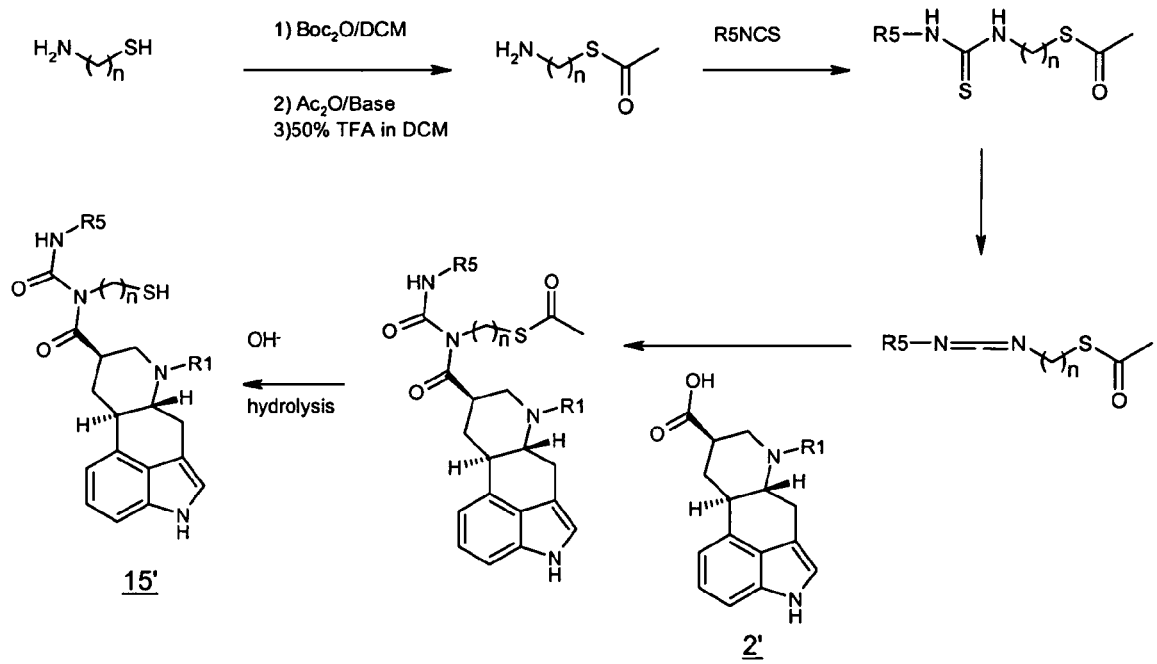
Scheme 9:
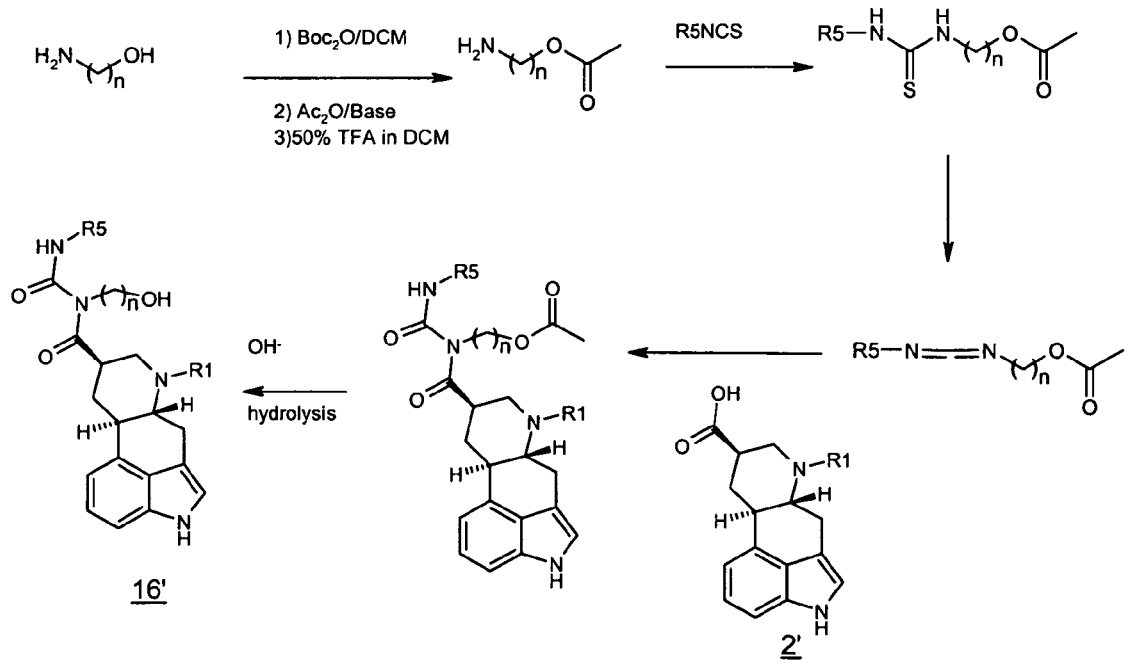
FIG. 1-D

Scheme 10:
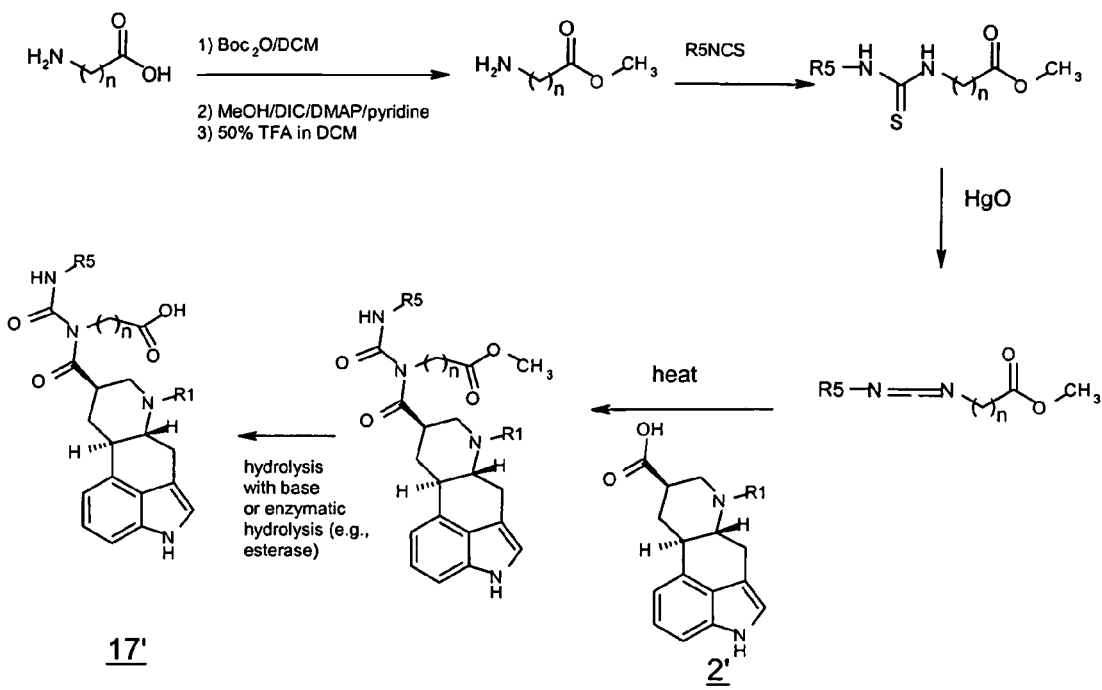
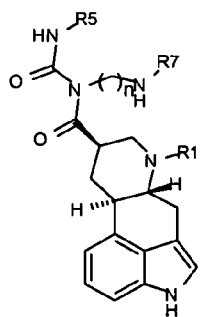
18' (see Scheme II)
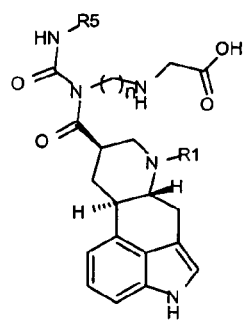
19' (see Scheme II)
*FIG. 1-E*

Scheme 11:
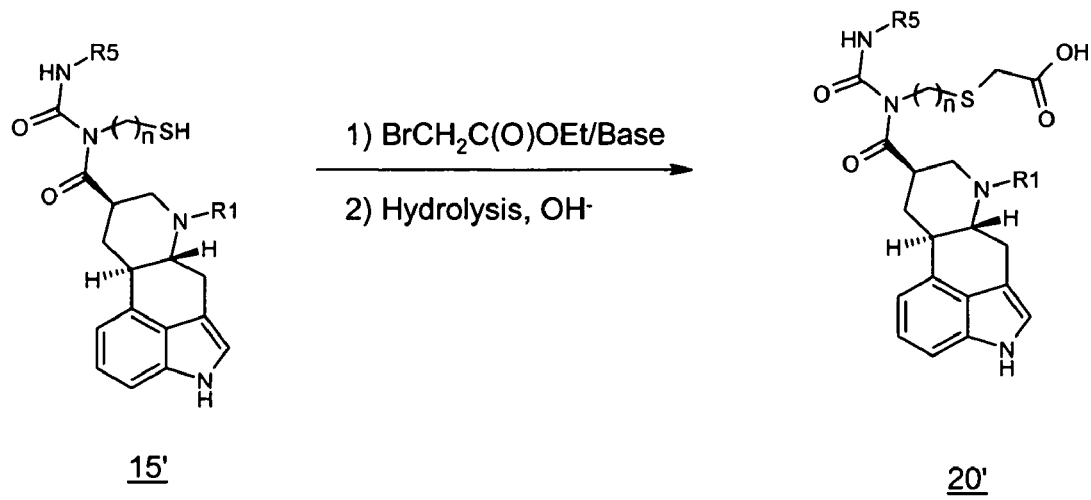
Scheme 12:
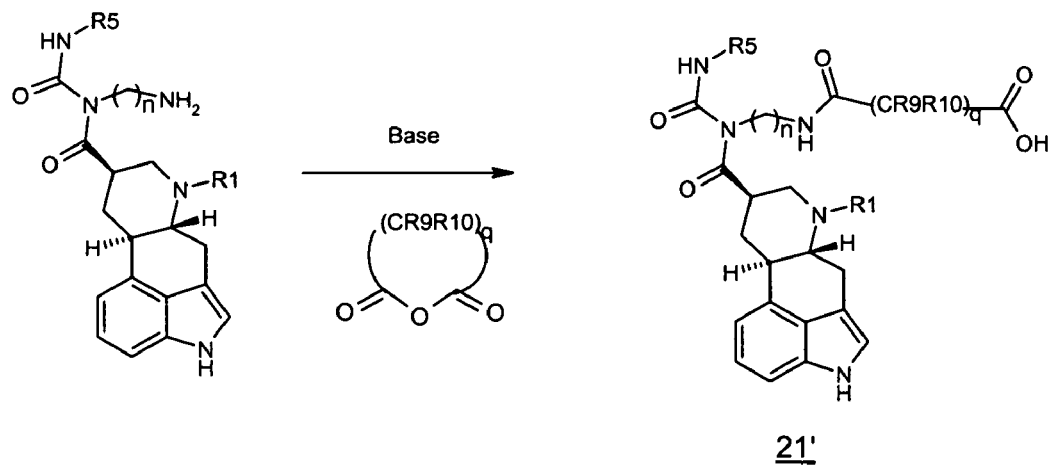
*FIG. 1-F*

Scheme 13:
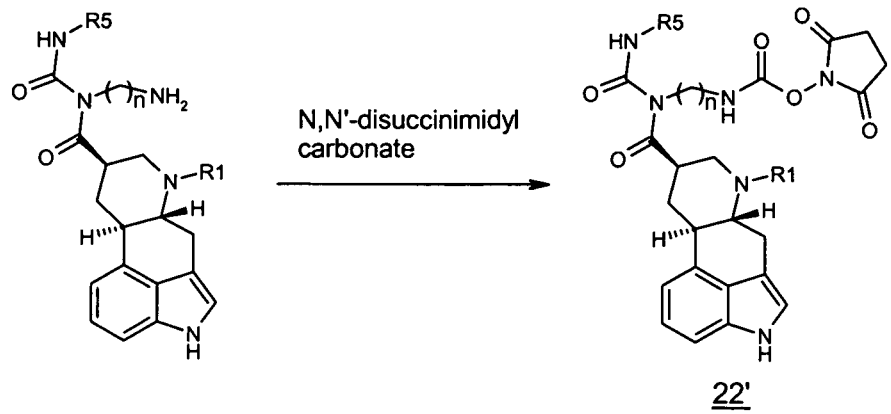
Scheme 14:
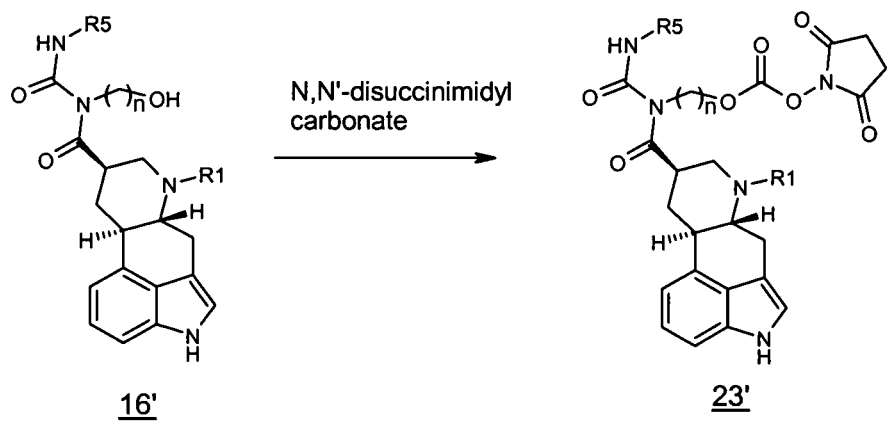
Scheme 15:
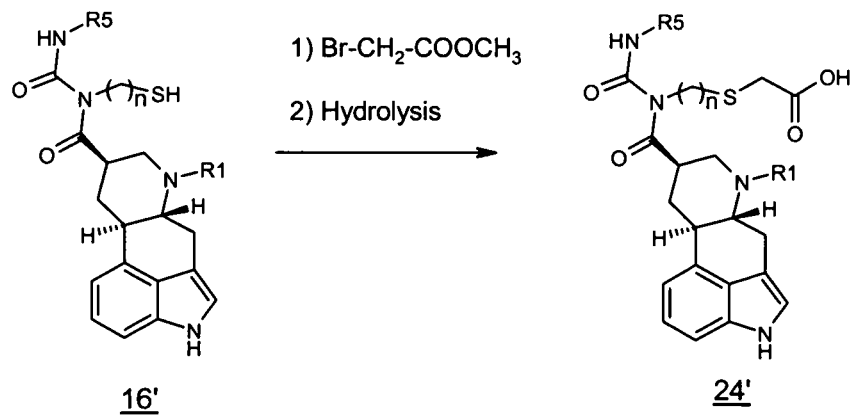
*FIG. 1-G*

Scheme I
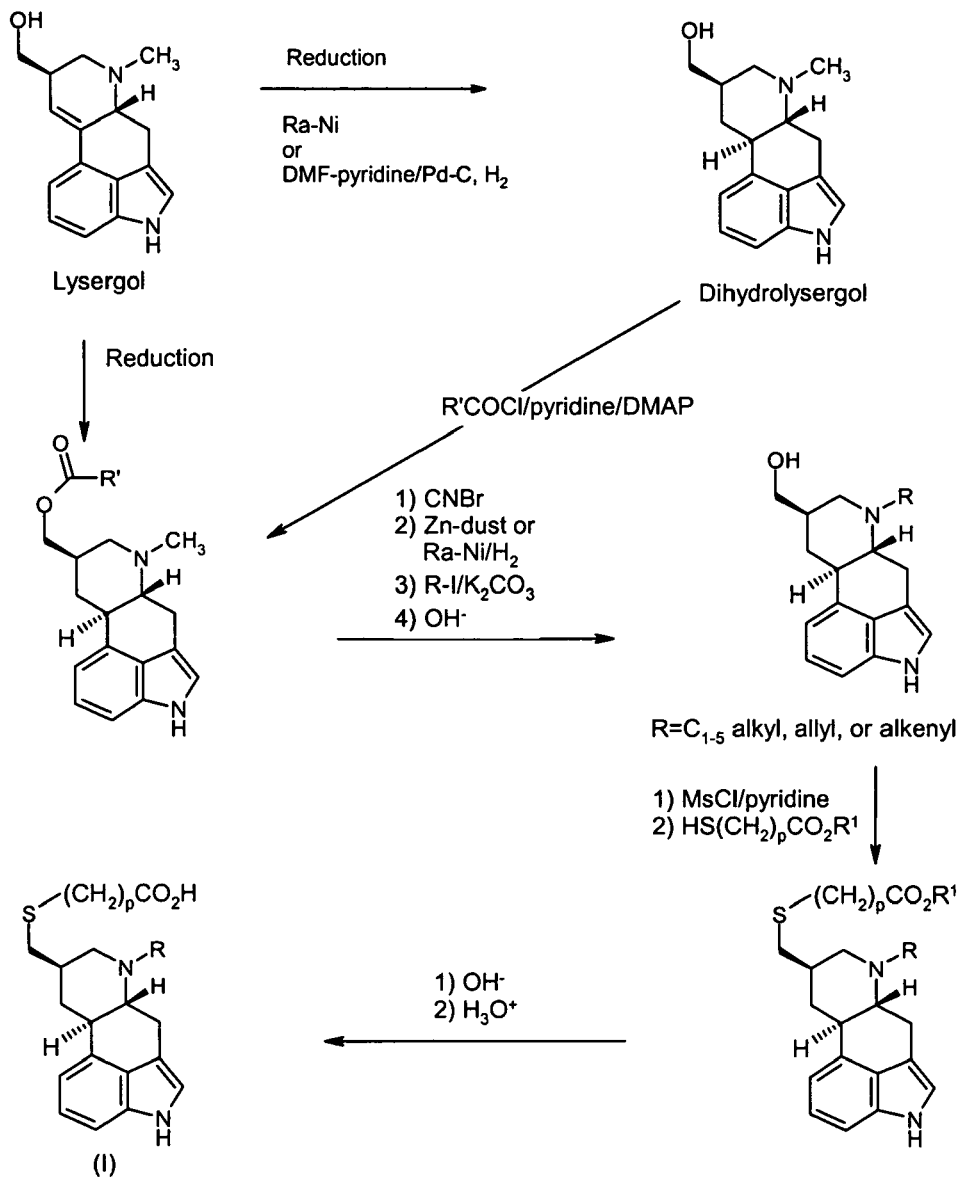
Compounds 6', 7', and 8' can be synthesized using the synthetic scheme above:
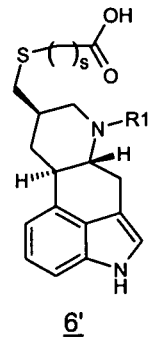
6'
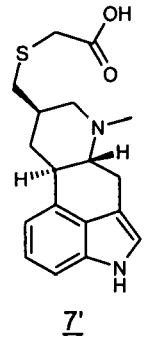
7'
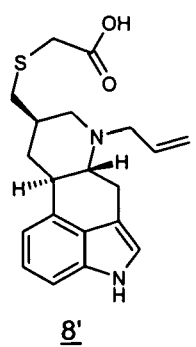
8'
*FIG. 1-H*

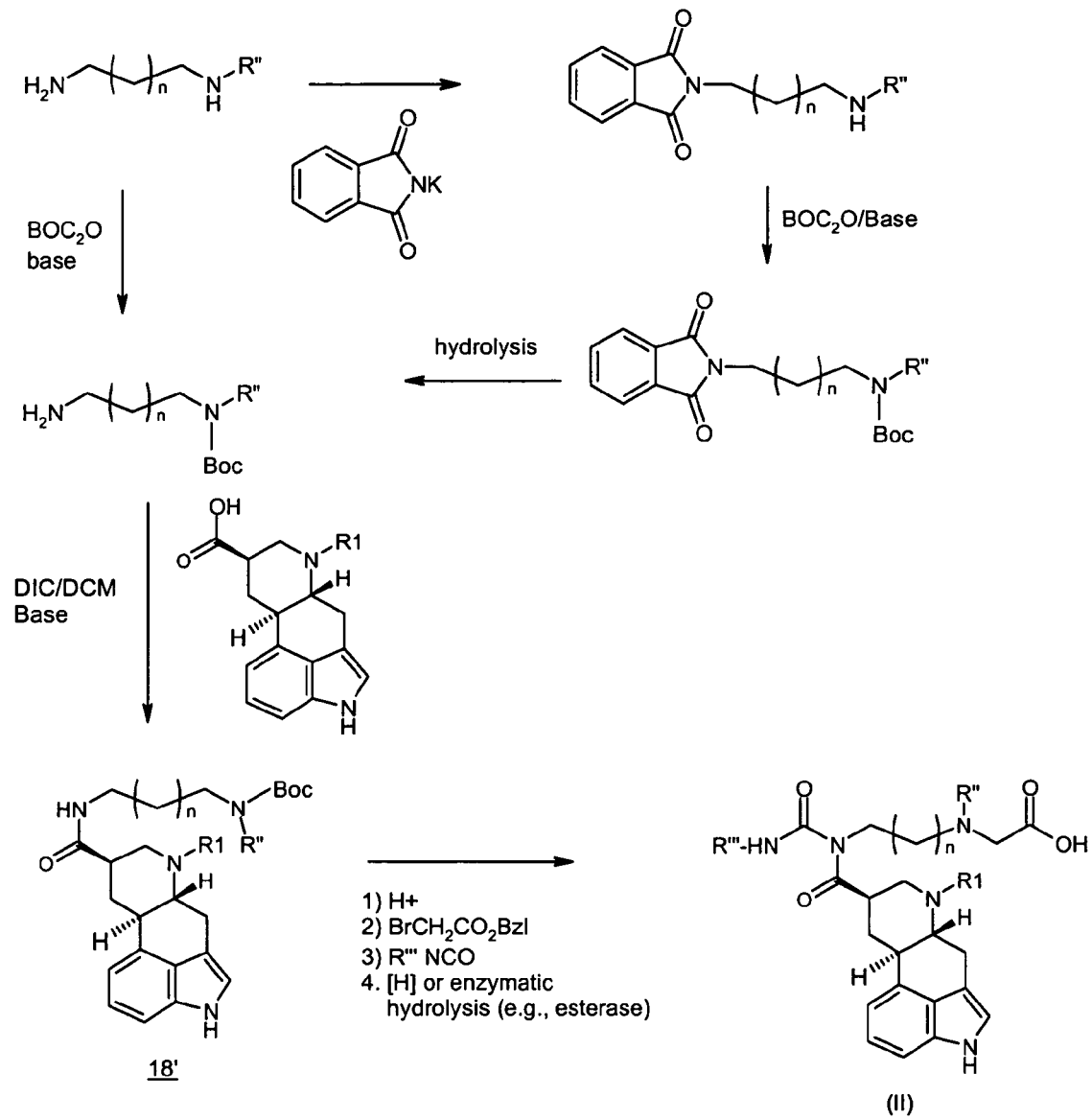
FIG. 1-I

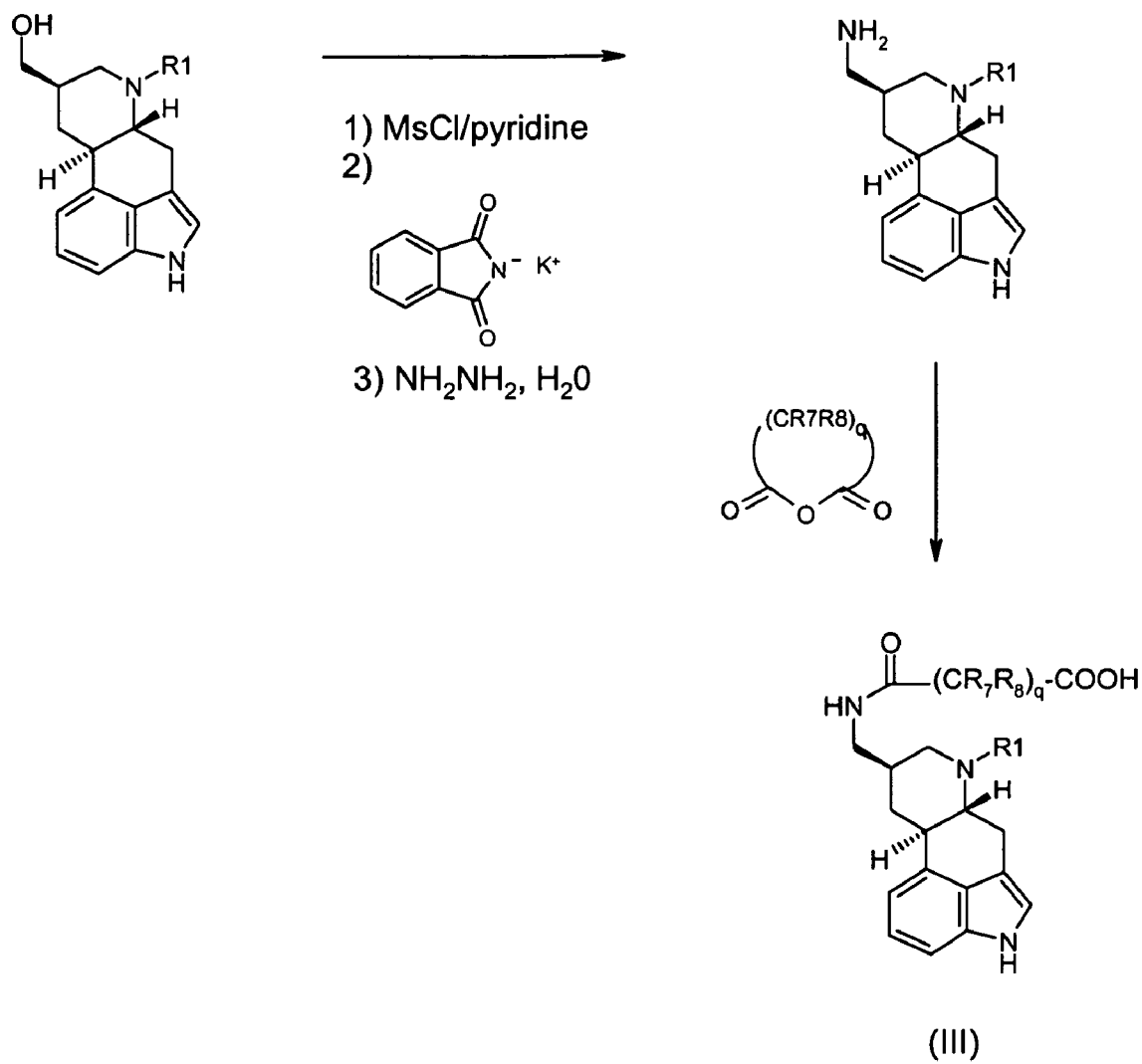
FIG. 1-J

Scheme IV:
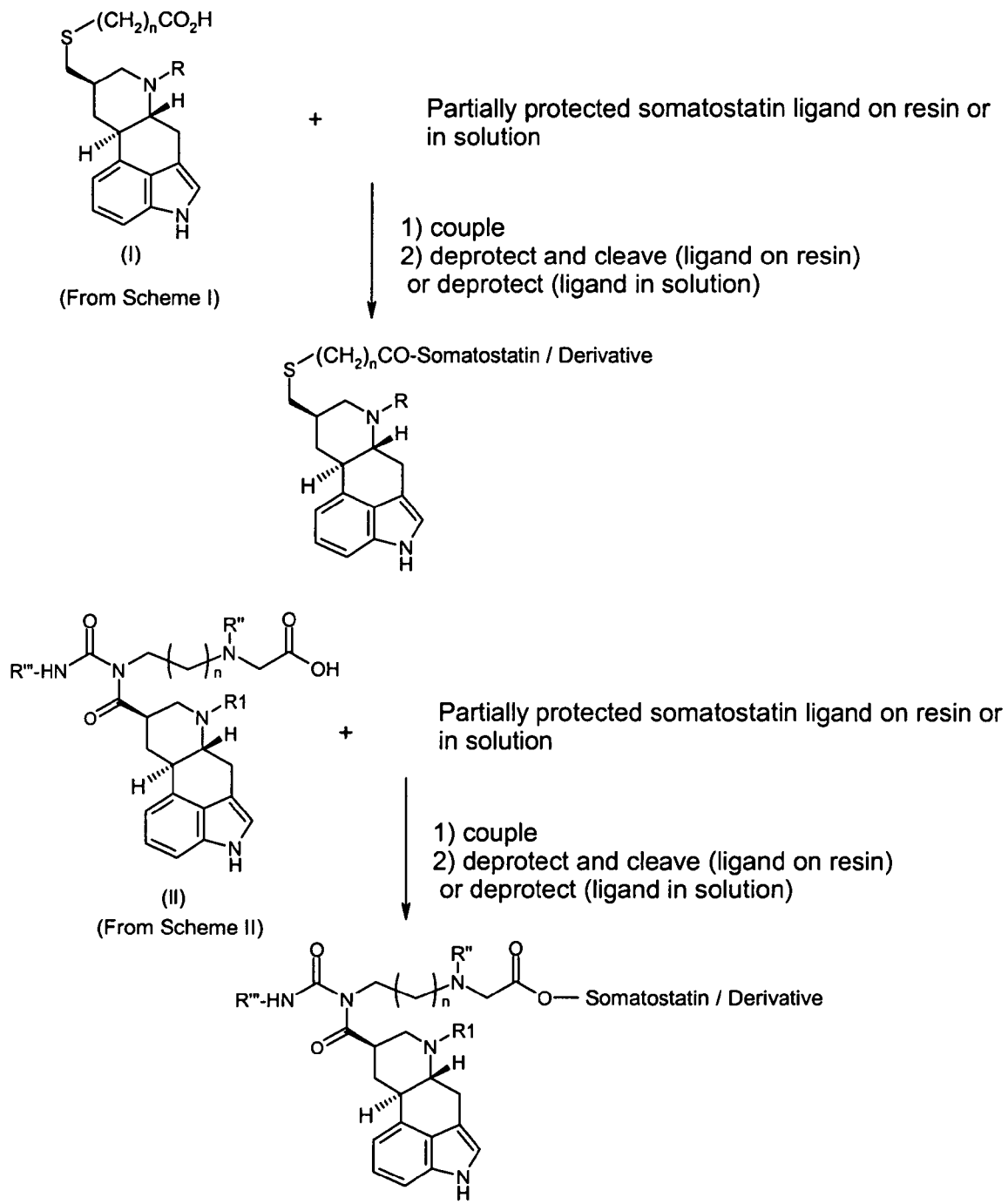
*FIG. 1-K*

Scheme V:
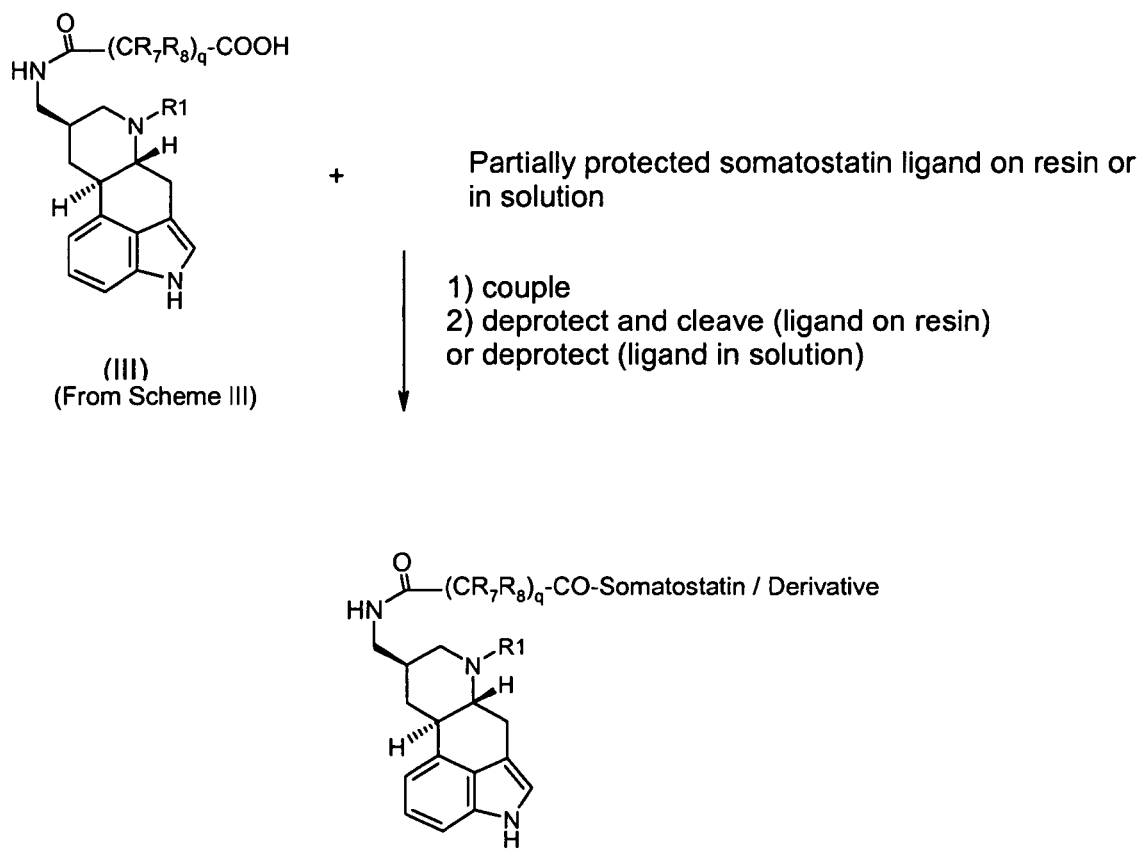
*FIG. 1-L*

Scheme VI:
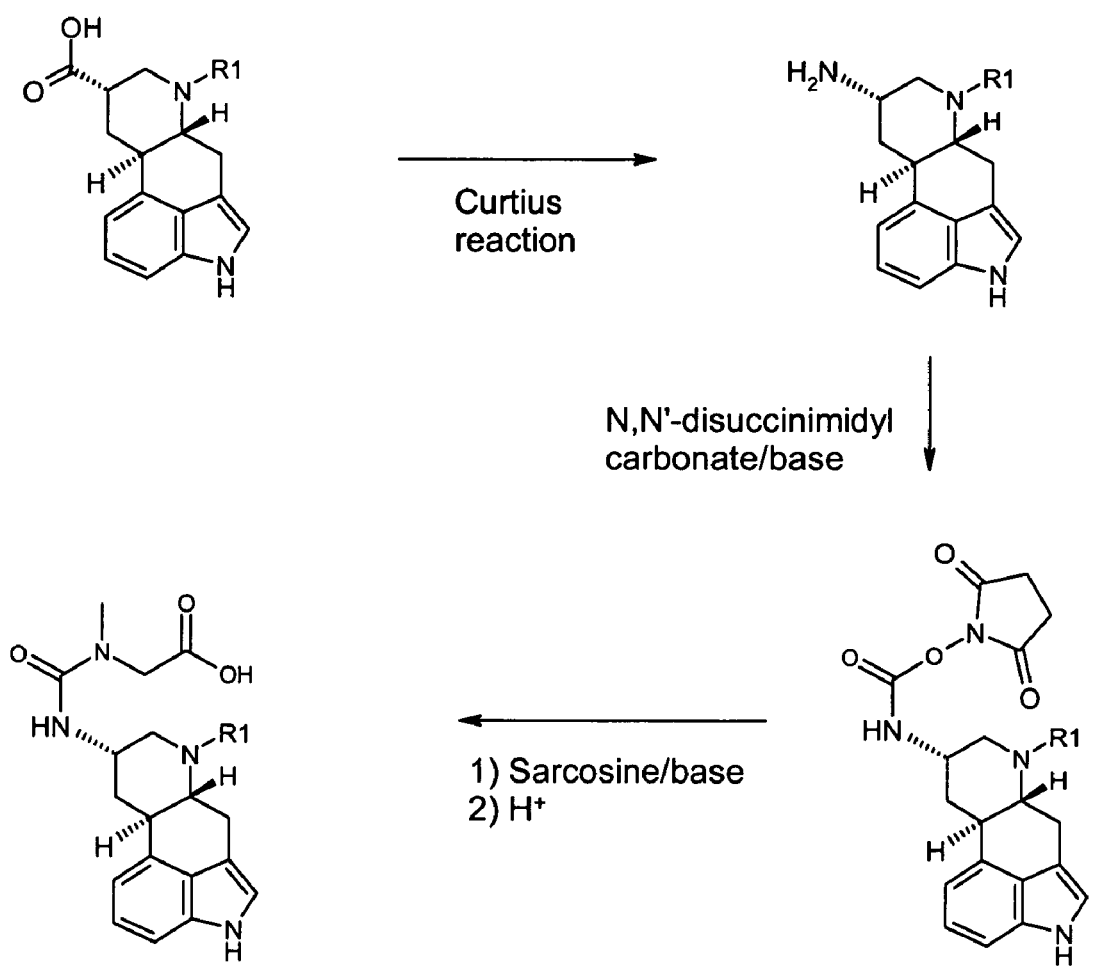
FIG. 1-M

SOMATOSTATIN-DOPAMINE CHIMERIC ANALOGS

This application is a United States national stage filing under 35 U.S.C. §371 of international (PCT) application No. PCT/US2004/10891, Apr. 8, 2004, and designating the US, which claims priority to U.S. provisional application 60/462,374 filed Apr. 11, 2003.

BACKGROUND OF THE INVENTION

The present invention is drawn to somatostatin-dopamine chimeric analogs and methods relating to their therapeutic use.

Dopamine is a catecholamine neurotransmitter that has been implicated in the pathogenesis of both Parkinson disease and schizophrenia. Dopamine and related molecules have been shown to inhibit the growth of several types of malignant tumors in mice, and this activity has been variously attributed to inhibition of tumor-cell proliferation, stimulation of tumor immunity or as well as effects on melanin metabolism in malignant melanomas. Recent studies demonstrated the presence of D2 dopamine receptors on endothelial cells. Dopamine has recently been reported to strongly and selectively inhibit at non-toxic levels the vascular permeabilizing and angiogenic activities of VPF/VEGF.

Somatostatin (SS), a tetradecapeptide has been shown to have potent inhibitory effects on various secretory processes in tissues such as pituitary, pancreas and gastrointestinal tract. SS also acts as a neuromodulator in the central nervous system. These biological effects of SS, all inhibitory in nature, are elicited through a series of G protein coupled receptors, of which five different subtypes have been characterized (SSTR-1-SSTR-5). These five subtypes have similar affinities for endogenous SS ligands, but have differing distributions in various tissues. Somatostatin binds to the five distinct receptor (SSTR) subtypes with relatively high and equal affinity for each subtype.

There is evidence that SS regulates cell proliferation by arresting cell growth via SSTR-1, -2, -3, -4, and -5 subtypes, and/or by inducing apoptosis via SSTR-3 subtype. SS and various analogues have been shown to inhibit normal and neoplastic cell proliferation in vitro and in vivo via specific SS receptors (SSTR's) and possibly different postreceptor actions. In addition, there is evidence that distinct SSTR subtypes are expressed in normal and neoplastic human tissues, conferring different tissue affinities for various SS analogues and variable clinical response to their therapeutic effects.

Binding to different types of somatostatin receptor subtypes is associated with the treatment of various conditions and/or diseases. For example, the inhibition of growth hormone has been attributed to the somatostatin type-2 receptor ("SSTR-2"), while the inhibition of insulin has been attributed to the somatostatin type-5 receptor ("SSTR-5"). Activation of types 2 and 5 have been associated with growth hormone suppression and more particularly growth hormone secreting adenomas (acromegaly) and thyroid stimulating hormone (TSH) secreting adenomas. Activation of type 5 but not type 2 receptor has been associated with treating prolactin secreting adenomas. Other indications associated with activation of the somatostatin receptor subtypes include inhibition of insulin and/or glucagon for treating diabetes mellitus, angiopathy, proliferative retinopathy, dawn phenomenon, and nephropathy; inhibition of gastric acid secretion for treating peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis; treatment of inflammatory disorders such as arthritis; retinopathy; chronic allograft rejection; angioplasty; preventing graft vessel and gastrointestinal bleeding. Preferably, a somatostatin analog is selective for the specific somatostatin receptor subtype or subtypes responsible for the desired biological response to reducing interaction with other receptor subtypes which could lead to undesirable side effects or loss of efficacy.

Somatostatin and its receptors (SSTR-1 to SSTR-5) are expressed in normal human parafollicular C cells and medullary thyroid carcinoma (MTC). MTC is a tumor originating from thyroid parafollicular C cells that produces calcitonin (CT), somatostatin, and several other peptides. It was recently demonstrated that SS and SSTR's are expressed in human MTC, and SS and SS analogues were shown to induce a decrease in plasma CT levels and provide symptomatic improvement in MTC patients. Another recent study has shown that SS and SS analogs, in particular, SSTR-1 and SSTR-2, can inhibit the proliferation of tumor cells, suggesting that specific SSTR subtypes can function in MTC cell growth regulation. The development and characterization of SSTR subtype analogues that selectively effect MTC cell growth is useful for clinical and therapeutic applications.

SUMMARY OF THE INVENTION

The present invention is based on our discovery of somatostatin-dopamine chimeric analogs, comprising compounds that retain both somatostatin and dopamine activity. The chimeric analogs of the invention are considered to be useful, e.g., in vitro, for use as research tools, diagnostic assays, etc., or in vivo, for use as diagnostic or therapeutic agents. Preferred chimeric analogs of the invention display enhanced activity when compared to native somatostatin and dopamine, either alone or in combination.

Accordingly, in a first aspect, the invention features a chimeric analog comprising (1) at least one moiety which binds to one or more somatostatin receptor(s) and (2) at least one moiety which binds to one or more dopamine receptor(s), or a pharmaceutically acceptable salt thereof.

In a first embodiment of the first aspect, the chimeric analog comprises formula (I),

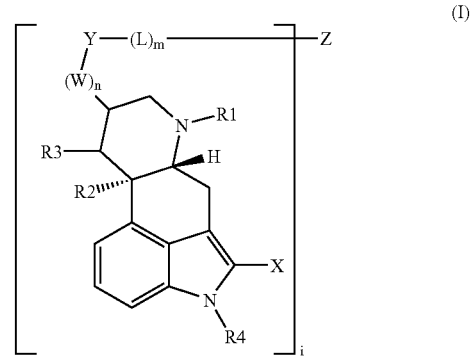

wherein:

X is H, Cl, Br, I, F, —CN, $C_{1-10}$ alkyl, $C_{1-10}$ heteroalkyl, $C_{2-10}$ alkenyl, $C_{2-10}$ alkynyl, substituted $C_{1-10}$ alkyl, substituted $C_{1-10}$ heteroalkyl, substituted $C_{2-10}$ alkenyl, or substituted $C_{2-10}$ alkynyl;

R1 is H, $C_{1-10}$ alkyl, $C_{1-10}$ heteroalkyl, $C_{2-10}$ alkenyl, $C_{2-10}$ alkynyl, substituted $C_{1-10}$ alkyl, substituted $C_{1-10}$ heteroalkyl, substituted $C_{2-10}$ alkenyl, substituted $C_{2-10}$ alkynyl, or —CN;

R2 and R3, each is, independently, H or absent, provided that when R2 and R3 are absent a double bond is present between the carbon atoms to which they are attached;

R4 is H, $C_{1-10}$ alkyl, $C_{1-10}$ heteroalkyl, $C_{2-10}$ alkenyl, $C_{2-10}$ alkynyl, substituted $C_{1-10}$ alkyl, substituted $C_{1-10}$ heteroalkyl, substituted $C_{2-10}$ alkenyl, or substituted $C_{2-10}$ alkynyl;

Y is —O—, —C(O)—, —S—, —S—$(CH_2)_s$—C(O)—, —S(O)—, —S(O)$_2$—, —SC(O)—, —OC(O)—, —N(R5)-C(O)—, or —N(R6)-;

L is —$(CH_2)_p$—C(O)—, when Y is —S—, —S(O)—, —S(O)$_2$—, —O— or —N(R6)-; or L is —C(O)—(CR7R8)$_q$—C(O)—, when Y is —N(R6)-, —O—, or —S—; or L is (amino acid)$_t$, when Y is —C(O)—, SC(O)—, —OC(O)—, —S—$(CH_2)_s$—C(O)—, or —N(R5)-C(O)—;

W is —CR9,R10-;

R5 and R6 each is, independently, H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted alkylaryl;

R7, R8, R9, and R10 each is, independently, H, F, Cl, Br, I, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl; or R7 and R8 can, optionally, join together to form a ring system; or R9 and R10 can, optionally, join together to form a ring system;

i is 1-10, provided that when i is 1, then R1 is not H, $C_{1-4}$ alkyl, allyl, alkenyl or —CN, R4 is not H or —CH$_3$, R5, R6, R7 and R8 each is, independently, not H or $C_{1-5}$ alkyl, L is not -(Doc)t-, X is not H, Cl, Br, I, F, —CN, or $C_{1-5}$ alkyl, or R9 and R10 each is, independently, not H;

m is 0 or 1;
n is 0-10;
p is 1-10;
q is 1-5;
s is 1-10;
t is 1-10;

Z is a ligand of at least one somatostatin receptor;
or a pharmaceutically acceptable salt thereof; and
wherein each moiety depicted between the brackets is, independently for each occurrence, attached to an N-terminal or an internal amine group or hydroxyl group of Z.

In a second aspect of the first embodiment, the chimeric analog comprises formula (II),

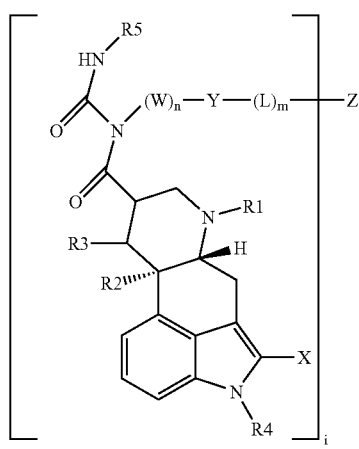

(II)

wherein:

X is H, Cl, Br, I, F, —CN, $C_{1-10}$ alkyl, $C_{1-10}$ heteroalkyl, $C_{2-10}$ alkenyl, $C_{2-10}$ alkynyl, substituted $C_{1-10}$ alkyl, substituted $C_{1-10}$ heteroalkyl, substituted $C_{2-10}$ alkenyl, or substituted $C_{2-10}$ alkynyl;

R1 is H, $C_{1-10}$ alkyl, $C_{1-10}$ heteroalkyl, $C_{2-10}$ alkenyl, $C_{2-10}$ alkynyl, substituted $C_{1-10}$ alkyl, substituted $C_{1-10}$ heteroalkyl, substituted $C_{2-10}$ alkenyl, substituted $C_{2-10}$ alkynyl, or —CN;

R2 and R3, each is, independently, H or absent, provided that when R2 and R3 are absent a double bond is present between the carbon atoms to which they are attached;

R4 is H, $C_{1-10}$ alkyl, $C_{1-10}$ heteroalkyl, $C_{2-10}$ alkenyl, $C_{2-10}$ alkynyl, substituted $C_{1-10}$ alkyl, substituted $C_{1-10}$ heteroalkyl, substituted $C_{2-10}$ alkenyl, or substituted $C_{2-10}$ alkynyl;

R5 is H, $C_{1-10}$ alkyl, $C_{1-10}$ heteroalkyl, $C_{2-10}$ alkenyl, $C_{2-10}$ alkynyl, substituted $C_{1-10}$ alkyl, substituted $C_{1-10}$ heteroalkyl, substituted $C_{2-10}$ alkenyl, substituted $C_{2-10}$ alkynyl, or a group of the formula of —$(CH_2)_r$N(R11, R12);

Y is —O—, —C(O)—, —S—, —SC(O)—, —OC(O)—, —N(R6)-C(O)—, —N(R7)-, or —N(R8)-$(CH_2)_s$—C(O)—;

L is —$(CH_2)_p$—C(O)—, when Y is —S—, —O— or —N(R7)-; or L is —C(O)—(CR9R10)$_q$—C(O)—, when Y is —N(R7)-, —O—, or —S—; or L is (amino acid)$_t$, when Y is —C(O)—, SC(O)—, —OC(O)—, —N(R8)-$(CH_2)_s$—C(O)—, or —N(R6)-C(O)—;

W is —CR9,R10-;

R6, R7, and R8 each is, independently, H, $C_{1-10}$ allyl, substituted $C_{1-10}$ alkyl, $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

R9 and R10 each is, independently, H, Cl, Br, I, F, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl; or R9 and R10 can, optionally, join together to form a ring system;

R11 and R12 each is, independently, H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

i is 1-10, provided that when i is 1, then R1 is not H, $C_{1-4}$ alkyl, allyl, alkenyl or —CN, R4 is not H or —CH$_3$, R5 is not $C_{1-5}$ alkyl group or a group of the formula of —$(CH_2)_v$N$(CH_3)_v$, R6, R7, R8, R9 and R10 each is, independently, not H or $C_{1-5}$ alkyl, L is not -(Doc)t-, or X is not H, Cl, Br, I, F, —CN, or $C_{1-5}$ alkyl;

m is 0 or 1;
n is 2-10;
p is 1-10;
q is 1-5;
r is 1-8;
s is 1-10;
t is 1-10;
v is 2-4;

Z is a ligand of at least one somatostatin receptor; or
a pharmaceutically acceptable salt thereof; and
wherein each moiety depicted between the brackets is, independently for each occurrence, attached to an N-terminal or an internal amine group or hydroxyl group of Z.

In a third embodiment of the first aspect, the chimeric analog of claim 1, wherein said chimeric analog comprises formula (III),

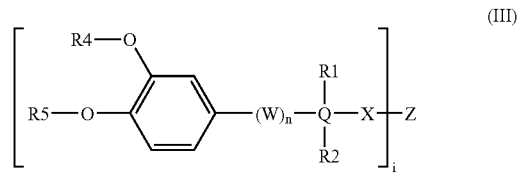

(III)

wherein:

R2 is H, —N(R11)N(R12,R13), —N(R6R7), or —COOH;

R4 and R5 each is, independently, H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, substituted akylaryl or R8—C(O)—;

W is —CR9R10- or —$(CH_2)_q$—NH—$(CH_2)_r$—;

R1, R6, R7, R8, R11, R12 and R13 each is, independently, H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

R9 and R10 each is, independently, H, —OH, —CN, —$NO_2$, F, Cl, Br, I, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, akylaryl, substituted alkylaryl, or aryl;

X is $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, akylaryl, substituted alkylaryl, aryl, or acyl;

Q is C or N; provided that when Q is N, then R2 is absent;

i is 1-10;

n is 1-6;

q is 1-6;

r is 1-8;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In a fourth embodiment of the first aspect, the chimeric analog comprises formula (IV),

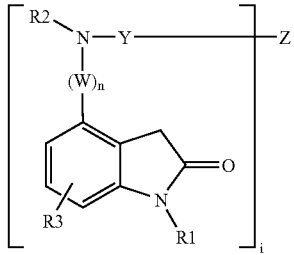

(IV)

wherein:

R1 and R2 each is, independently, H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

R3, R4, R5, R6 and R7 each is, independently, H, —OH, —CN, —$NO_2$, F, Cl, Br, I, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

W is —CR4R5-;

Y is —$(CR6R7)_m$-C(O)— or acyl;

m is 0-10;

n is 1-6;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In a fifth embodiment of the first aspect, the chimeric analog comprises formula (V),

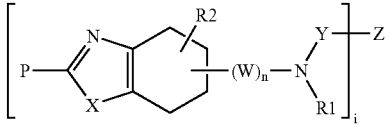

(V)

wherein:

P is —N(R3R4) or H;

X is N or S;

W is —CR5R6-;

Y is —$(CR7R8)_m$-C(O)—;

R1, R3 and R4 each is, independently, H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

R2, R5, R6, R7 and R8 each is, independently, H, —OH, —CN, —$NO_2$, F, Cl, Br, I, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

i is 1-10;

m is 0-10;

n is 0-6;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In a sixth aspect of the first embodiment, the chimeric analog comprises formula (VI),

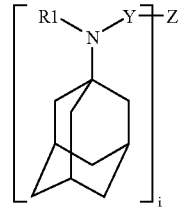

(VI)

wherein:

Y is —$(CR2R3)_m$-C(O)— or acyl;

R1 is H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

R2 and R3 each is, independently, H, —OH, —CN, —$NO_2$, F, Cl, Br, I, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

i is 1-10;

m is 0-10;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In a seventh embodiment of the first aspect, the chimeric analog comprises formula (VII),

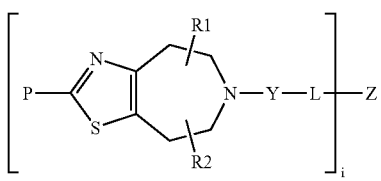

(VII)

wherein:

P is —N(R3R4) or H;

L is —(CR5R6)$_m$-C(O)— or acyl;

Y is $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, substituted akylaryl, or absent;

R1, R2, R5 and R6 each is, independently, H, —OH, —CN, —NO$_2$, F, Cl, Br, I, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

R3 and R4 each is, independently, H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

i is 1-10;

m is 0-10;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In an eighth embodiment of the first aspect, the chimeric analog comprises formula (VIII),

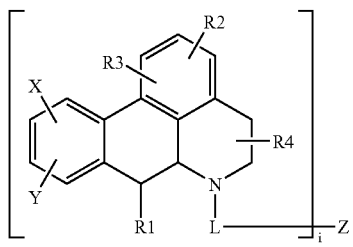

(VIII)

wherein:

X and Y each is, independently, —OH, —OR4 or R5-C(O)—O—;

L is —CR3R4)$_m$-C(O)— or acyl;

R1, R2, R3 and R4 each is, independently, H, —OH, F, Cl, Br, I, —CN, NO$_2$, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl; or R2 and R3 can, optionally, join together to form a ring system;

R5 is H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

i is 1-10;

m is 0-10;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In a ninth embodiment of the first aspect, the chimeric analog comprises formula (IX),

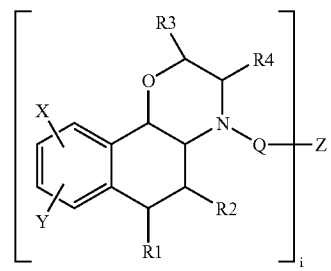

(IX)

wherein:

X and Y each is, independently, —OH, —OR4 or R7-C(O)—;

Q is —CR5R6)$_m$-C(O)— or acyl;

R1, R2, R3, R4, R5 and R6 each is, independently, H, —OH, F, Cl, Br, I, —CN, NO$_2$, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl; or R1 and R2 can, optionally, join together to form a ring system; or R3 and R4 can, optionally, join together to form a ring system;

R7 is H, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

i is 1-10;

m is 0-10;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In a tenth embodiment of the first aspect, the chimeric analog comprises formula (X),

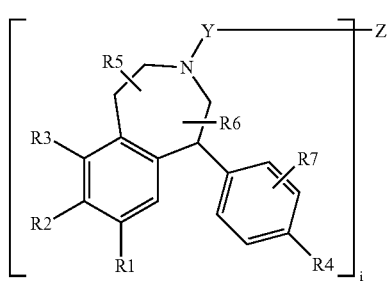

(X)

wherein:

Y is —CR8R9)$_m$-C(O)— or acyl;

R1, R2, R3, R4, R5, R6, R7, R8 and R9 each is, independently, H, —OH, F, Cl, Br, I, —CN, NO$_2$, $C_{1-10}$ alkyl, substituted $C_{1-10}$ alkyl; $C_{1-10}$ heteroalkyl, substituted $C_{1-10}$ heteroalkyl, $C_{2-10}$ alkenyl, substituted $C_{2-10}$ alkenyl, $C_{2-10}$ alkynyl, substituted $C_{2-10}$ alkynyl, aryl, alkylaryl, or substituted akylaryl;

i is 1-10;

m is 0-10;

Z is a ligand of at least one somatostatin receptor; or a pharmaceutically acceptable salt thereof; and wherein each moiety depicted between the brackets is, independently for each occurrence, attached to an N-terminal or an internal amine group or hydroxyl group of Z.

In another embodiment of the first aspect, the chimeric analog comprises any of the compounds listed in Table 1; or a pharmaceutically acceptable salt thereof.

In another embodiment of the first aspect, the chimeric analog comprises a compound according to the formula of:

Dop2-DPhe-Doc-DPhe-cyclo[Cys-3ITyr-DTrp-Lys-Val-Cys]-Thr-NH$_2$,

Dop2-DPhe-Doc-DPhe-cyclo[Cys-3ITyr(Dop2)-DTrp-Lys-Val-Cys]-Thr-NH$_2$,

Ac-Lys(Dop2)-DTyr-DTyr-cyclo[Cys-Tyr-DTrp-Lys-Abu-Cys]-Thr-NH$_2$,

Ac-DLys(Dop2)-DPhe-cyclo[Cys-3ITyr-DTrp-Lys-Thr-Cys]-Thr-NH$_2$,

Dop3-DPhe-cyclo[Cys-Tyr-DTrp-Lys-Abu-Cys]-Thr-NH$_2$,

Dop4-DPhe-cyclo[Cys-Tyr-DTrp-Lys-Abu-Cys]-Thr-NH$_2$,

Dop5-DPhe-cyclo[Cys-Tyr-DTrp-Lys-Abu-Cys]-Thr-NH$_2$,

Dop2-DPhe-cyclo[Cys-3ITyr-DTrp-Lys-Thr-Cys]-Thr-NH$_2$,

Dop2-Lys(Dop2)-DPhe-cyclo[Cys-Tyr-DTrp-Lys-Abu-Cys]-Thr-NH$_2$,

Dop2-Lys(Dop2)-cyclo[Cys-Tyr-DTrp-Lys-Abu-Cys]-Thr-NH$_2$,

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$,

Dap5-Lys(Dop5)-DPhe-cyclo[Cys-Tyr-DTrp-Lys-Abu-Cys]-Thr-NH$_2$,

Dop2-DPhe-cyclo[Cys-3ITyr(Dop2)-DTrp-Lys-Val-Cys]-Thr-NH$_2$,

Dop2-Lys(Dop2)-DTyr-DTyr-cyclo[Cys-3ITyr-DTrp-Lys-Thr-Cys]-Thr-NH$_2$,

Dop2-Lys(Dop2)-DPhe-cyclo[Cys-3ITyr-DTrp-Lys-Thr-Cys]-Thr-NH$_2$, or

Dop2-DLys(Dop2)-DPhe-cyclo[Cys-3ITyr-DTrp-Lys-Thr-Cys]Thr-NH$_2$; or a pharmaceutically acceptable salt thereof.

In a preferred embodiment of the first aspect, the chimeric analog comprises a compound according to the formula of:

Dop2-Lys(Dop2)-DTyr-DTyr-cyclo[Cys-Tyr-DTrp-Lys-Abu-Cys]Thr-NH$_2$,

Dop2-DLys(Dop2)-cyclo[Cys-Tyr-DTrp-Lys-Abu-Cys]-Thr-NH$_2$, or

Dop2-DPhe-cyclo[Cys-3ITyr-DTrp-Lys-Thr-Cys]-Thr-NH$_2$; or a pharmaceutically acceptable salt thereof.

In a more preferred embodiment of the first aspect, the chimeric analog comprises a compound according to the formula of Dop2-Lys(Dop2)-DTyr-DTyr-cyclo[Cys-Tyr-DTrp-Lys-Abu-Cys]-Thr-NH2; or a pharmaceutically acceptable salt thereof. In another more preferred embodiment, the chimeric analog comprises a compound according to the formula of Dop2-DLys(Dop2)-cyclo[Cys-Tyr-DTrp-Lys-Abu-Cys]-Thr-NH2; or a pharmaceutically acceptable salt thereof. In yet another more preferred embodiment, the chimeric analog comprises a compound according to the formula of Dop2-DPhe-cyclo[Cys-3ITyr-DTrp-Lys-Thr-Cys]-Thr-NH2; or a pharmaceutically acceptable salt thereof.

In another embodiment of the first aspect, the chimeric analog comprises a compound according to the formula of:

Dop2-Lys(Dop2)-DTyr-Tyr-cyclo[DDab-Arg-Phe-Phe-DTrp-Lys-Thr-Phe],

Dop2-Tyr-cyclo[DDab-Arg-Phe-Phe-DTrp-Lys-Thr-Phe], or

Dop2-DTyr-Dtyr-Caeg-cyclo[DCys-3Pal-DTrp-Lys-Dcys]-Thr(Bzl)-Tyr-NH$_2$; or a pharmaceutically acceptable salt thereof In a second aspect, the invention features a compound useful as an intermediate in a chemical synthesis, wherein said intermediate comprises a compound according to formula (3), (6), (11), (14), (18), (21), (24), or (27) (referred to herein as intermediate compound (3), (6), (11), (14), (18), (21), (24), and (27), respectively) as shown below:

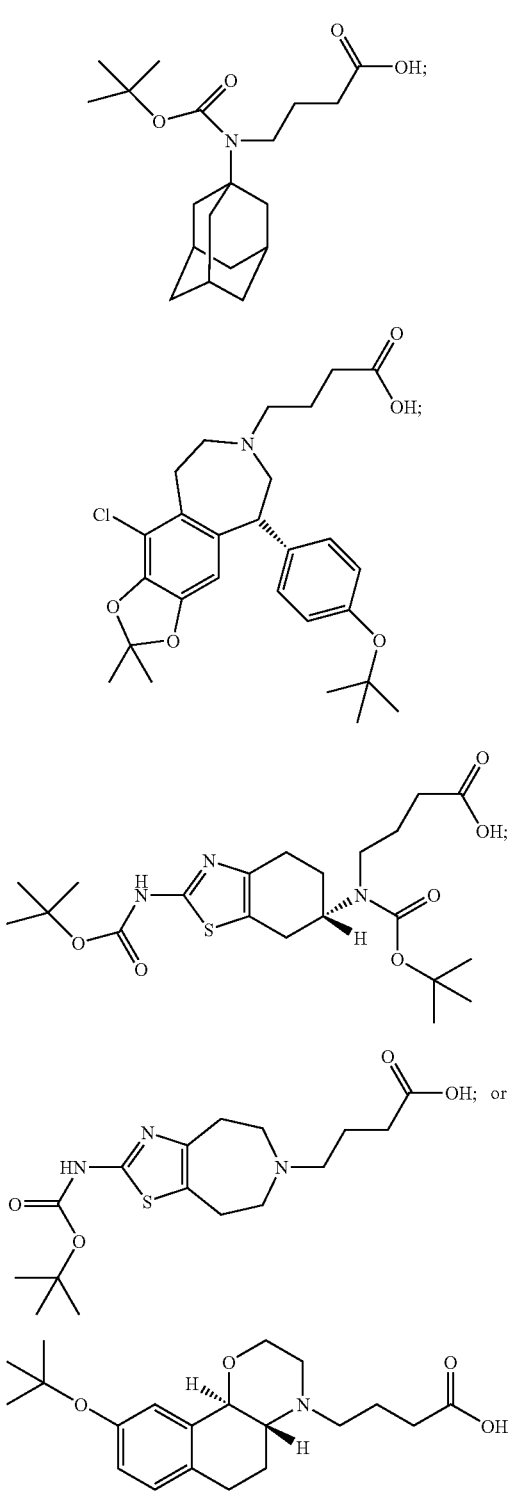

or an organic or inorganic salt thereof.

In a third aspect, the invention features a method of eliciting a dopamine receptor agonist effect in a subject in need thereof, wherein said method comprises administering to said subject an effective amount of a chimeric analog of the invention, wherein said chimeric analogue comprises a compound according to the formula of Formula (I), (II), (III), (IV), (V), (VI) (VII), (VIII), (IX), or (X), or a pharmaceutically acceptable salt thereof; or intermediate compound (3), (6), (11), (14), (18), (21), (24), or (27), or an organic or inorganic salt thereof; and wherein said effective amount is the amount effective to elicit a dopamine receptor agonist effect in said subject.

In a first embodiment of the third aspect, the chimeric analog comprises any of the compounds listed in Table 1; or a pharmaceutically acceptable salt thereof.

In a second embodiment of the third aspect, the chimeric analog comprises a compound according to the formula of:

Dop2-DPhe-Doc-DPhe-cyclo[Cys-3ITyr-DTrp-Lys-Val-Cys]-Thr-NH$_2$,

Dop2-DPhe-Doc-DPhe-cyclo[Cys-3ITyr(Dop2)-DTrp-Lys-Val-Cys]-Thr-NH$_2$,

Ac-Lys(Dop2)-DTyr-DTyr-cyclo[Cys-Tyr-DTrp-Lys-Abu-Cys]-Thr-NH$_2$,

Ac-DLys(Dop2)-DPhe-cyclo[Cys-3ITyr-DTrp-Lys-Thr-Cys]-Thr-NH$_2$,

Dop3-DPhe-cyclo[Cys-Tyr-DTrp-Lys-Abu-Cys]-Thr-NH$_2$,

Dop4-DPhe-cyclo[Cys-Tyr-DTrp-Lys-Abu-Cys]-Thr-NH$_2$,

Dop5-DPhe-cyclo[Cys-Tyr-DTrp-Lys-Abu-Cys]-Thr-NH$_2$,

Dop2-DPhe-cyclo[Cys-3ITyr-DTrp-Lys-Thr-Cys]-Thr-NH$_2$,

Dop2-Lys(Dop2)-DPhe-cyclo[Cys-Tyr-DTrp-Lys-Abu-Cys]-Thr-NH$_2$,

Dop2-Lys(Dop2)-cyclo[Cys-Tyr-DTrp-Lys-Abu-Cys]-Thr-NH$_2$,

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$,

Dop5-Lys(Dop5)-DPhe-cyclo[Cys-Tyr-DTrp-Lys-Abu-Cys]-Thr-NH$_2$,

Dop2-DPhe-cyclo[Cys-3ITyr(Dop2)-DTrp-Lys-Val-Cys]-Thr-NH$_2$,

Dop2-Lys(Dop2)-DTyr-DTyr-cyclo[Cys-3ITyr-DTrp-Lys-Thr-Cys]-Thr-NH$_2$,

Dop2-Lys(Dop2)-DPhe-cyclo[Cys-3ITyr-DTrp-Lys-Thr-Cys]-Thr-NH$_2$, or

Dop2-DLys(Dop2)-DPhe-cyclo[Cys-3ITyr-DTrp-Lys-Thr-Cys]-Thr-NH$_2$; or a pharmaceutically acceptable salt thereof.

In a preferred embodiment, the chimeric analog comprises a compound according to the formula of:

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$, or

Dop2-DPhe-cyolo[Cys-3ITyr-DTrp-Lys-Thr-Cys]-Thr-NH$_2$; or a pharmaceutically acceptable salt thereof.

In a more preferred embodiment of the third aspect, the chimeric analog comprises a compound according to the formula of Dop2-Lys(Dop2)-DTyr-DTyr-cyclo[Cys-Tyr-DTrp-Lys-Abu-Cys]-Thr-NH2; or a pharmaceutically acceptable salt thereof.

In another more preferred embodiment of the third aspect, chimeric analogue comprises a compound according to the formula of Dop2-DLys(Dop2)-cyclo[Cys-Tyr-DTrp-Lys-Abu-Cys]-Thr-NH2; or a pharmaceutically acceptable salt thereof. In yet another more preferred embodiment of the third aspect, chimeric analogue comprises a compound according to the formula of Dop2-DPhe-cyclo[Cys-3ITyr-DTrp-Lys-Thr-Cys]-Thr-NH2; or a pharmaceutically acceptable salt thereof. In a third embodiment of the third aspect, the chimeric analogue comprises a compound according to the formula of:

Dop2-Lys(Dop2)-DTyr-Tyr-cyclo[DDab-Arg-Phe-Phe-DTrp-Lys-Thr-Phe],

Dop2-Tyr-cyclo[DDab-Arg-Phe-Phe-DTrp-Lys-Thr-Phe], or

Dop2-DTyr-DTyr-Caeg-cyclo[DCys-3Pal-DTrp-Lys-Dcys]-Thr(Bzl)-Tyr-NH$_2$; or a pharmaceutically acceptable salt thereof.

In a fourth aspect, the invention features a method of eliciting a somatostatin receptor agonist effect in a subject in need thereof, wherein said method comprises administering to said subject an effective amount of a chimeric analogue of the invention, wherein said chimeric analogue comprises a compound according to the formula of Formula (I), (II), (III), (IV), (V), (VI) (VII), (VIII), (IX), or (X), or a pharmaceutically acceptable salt thereof; or intermediate compound (3), (6), (11), (14), (18), (21), (24), or (27), or an organic or inorganic salt thereof; and wherein said effective amount is the amount effective to elicit a somatostatin receptor agonist effect in said subject.

In a first embodiment of the fourth aspect, the chimeric analogue comprises any of the compounds listed in Table 1; or a pharmaceutically acceptable salt thereof.

In a second embodiment of the fourth aspect, the chimeric analogue comprises a compound according to the formula of:

Dop2-DPhe-Doc-DPhe-cyclo[Cys-3ITyr-DTrp-Lys-Val-Cys]-Thr-NH$_2$,

Dop2-DPhe-Doc-DPhe-cyclo[Cys-3ITyr(Dop2)-DTrp-Lys-Val-Cys]-Thr-NH$_2$,

Ac-Lys(Dop2)-DTyr-DTyr-cyclo[Cys-Tyr-DTrp-Lys-Abu-Cys]-Thr-NH$_2$,

Ac-DLys(Dop2)-DPhe-cyclo[Cys-3ITyr-DTrp-Lys-Thr-Cys]-Thr-NH$_2$,

Dop3-DPhe-cyclo[Cys-Tyr-DTrp-Lys-Abu-Cys]-Thr-NH$_2$,

Dop4-DPhe-cyclo[Cys-Tyr-DTrp-Lys-Abu-Cys]-Thr-NH$_2$,

Dop5-DPhe-cyclo[Cys-Tyr-DTrp-Lys-Abu-Cys]-Thr-NH$_2$,

Dop2-DPhe-cyclo[Cys-3ITyr-DTrp-Lys-Thr-Cys]-Thr-NH$_2$,

Dop2-Lys(Dop2)-DPhe-cyclo[Cys-Tyr-DTrp-Lys-Abu-Cys]-Thr-NH$_2$,

Dop2-Lys(Dop2)-cyclo[Cys-Tyr-DTrp-Lys-Abu-Cys]-Thr-NH$_2$,

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$,

Dop5-Lys(Dop5)-DPhe-cyclo[Cys-Tyr-DTrp-Lys-Abu-Cys]-Thr-NH$_2$,

Dop2-DPhe-cyclo[Cys-3ITyr(Dop2)-DTrp-Lys-Val-Cys]-Thr-NH$_2$,

Dop2-Lys(Dop2)-DTyr-DTyr-cyclo[Cys-3ITyr-DTrp-Lys-Thr-Cys]-Thr-NH$_2$,

Dop2-Lys(Dop2)-DPhe-cyclo[Cys-3ITyr-DTrp-Lys-Thr-Cys]-Thr-NH$_2$, or

Dop2-DLys(Dop2)-DPhe-cyclo[Cys-3ITyr-DTrp-Lys-Thr-Cys]Thr-NH$_2$; or a pharmaceutically acceptable salt thereof.

In a preferred embodiment, the chimeric analogue comprises a compound according to the formula of:

Dop2-Lys(Dop2)-DTyr-DTyr-cyclo[Cys-Tyr-DTrp-Lys-Abu-Cys]Thr-NH$_2$,

Dop2-DLys(Dop2)-cyclo[Cys-Tyr-DTrp-Lys-Abu-Cys]-Thr-NH$_2$, or

Dop2-DPhe-cyclo[Cys-3ITyr-DTrp-Lys-Thr-Cys]-Thr-NH$_2$; or a pharmaceutically acceptable salt thereof.

In a more preferred embodiment of the fourth aspect, the chimeric analog comprises a compound according to the formula of Dop2-Lys(Dop2)-DTyr-DTyr-cyclo[Cys-Tyr-DTrp-Lys-Abu-Cys]-Thr-NH2; or a pharmaceutically acceptable salt thereof. In another more preferred embodiment of the fourth aspect, chimeric analogue comprises a compound according to the formula of Dop2-DLys(Dop2)-cyclo[Cys-Tyr-DTrp-Lys-Abu-Cys]-Thr-NH$_2$; or a pharmaceutically acceptable salt thereof. In yet another more preferred embodiment of the fourth aspect, chimeric analogue comprises a compound according to the formula of Dop2-DPhe-cyclo[Cys-3ITyr-DTrp-Lys-Thr-Cys]-Thr-NH$_2$; or a pharmaceutically acceptable salt thereof.

In a third embodiment of the fourth aspect, the chimeric analogue comprises a compound according to the formula of:

Dop2-Lys(Dop2)-DTyr-Tyr-cyclo[DDab-Arg-Phe-Phe-DTrp-Lys-Thr-Phe],

Dop2-Tyr-cyclo[DDab-Arg-Phe-Phe-DTrp-Lys-Thr-Phe], or

Dop2-DTyr-DTyr-Caeg-cyclo[DCys-3Pal-DTrp-Lys-Dcys]-Thr(Bzl)-Tyr-NH$_2$; or a pharmaceutically acceptable salt thereof.

In a fifth aspect, the invention features a method of eliciting both a dopamine receptor agonist effect and a somatostatin receptor agonist effect in a subject in need thereof, wherein said method comprises administering to said subject an effective amount of a chimeric analogue of the invention, wherein said chimeric analogue comprises a compound according to the formula of Formula (I), (II), (III), (IV), (V), (VI) (VII), (VIII), (IX), or (X), or a pharmaceutically acceptable salt thereof, or intermediate compound (3), (6), (11), (14), (18), (21), (24), or (27), or an organic or inorganic salt thereof, and wherein said effective amount is the amount effective to elicit both a dopamine and a somatostatin receptor agonist effect in said subject.

In a first embodiment of the fifth aspect, the chimeric analogue comprises any of the compounds listed in Table 1; or a pharmaceutically acceptable salt thereof.

In a second embodiment of the fifth aspect, the chimeric analogue comprises a compound according to the formula of:

```
Dop2-DPhe-Doc-DPhe-cyclo[Cys-3ITyr-DTrp-Lys-Val-
Cys]-Thr-NH2,

Dop2-DPhe-Doc-DPhe-cyclo[Cys-3ITyr(Dop2)-DTrp-Lys-
Val-Cys]-Thr-NH2,

Ac-Lys(Dop2)-DTyr-DTyr-cyclo[Cys-Tyr-DTrp-Lys-Abu-
Cys]-Thr-NH2,

Ac-DLys(Dop2)-DPhe-cyclo[Cys-3ITyr-DTrp-Lys-Thr-
Cys]-Thr-NH2,

Dop3-DPhe-cyclo[Cys-Tyr-DTrp-Lys-Abu-Cys]-Thr-NH2,

Dop4-DPhe-cyclo[Cys-Tyr-DTrp-Lys-Abu-Cys]-Thr-NH2,

Dop5-DPhe-cyclo[Cys-Tyr-DTrp-Lys-Abu-Cys]-Thr-NH2,

Dop2-DPhe-cyclo[Cys-3ITyr-DTrp-Lys-Thr-Cys]-Thr-
NH2,

Dop2-Lys(Dop2)-DPhe-cyclo[Cys-Tyr-DTrp-Lys-Abu-
Cys]-Thr-NH2,

Dop2-Lys(Dop2)-cyclo[Cys-Tyr-DTrp-Lys-Abu-Cys]-
Thr-NH2,

Dop2-Lys(Dop2)-DTyr-DTyr-cyclo[Cys-Tyr-DTrp-Lys-
Abu-Cys]-Thr-NH2,

Dop2-DLys(Dop2)-cyclo[Cys-Tyr-DTrp-Lys-Abu-Cys]-
Thr-NH2,

Dop5-Lys(Dop5)-DPhe-cyclo[Cys-Tyr-DTrp-Lys-Abu-
Cys]-Thr-NH2,

Dop2-DPhe-cyclo[Cys-3ITyr(Dop2)-DTrp-Lys-Val-Cys]-
Thr-NH2,

Dop2-Lys(Dop2)-DTyr-DTyr-cyclo[Cys-3ITyr-DTrp-Lys-
Thr-Cys]-Thr-NH2,

Dop2-Lys(Dop2)-DPhe-cyclo[Cys-3ITyr-DTrp-Lys-Thr-
Cys]-Thr-NH2, or

Dop2-DLys(Dop2)-DPhe-cyclo[Cys-3ITyr-DTrp-Lys-Thr-
Cys]-Thr-NH2; or
``` a pharmaceutically acceptable salt thereof.

In a preferred embodiment, the chimeric analogue comprises a compound according to the formula of:

```
Dop2-Lys(Dop2)-DTyr-DTyr-cyclo[Cys-Tyr-DTrp-Lys-
Abu-Cys]-Thr-NH2,

Dop2-DLys(Dop2)-cyclo[Cys-Tyr-DTrp-Lys-Abu-Cys]-
Thr-NH2, or

Dop2-DPhe-cyclo[Cys-3ITyr-DTrp-Lys-Thr-Cys]-Thr-
NH2; or
``` a pharmaceutically acceptable salt thereof.

In a more preferred embodiment of the fifth aspect, the chimeric analog comprises a compound according to the formula of Dop2-Lys(Dop2)-DTyr-DTyr-cyclo[Cys-Tyr-DTrp-Lys-Abu-Cys]-Thr-NH2; or a pharmaceutically acceptable salt thereof. In another more preferred embodiment of the fifth aspect, chimeric analogue comprises a compound according to the formula of Dop2-DLys(Dop2)-cyclo[Cys-Tyr-DTrp-Lys-Abu-Cys]-Thr-NH$_2$; or a pharmaceutically acceptable salt thereof. In yet another more preferred embodiment of the fifth aspect, chimeric analogue comprises a compound according to the formula of Dop2-DPhe-cyclo[Cys-3ITyr-DTrp-Lys-Thr-Cys]-Thr-NH$_2$; or a pharmaceutically acceptable salt thereof.

In a third embodiment of the fifth aspect, the chimeric analogue comprises a compound according to the formula of:

```
Dop2-Lys(Dop2)-DTyr-Tyr-cyclo[DDab-Arg-Phe-Phe-
DTrp-Lys-Thr-Phe],

Dop2-Tyr-cyclo[DDab-Arg-Phe-Phe-DTrp-Lys-Thr-Phe],
or

Dop2-DTyr-DTyr-Caeg-cyclo[DCys-3Pal-DTrp-Lys-
Dcys]-Thr(Bzl)-Tyr-NH2; or
``` a pharmaceutically acceptable salt thereof.

In a sixth aspect, the invention features a pharmaceutical composition comprising an effective amount of a compound according to the formula of Formula (I), (II), (III), (IV), (V), (VI) (VII), (VIII), (IX), or (X), or a pharmaceutically acceptable salt thereof; or intermediate compound (3), (6), (11), (14), (18), (21), (24), or (27), or an organic or inorganic salt thereof; in a pharmaceutically acceptable carrier, wherein said effective amount is the amount effective to elicit a dopamine receptor agonist effect or a somatostatin receptor agonist effect or both in a subject in need thereof.

In a first embodiment of the sixth aspect, the chimeric analogue comprises any of the compounds listed in Table 1; or a pharmaceutically acceptable salt thereof.

In a second embodiment of the sixth aspect, the chimeric analogue comprises a compound according to the formula of:

```
Dop2-DPhe-Doc-DPhe-cyclo[Cys-3ITyr-DTrp-Lys-Val-
Cys]-Thr-NH2,

Dop2-DPhe-Doc-DPhe-cyclo[Cys-3ITyr(Dop2)-DTrp-Lys-
Val-Cys]-Thr-NH2,

Ac-Lys(Dop2)-DTyr-DTyr-cyclo[Cys-Tyr-DTrp-Lys-Abu-
Cys]-Thr-NH2,

Ac-DLys(Dop2)-DPhe-cyclo[Cys-3ITyr-DTrp-Lys-Thr-
Cys]-Thr-NH2,

Dop3-DPhe-cyclo[Cys-Tyr-DTrp-Lys-Abu-Cys]-Thr-NH2,

Dop4-DPhe-cyclo[Cys-Tyr-DTrp-Lys-Abu-Cys]-Thr-NH2,

Dop5-DPhe-cyclo[Cys-Tyr-DTrp-Lys-Abu-Cys]-Thr-NH2,

Dop2-DPhe-cyclo[Cys-3ITyr-DTrp-Lys-Thr-Cys]-Thr-
NH2,

Dop2-Lys(Dop2)-DPhe-cyclo[Cys-Tyr-DTrp-Lys-Abu-
Cys]-Thr-NH2,

Dop2-LYS(Dop2)-cyclo[Cys-Tyr-DTrp-Lys-Abu-Cys]-
Thr-NH2,

Dop2-Lys(Dop2)-DTyr-DTyr-cyclo[Cys-Tyr-DTrp-Lys-
Abu-Cys]-Thr-NH2,

Dop2-DLys(Dop2)-cyclo[Cys-Tyr-DTrp-Lys-Abu-Cys]-
Thr-NH2,
```

-continued

Dop5-Lys(Dop5)-DPhe-cyclo[Cys-Tyr-DTrp-Lys-Abu-Cys]-Thr-NH$_2$,

Dop2-DPhe-cyclo[Cys-3ITyr(Dop2)-DTrp-Lys-Val-Cys]-Thr-NH$_2$,

Dop2-Lys(Dop2)-DTyr-DTyr-cyclo[Cys-3ITyr-DTrp-Lys-Thr-Cys]-Thr-NH2,

Dop2-Lys(Dop2)-DPhe-cyclo[Cys-3ITyr-DTrp-Lys-Thr-Cys]-Thr-NH$_2$, or

Dop2-DLys(Dop2)-DPhe-cyclo[Cys-3ITyr-DTrp-Lys-Thr-Cys]-Thr-NH$_2$; or a pharmaceutically acceptable salt thereof.

In a preferred embodiment, the chimeric analogue comprises a compound according to the formula of:

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$, or

Dap2-DPhe-cyclo[Cys-3ITyr-DTrp-Lys-Thr-Cys]-Thr-NH$_2$; or a pharmaceutically acceptable salt thereof.

In a more preferred embodiment of the sixth aspect, the chimeric analog comprises a compound according to the formula of Dop2-Lys(Dop2)-DTyr-DTyr-cyclo[Cys-Tyr-DTrp-Lys-Abu-Cys]-Thr-NH2; or a pharmaceutically acceptable salt thereof. In another more preferred embodiment of the sixth aspect, chimeric analogue comprises a compound according to the formula of Dop2-DLys(Dop2)-cyclo[Cys-Tyr-DTrp-Lys-Abu-Cys]-Thr-NH$_2$; or a pharmaceutically acceptable salt thereof. In yet another more preferred embodiment of the sixth aspect, chimeric analogue comprises a compound according to the formula of Dop2-DPhe-cyclo[Cys-3ITyr-DTrp-Lys-Thr-Cys]-Thr-NH$_2$; or a pharmaceutically acceptable salt thereof.

In a third embodiment of the sixth aspect, the chimeric analogue comprises a compound according to the formula of:

Dop2-Lys(Dop2)-DTyr-Tyr-cyclo[DDab-Arg-Phe-Phe-DTrp-Lys-Thr-Phe],

Dop2-Tyr-cyclo[DDab-Arg-Phe-Phe-DTrp-Lys-Thr-Phe], or

Dop2-DTyr-DTyr-Caeg-cyclo[DCys-3Pal-DTrp-Lys-Dcys]-Thr(Bzl)-Tyr-NH$_2$; or a pharmaceutically acceptable salt thereof.

In a seventh aspect, the invention features a method of treating a disease or condition in a subject, said method comprising administering to said subject a therapeutically effective amount of a chimeric analog, wherein said chimeric analog comprises a compound according to the formula of Formula (I), (II), (III), (IV), (V), (VI) (VII), (VIII), (IX, or (X); any of the compounds listed in Table 1;

Dop2-DPhe-Doc-DPhe-cyclo[Cys-3ITyr-DTrp-Lys-Val-Cys]-Thr-NH$_2$,

Dop2-DPhe-Doc-DPhe-cyclo[Cys-3ITyr(Dop2)-DTrp-Lys-Val-Cys]-Thr-NH$_2$,

-continued

Val-Cys]-Thr-NH$_2$,

Ac-Lys(Dop2)-DTyr-DTyr-cyclo[Cys-Tyr-DTrp-Lys-Abu-Cys]-Thr-NH$_2$,

Ac-DLys(Dop2)-DPhe-cyclo[Cys-3ITyr-DTrp-Lys-Thr-Cys]-Thr-NH$_2$,

Dop3-DPhe-cyclo[Cys-Tyr-DTrp-Lys-Abu-Cys]-Thr-NH$_2$,

Dop4-DPhe-cyclo[Cys-Tyr-DTrp-Lys-Abu-Cys]-Thr-NH$_2$,

Dop5-DPhe-cyclo[Cys-Tyr-DTrp-Lys-Abu-Cys]-Thr-NH$_2$,

Dop2-DPhe-cyclo[Cys-3ITyr-DTrp-Lys-Thr-Cys]-Thr-NH$_2$,

Dop2-Lys(Dop2)-DPhe-cyclo[Cys-Tyr-DTrp-Lys-Abu-Cys]-Thr-NH$_2$,

Dop2-Lys(Dop2)-cyclo[Cys-Tyr-DTrp-Lys-Abu-Cys]-Thr-NH$_2$,

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$,

Dop5-Lys(Dop5)-DPhe-cyclo[Cys-Tyr-DTrp-Lys-Abu-Cys]-Thr-NH$_2$,

Dop2-DPhe-cyclo[Cys-3ITyr(Dop2)-DTrp-Lys-Val-Cys]-Thr-NH$_2$,

Dop2-Lys(Dop2)-DTyr-DTyr-cyclo[Cys-3ITyr-DTrp-Lys-Thr-Cys]-Thr-NH$_2$,

Dop2-Lys(Dop2)-DPhe-cyclo[Cys-3ITyr-DTrp-Lys-Thr-Cys]-Thr-NH$_2$,

Dop2-DLys(Dop2)-DPhe-cyclo[Cys-3ITyr-DTrp-Lys-Thr-Cys]-Thr-NH$_2$,

Dop2-Lys(Dop2)-DTyr-Tyr-cyclo[DDab-Arg-Phe-Phe-DTrp-Lys-Thr-Phe],

Dop2-Tyr-cyclo[DDab-Arg-Phe-Phe-DTrp-Lys-Thr-Phe], or

Dop2-DTyr-DTyr-Caeg-cyclo[DCys-3Pal-DTrp-Lys-Dcys]-Thr(Bzl)-Tyr-NH$_2$; or a pharmaceutically acceptable salt thereof; or intermediate compound (3), (6), (11), (14), (18), (21), (24), or (27); or an organic or inorganic salt thereof; and wherein said disease or disorder is selected from the list consisting of a neuroendocrine tumor; a vascular disease; a connective tissue disease; an immune disease; a disorder of the gastrointestinal tract, pancreas, kidney, or liver, a metabolic disease; a cachexia; cancer or a tumor of the lung, breast, prostate, liver, thyroid, blood; a musculoskeletal disorder; a panic disorder; and opioid overdose; and wherein said therapeutically effective amount is the amount effective to treat said disease or disorder in said patient.

In a first embodiment of the seventh aspect, the neuroendocrine tumor is a neuroendocrine tumor of the pituitary. In a first preferred embodiment, the neuroendocrine tumor of the pituitary is an ACTH-producing tumor. Preferably, the ACTH-producing tumor is Cushing's disease. In a second preferred embodiment, the neuroendocrine tumor of the pituitary is a growth hormone producing tumor. Preferably, the growth hormone producing tumor is acromegaly. In a third preferred embodiment, the neuroendocrine tumor of the pituitary is a prolactin-producing tumor. Preferably, the prolactin-producing tumor is a prolactinoma. In a fourth preferred embodiment, the neuroendocrine tumor of the pituitary is hyperprolactinemia or prolactinemia. In a fifth preferred embodiment, the neuroendocrine tumor of the pituitary is thyroid stimulating hormone (TSH) secreting tumor. In a sixth preferred embodiment, the neuroendocrine tumor of the pituitary is "nonfunctioning" pituitary adenoma. In a seventh preferred embodiment, the neuroendocrine tumor of the pituitary is gonadotropinoma.

In a second embodiment of the seventh aspect, the neuroendocrine tumor is carcinoid tumor. In a preferred embodiment, the carcinoid tumor causes carcinoid syndrome. In a third embodiment of the seventh aspect, the neuroendocrine tumor is glucagonoma. In a fourth embodiment of the seventh aspect, the neuroendocrine tumor is small cell lung carcinoma. In a fifth embodiment of the seventh aspect, the neuroendocrine tumor is thyroid medullary carcinoma. In a sixth embodiment of the seventh aspect, the neuroendocrine tumor is VIPoma. In a seventh embodiment of the seventh aspect, the neuroendocrine tumor is insulinoma. In an eighth embodiment of the seventh aspect, the disorder of said vascular disease is inappropriate angiogenesis. In a ninth embodiment of the seventh aspect, the disorder of said vascular disease is restenosis. In a tenth embodiment of the seventh aspect, the disorder of said vascular disease is retinopathy. In a preferred embodiment, the retinopathy is diabetic retinopathy or proliferative retinopathy. In another preferred embodiment, the retinopathy is macular degeneration, preferably, age-related macular degeneration.

In another embodiment of the seventh aspect, the connective tissue disease is scleroderma. In yet another embodiment of the seventh aspect, the immune disease is rheumatoid arthritis. In yet another embodiment of the seventh aspect, the immune disease is inflammation. In yet another embodiment of the seventh aspect, the immune disease is fibrosis. In yet another embodiment of the seventh aspect, the immune disease is Graves' opthalmopathy. In yet another embodiment of the seventh aspect, the immune disease is allograft rejection. In yet another embodiment of the seventh aspect, the disorder of the gastrointestinal tract comprises gastric acid secretion, peptic ulcers, inflammatory bowel disease (IBD), or diarrhea. In a preferred embodiment, the IBD is irritable bowel syndrome or Crohn's disease. In another preferred embodiment, the diarrhea is AIDS related or chemotherapy related or watery diarrhea syndrome. In yet another preferred embodiment, the disorder of the gastrointestinal tract is small bowel syndrome, small bowel obstruction, gastroesophageal reflux, duodenogastric reflux, *H. pylori* proliferation, or gastrointestinal bleeding.

In yet another embodiment of the seventh aspect, the metabolic disease comprises hyperlipidemia, insulin resistance, Syndrome X, obesity, diabetes, or a diabetes-related disease. In a preferred embodiment, the diabetes-related disease comprises diabetic nephropathy, diabetic neuropathy, diabetic retinopathy, or gastroparesis.

In yet another embodiment of the seventh aspect, the cachexia is cardiac cachexia, cancer cachexia, or geriatric cachexia.

In yet another embodiment of the seventh aspect, the disease or disorder comprises glioma, anorexia, hypothyroidism, Graves' disease, hyperaldeosteronism, systemic sclerosis, pancreatitis, external and internal pancreatic pseudocysts and ascites, pancreaticocutaneous fistula, nesidoblastosis, hyperinsulinism, gastrinoma, Zollinger-Ellison Syndrome, gastrointestinal hormone secreting tumor, dawn phenomenon, dumping syndrome, hyperparathyroidism, Paget's disease, polycystic ovary disease, orthostatic hypotension, postprandial hypotension, portal hypertension, angiopathy, or graft vessel bleeding.

In a first related embodiment of the aspect of the invention disclosed above, the chimeric analog comprises a SSTR-1 agonist and a dopamine receptor agonist; or a pharmaceutically acceptable salt thereof. In a first preferred embodiment, the chimeric analog further comprises a SSTR-2 agonist or a SSTR-3 agonist, or a pharmaceutically acceptable salt thereof, or both.

In a second preferred embodiment, the chimeric analog further comprises a SSTR-5 agonist, or a pharmaceutically acceptable salt thereof. In a third preferred embodiment, the chimeric analog further comprises a SSTR-2 agonist or a SSTR-3 agonist, or a pharmaceutically acceptable salt thereof.

In a more preferred embodiment, the chimeric analog comprises a SSTR-1 agonist and a dopamine receptor agonist and further comprises a SSTR-2 agonist, a SSTR-3 agonist, and a SSTR-5 agonist, or a pharmaceutically acceptable salt thereof.

In a second related embodiment of the aspect of the invention disclosed above, the chimeric analog comprises a SSTR-2 agonist and a dopamine receptor agonist; or a pharmaceutically acceptable salt thereof. In a preferred embodiment, the chimeric analog further comprises a SSTR-5 agonist, or a pharmaceutically acceptable salt thereof.

In a third related embodiment of the aspect of the invention disclosed above, the chimeric analog comprises a SSTR-3 agonist and a dopamine receptor agonist; or a pharmaceutically acceptable salt thereof.

In a fourth related embodiment of the aspect of the invention disclosed above, the chimeric analog comprises a SSTR-5 agonist and a dopamine receptor agonist; or a pharmaceutically acceptable salt thereof.

In an eighth aspect, the invention features a method of treating acromegaly in a subject in need thereof, wherein said method comprises administering to said subject a therapeutically effective amount of a chimeric analog, wherein said chimeric analog comprises a compound according to the formula of Formula (I), (II), (III), (IV), (V), (VI) (VII), (VIII), (IX), or (X); any of the compounds listed in Table 1;

Dop2-DPhe-Doc-DPhe-cyclo[Cys-3ITyr-DTrp-Lys-Val-Cys]-Thr-NH$_2$,

Dop2-DPhe-Doc-DPhe-cyclo[Cys-3ITyr(Dop2)-DTrp-Lys-Val-Cys]-Thr-NH$_2$,

Ac-Lys(Dop2)-DTyr-DTyr-cyclo[Cys-Tyr-DTrp-Lys-Abu-Cys]-Thr-NH$_2$,

Ac-DLys(Dop2)-DPhe-cyclo[Cys-3ITyr-DTrp-Lys-Thr-Cys]-Thr-NH$_2$,

Dop3-DPhe-cyclo[Cys-Tyr-DTrp-Lys-Abu-Cys]-Thr-NH$_2$,

Dop4-DPhe-cyclo[Cys-Tyr-DTrp-Lys-Abu-Cys]-Thr-NH$_2$,

Dop5-DPhe-cyclo[Cys-Tyr-DTrp-Lys-Abu-Cys]-Thr-NH$_2$,

Dop2-DPhe-cyclo[Cys-3ITyr-DTrp-Lys-Thr-Cys]-Thr-NH$_2$,

Dop2-Lys(Dop2)-DPhe-cyclo[Cys-Tyr-DTrp-Lys-Abu-Cys]-Thr-NH$_2$,

Dop2-Lys(Dop2)-cyclo[Cys-Tyr-DTrp-Lys-Abu-Cys]-Thr-NH$_2$,

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$,

Dop5-Lys(Dop5)-DPhe-cyclo[Cys-Tyr-DTrp-Lys-Abu-Cys]-Thr-NH$_2$,

Dop2-DPhe-cyclo[Cys-3ITyr(Dop2)-DTrp-Lys-Val-Cys]-Thr-NH$_2$,

Dop2-Lys(Dop2)-DTyr-DTyr-cyclo[Cys-3ITyr-DTrp-Lys-Thr-Cys]-Thr-NH$_2$,

Dop2-Lys(Dop2)-DPhe-cyclo[Cys-3ITyr-DTrp-Lys-Thr-Cys]-Thr-NH$_2$,

Dop2-DLys(Dop2)-DPhe-cyclo[Cys-3ITyr-DTrp-Lys-Thr-Cys]-Thr-NH$_2$,

Dop2-Lys(Dop2)-DTyr-Tyr-cyclo[DDab-Arg-Phe-Phe-DTrp-Lys-Thr-Phe],

Dop2-Tyr-cyclo[DDab-Arg-Phe-Phe-DTrp-Lys-Thr-Phe], or

Dop2-DTyr-DTyr-Caeg-cyclo[DCys-3Pal-DTrp-Lys-Dcys]-Thr(Bzl)-Tyr-NH$_2$; or a pharmaceutically acceptable salt thereof; or intermediate compound (3), (6), (11), (14), (18), (21), (24), or (27); or an organic or inorganic salt thereof; and the therapeutically effective amount is the amount effective to treat acromegaly in said patient. In a preferred embodiment of this aspect of the invention, the chimeric analog comprises a SSTR-5 agonist and a dopamine receptor agonist. More preferably, the chimeric analog further comprises a SSTR-2 agonist.

In another preferred embodiment of this aspect, the subject has developed or is at risk of developing acromegaly.

In a ninth aspect, the invention features a method of treating prolactinemia in a subject in need thereof, wherein said method comprises administering to said subject a therapeutically effective amount of a chimeric analog, wherein said chimeric analog comprises a compound according to the formula of Formula (I), (II), (III), (IV), (V), (VI) (VII), (VIII), (IX), or (X); any of the compounds listed in Table 1;

Dop2-DPhe-Doc-DPhe-cyclo[Cys-3ITyr-DTrp-Lys-Val-Cys]-Thr-NH$_2$,

Dop2-DPhe-Doc-DPhe-cyclo[Cys-3ITyr-(Dop2)-DTrp-Lys-Val-Cys]-Thr-NH$_2$,

Ac-Lys(Dop2)-DTyr-DTyr-cyclo[Cys-Tyr-DTrp-Lys-Abu-Cys]-Thr-NH$_2$,

Ac-DLys(Dop2)-DPhe-cyclo[Cys-3ITyr-DTrp-Lys-Thr-Cys]-Thr-NH$_2$,

Dop3-DPhe-cyclo[Cys-Tyr-DTrp-Lys-Abu-Cys]-Thr-NH$_2$,

Dop4-DPhe-cyclo[Cys-Tyr-DTrp-Lys-Abu-Cys]-Thr-NH$_2$,

Dop5-DPhe-cyclo[Cys-Tyr-DTrp-Lys-Abu-Cys]-Thr-NH$_2$,

Dop2-DPhe-cyclo[Cys-3ITyr-DTrp-Lys-Thr-Cys]-Thr-NH$_2$,

Dop2-Lys(Dop2)-DPhe-cyclo[Cys-Tyr-DTrp-Lys-Abu-Cys]-Thr-NH$_2$,

Dop2-Lys(Dop2)-cyclo[Cys-Tyr-DTrp-Lys-Abu-Cys]-Thr-NH$_2$,

Dop2-Lys(Dop2)-DTyr-DTyr-cyclo[Cys-Tyr-DTrp-Lys-Abu-Cys]-Thr-NH$_2$,

Dop2-DLys(Dop2)-cyclo[Cys-Tyr-DTrp-Lys-Abu-Cys]-Thr-NH$_2$,

Dop5-Lys(Dop5)-DPhe-cyclo[Cys-Tyr-DTrp-Lys-Abu-Cys]-Thr-NH$_2$,

Dop2-DPhe-cyclo[Cys-3ITyr(Dop2)-DTrp-Lys-Val-Cys]-Thr-NH$_2$,

Dop2-Lys(Dop2)-DTyr-DTyr-cyclo[Cys-3ITyr-DTrp-Lys-Thr-Cys]-Thr-NH$_2$,

Dop2-Lys(Dop2)-DPhe-cyclo[Cys-3ITyr-DTrp-Lys-Thr-Cys]-Thr-NH$_2$,

Dop2-DLys(Dop2)-DPhe-cyclo[Cys-3ITyr-DTrp-Lys-Thr-Cys]-Thr-NH$_2$,

Dop2-Lys(Dop2)-DTyr-Tyr-cyclo[DDab-Arg-Phe-Phe-DTrp-Lys-Thr-Phe],

Dop2-Tyr-cyclo[DDab-Arg-Phe-Phe-DTrp-Lys-Thr-Phe], or

Dop2-DTyr-DTyr-Caeg-cyclo[DCys-3Pal-DTrp-Lys-Dcys]-Thr(Bzl)-Tyr-NH$_2$, or a pharmaceutically acceptable salt thereof; or intermediate compound (3), (6), (11), (14), (18), (21), (24), or (27); or an organic or inorganic salt thereof; and the therapeutically effective amount is the amount effective to treat prolactinemia in said patient. In a preferred embodiment of this aspect of the invention, the chimeric analog comprises a SSTR-5 agonist and a dopamine receptor agonist More preferably, the chimeric analog further comprises a SSTR-2 agonist.

In another preferred embodiment of this aspect, the subject has developed or is at risk of developing prolactinemia.

In some embodiments, compounds of the invention may include the structure of DopA-Lys(DopA), wherein Lys is L-lysine, unless expressly designated as DLys. A is 1-13, for example, Dop1, Dop2, Dop3, Dop4, Dop5, Dop6, Dop7, Dop8, Dop9, Dop10, Dop11, Dop12, and Dop13. The structure of a DopA-Lys(DopA), in which A is 2 (i.e., Dop2-Lys(Dop2)), and in which A is 5 (i.e., Dop5-Lys(Dop5)), are shown below.

By "Dop1" is meant a compound having the structure of:

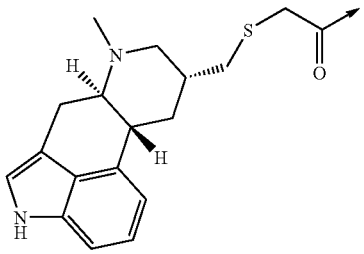

By "Dop2" is meant a compound having the structure of:

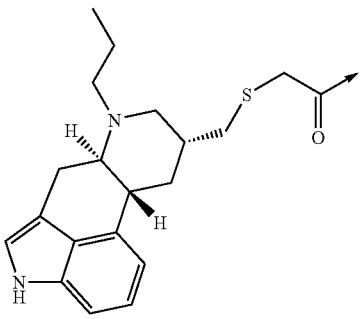

By "Dop3" is meant a compound having the structure of:

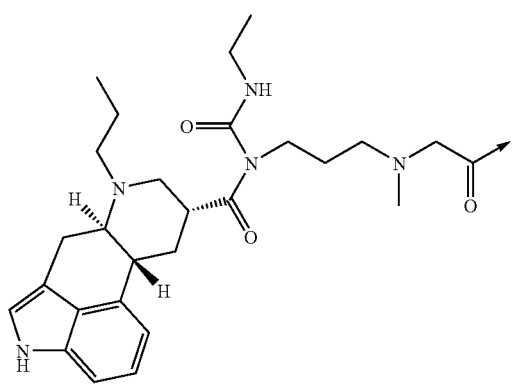

By "Dop4" is meant a compound having the structure of:

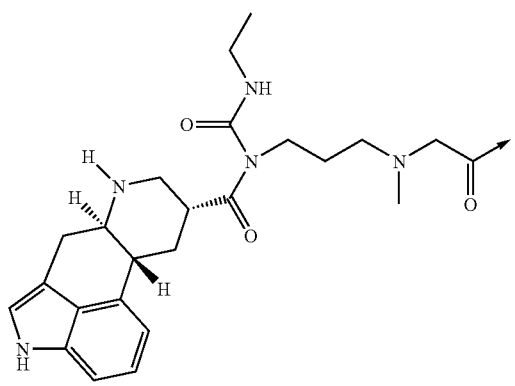

By "Dop5" is meant a compound having the structure of:

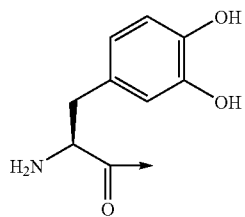

By "Dop6" is meant a compound having the structure of:

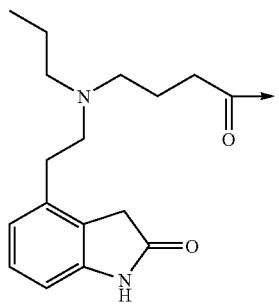

By "Dop7" is meant a compound having the structure of:

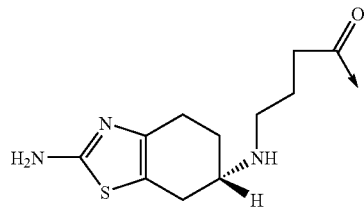

By "Dop8" is meant a compound having the structure of:

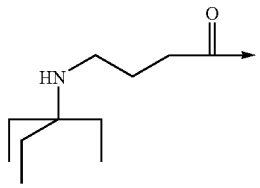

By "Dop9" is meant a compound having the structure of:

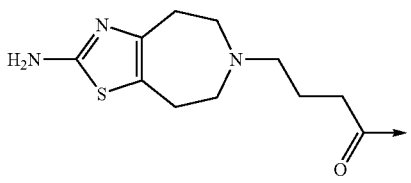

By "Dop10" is meant a compound having the structure of:

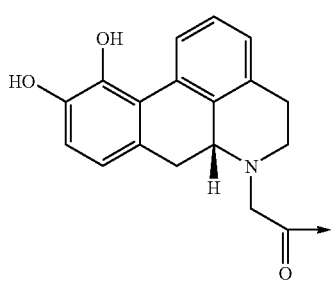

By "Dop11" is meant a compound having the structure of:
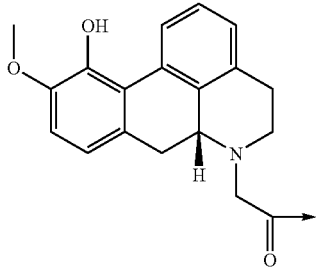
By "Dop12" is meant a compound having the structure of:
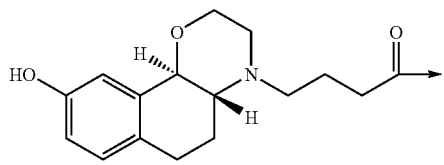
By "Dop13" is meant a compound having the structure of:
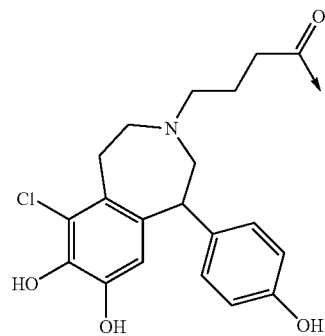
Lys(Dop2) has the structure of:
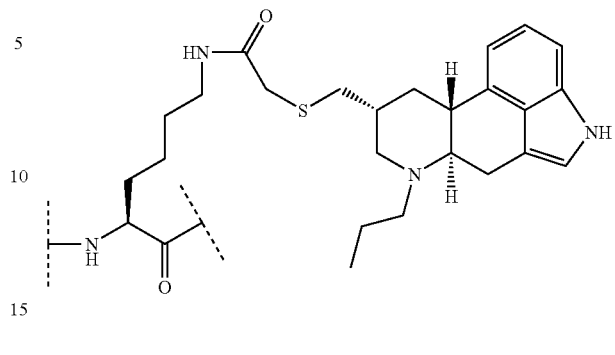
Dop2-Lys(Dop2) has the structure of:
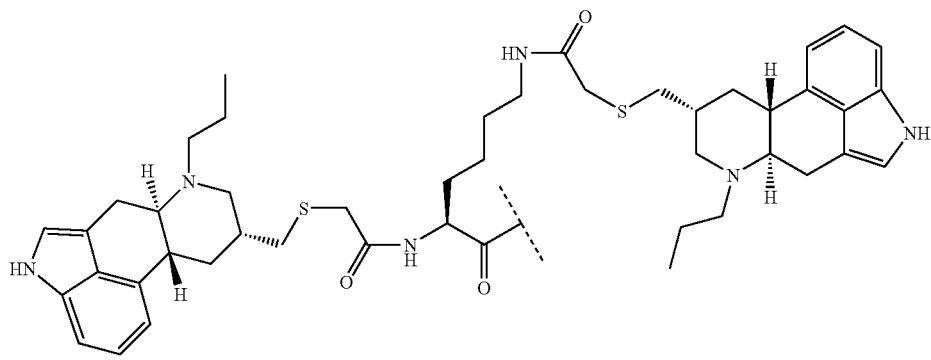
Lys(Dop5) has the structure of:
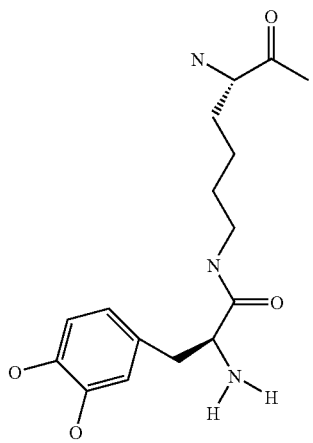

Dop5-Lys(Dop5) has the structure of:

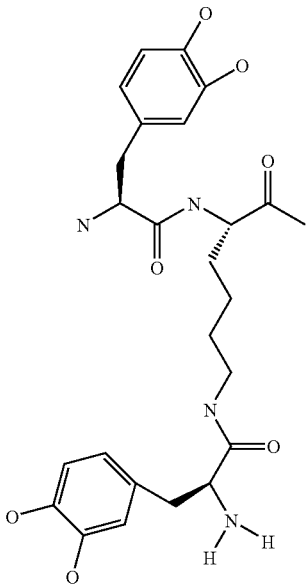

By "Alkyl" is meant a hydrocarbon group containing one or more carbon atoms, where multiple carbon atoms if present are joined by single bonds. The alkyl hydrocarbon group may be straight-chain or contain one or more branches or cyclic groups.

By "Substituted alkyl" is meant an alkyl wherein one or more hydrogen atoms of the hydrocarbon group are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-2}$ alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present. The presence of —(CH$_2$)$_{0-4}$—COOH results in the production of an alkyl acid. Examples of alkyl acids containing, or consisting of, —(CH$_2$)$_{0-4}$—COOH include 2-norbornane acetic acid, tert-butyric acid and 3-cyclopentyl propionic acid.

By "Heteroalkyl" is meant an alkyl wherein one of more of the carbon atoms in the hydrocarbon group are replaced with one or more of the following groups: amino, amido, —O—, or carbonyl. In different embodiments 1 or 2 heteroatoms are present.

By "Substituted heteroalkyl" is meant a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, —C$_{1-2}$ alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "Alkenyl" is meant a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl where one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, —C$_{1-2}$ alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "Alkynyl" is meant to a hydrocarbon group made up of two or more carbons where one or more carbon-carbon triple bonds are present. The alkynyl hydrocarbon group may be straight-chain or contain one or more branches or cyclic groups.

By "Substituted alkynyl" is meant an alkynyl where one or more hydrogens are replaced with one or more substituents selected from the group consisting of a halogen (i.e., fluorine, chlorine, bromine, and iodine), —OH, —CN, —SH, —NH$_2$, —NHCH$_3$, —NO$_2$, —C$_{1-2}$ alkyl substituted with 1 to 5 halogens, —CF$_3$, —OCH$_3$, —OCF$_3$, and —(CH$_2$)$_{0-4}$—COOH. In different embodiments 1, 2, 3 or 4 substituents are present.

By "Aryl" is meant an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring. Preferred atoms for a heterocyclic aryl are one or more sulfur, oxygen, and/or nitrogen. Examples of aryl include phenyl, 1-naphthyl, 2-naphthyl, indole, quinoline, 2-imidazole, and 9-anthracene. Aryl substituents are selected from the group consisting of —C$_{1-4}$ alkyl, —C$_{1-4}$ alkoxy, halogen (i.e., fluorine, chlorine, bromine, and iodine), —OH, —CN, —SH, —NH$_2$, —NO$_2$, —C$_{1-2}$ alkyl substituted with 1 to 5 halogens, —CF$_3$, —OCF$_3$, and —(CH$_2$)$_{0-4}$—COOH. In different embodiments the aryl contains 0, 1, 2, 3, or 4 substituents.

By "Acyl" is meant X'—R"—C(O)—, where R" is alkyl, substituted alkyl, heteroalkyl, substituted heteroalkyl, alkenyl, substituted alkenyl, alkynyl, substituted alkynyl, aryl, alkylaryl, or substituted alklyaryl and X' is H or absent.

By "Arylalkyl" or "alkylaryl" is meant an "alkyl" joined to an "aryl".

By "Abu" is meant α-aminobutyric acid.

By "Aepa" is meant 4-(2-aminoethyl)-1-carboxy methyl-piperazine, represented by the structure:

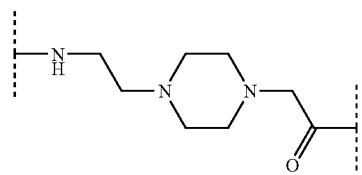

By "Aib" is meant α-aminoisobutyric acid.

By "Ala" or "A" is meant alanine.

By "β-Ala" is meant beta-alanine.

By "Arg" or "R" is meant arginine.

By "Asn" or "N" is meant asparagines.

By "Asp" or "D" is meant aspartic acid.

By "Caeg" is meant N-(2-aminoethyl)-N-(2-cytosinyl-1-oxo-ethyl)-glycine, represented by the structure:

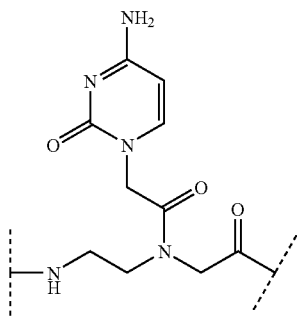

By "Cys" or "C" is meant cysteine.
By "Dab" is meant 2,4-diaminobutyric acid.
By "Doc" is meant 8-amino-3,6-dioxaoctanoic acid, represented by the structure

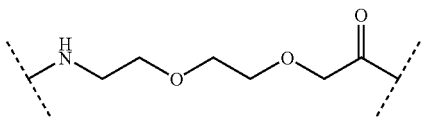

By "Gln" or "Q" is meant glutamine.
By "Glu" or "E" is meant glutamic acid.
By "Gly" or "G" is meant glycine.
By "His" or "H" is meant histidine.
By "Ile" or "I" is meantisoleucine.
By "Leu" or "L" is meant leucine.
By "Lys" or "K" is meant lysine.
By "Met" or "M" is meant methionine.
By "1Nal" is meant β-(1-naphthyl)alanine.
By "2Nal" is meant β-(2-naphthyl)alanine.
By "Nle" is meant norleucine.
By "Orn" is meant ornithine.
By "2Pal" is meant β-(2-pyridinyl)alanine.
By "3Pal" is meant β-(3-pyridinyl)alanine.
By "4Pal" is meant β-(4-pyridinyl)alanine.
By "Phe" or "F" is meant phenylalanine.
By "Pro" or "P" is meant proline.
By "Ser" or "S" is meant serine.
By "Thr" or "T" is meant threonine.
By "Thr-ol" is meant threoninol, represented by the structure:

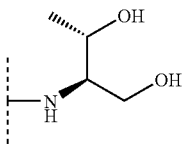

By "Val" or "V" is meant valine.
By "(N-Me)Trp" is meant N-α-methyl-trptophan.
Certain other abbreviations used herein are defined as follows:
By "Ac" is meant acetyl.
By "Boc" is meant tert-butyloxycarbonyl.
By "Bzl" is meant benzyl.
By "DCM" is meant dichloromethane.
By "DIC" is meant N,N-diisopropylcarbodiimide.
By "DIEA" is meant diisopropylethyl amine.
By "Dmab" is meant 4-{N-(1-(4,4-dimethyl-2,6-dioxocyclohexylidene)-3-methylbutyl)-amino}benzyl.
By "DMAP" is meant 4-(dimethylamino)pyridine.
By "DMF" is meant dimethylformamide.
By "DNP" is meant 2,4-dinitrophenyl.
By "Fmoc" is meant Fluorenylmethyloxycarbonyl.
By "HBTU" is meant 2-(1H-benzotriazole-1-yl)-1,1,3,3-tetramethyluronium hexafluorophosphate.
By "cHex" is meant cyclohexyl.
By "HOAT" is meant O-(7-azabenzotriazol-1-yl)-1,1,3,3-tetramethyluronium hexafluorophosphate.
By "HOBt" is meant 1-hydroxy-benzotriazole.
By "Mmt" is meant 4-methoxytrityl.
By "NMP" is meant N-methylpyrrolidone.
By "Pbf" is meant 2,2,4,6,7-pentamethyldihydrobenzofuran-5-sulfonyl.
By "tBu" is meant tert-butyl.
By "TIS" is meant triisopropylsilane.
By "TOS" is meant tosyl.
By "trt" is meant trityl.
By "TFA" is meant trifluoro acetic acid.
By "TFFH" is meant tetramethylfluoroforamidinium hexafluorophosphate.
By a "somatostatin receptor agonist" is meant a compound that has a high binding affinity (e.g., Ki of less than 100 nM, or preferably less than 10 nM, or more preferably less than 1 nM) for a somatostatin receptor (e.g., as defined by the receptor binding assay described below), such as any of the different subtypes: e.g., SSTR-1, SSTR-2, SSTR-3, SSTR-4, and SSTR-5, and elicits a somatostatin-like effect; for example, in an assay for the inhibition of cAMP intracellular production.
By a "somatostatin selective agonist" is meant a somatostatin receptor agonist which has a higher binding affinity (i.e., lower Ki) for one somatostatin receptor subtype than for any other somatostatin receptor subtype, such as, for example, a somatostatin SSTR-2 selective agonist.
By a "dopamine receptor agonist" is meant a compound that has a high binding affinity (e.g., Ki of less than 100 nM, or preferably less than 10 nM, or more preferably less than 1 nM) for a dopamine receptor (e.g., as defined by the receptor binding assay described below), such as any of the different subtypes: e.g., D1, D2, D3, D4, and D5 receptors.

DETAILED DESCRIPTION

The invention features somatostatin-dopamine chimeric analogs and methods relating to their therapeutic use for the treatment of neoplasia, acromegaly, and other conditions.
Various somatostatin receptors (SSTR's) have been isolated (e.g., SSTR-1, SSTR-2, SSTR-3, SSTR-4, and SSTR-5). Somatostatin agonists are those compounds that bind to at least one SSTR (e.g., SSTR-1 agonist, SSTR-2 agonist, SSTR-3 agonist, SSTR-4 agonist or a SSTR-5 agonist).
Further examples of somatostatin agonists are those covered by formulae or those specifically recited in the publications set forth below, each of which is hereby incorporated by reference in its entirety.
PCT Application No. WO 03/057214 (2003)
U.S. Application No. 20030191134 (2003)
U.S. Application No. 20030083241 (2003)
PCT Application No. 0210215 (2002)
U.S. Pat. No. 6,316,414 (2001)
PCT Application No. WO 99/22735 (1999)
PCT Application No. WO 98/08100 (1998)
PCT Application No. WO 98/44921 (1998)
PCT Application No. WO 98/45285 (1998)
PCT Application No. WO 98/44922 (1998)

EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13-19, 1992, Interlaken, Switzerland;
PCT Application No. WO 91/09056 (1991);
EP Application No. 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Note that for all somatostatin agonists described herein, each amino acid residue represents the structure of —NH—C(R)H—CO—, in which R is the side chain (e.g., $CH_3$ for Ala). Lines between amino acid residues represent peptide bonds that join the amino acids. Also, where the amino acid residue is optically active, it is the L-form configuration, unless the D-form is expressly designated. For clarity, disulfide bonds (e.g., disulfide bridge) that exist between two free thiols of Cys residues are not shown. Abbreviations of the common amino acids are in accordance with IUPAC-IUB recommendations.

Synthesis of Somatostatin Agonists

The methods for synthesizing peptide somatostatin agonists are well documented and are within the ability of a person of ordinary skill in the art. For example, peptides are synthesized on Rink amide MBHA resin (4-(2'4'-dimethoxyphenyl-Fmoc-aminomethyl)-phenoxyacetamido-norleucyl-MBHA resin) using a standard solid phase protocol of Fmoc chemistry. The peptide-resin with free amino functional at the N-terminus is then treated with the corresponding compound containing dopamine moiety. The final product is cleaved off from resin with TFA water/triisopropylsilane (TIS) mixture.

For example, synthesis of H-D-Phe-Phe-Phe-D-Trp-Lys-Thr-Phe-Thr-$NH_2$, can be achieved by following the protocol set forth in Example I of European Patent Application 0 395 417 A1. The synthesis of somatostatin agonists with a substituted N-terminus can be achieved, for example, by following the protocol set forth in PCT Publication No. WO 88/02756, PCT Publication No., WO 94/04752, and/or European Patent Application No. 0 329 295.

Peptides can be and were cyclized by using iodine solution in MeOH/water and purified on C18 reverse-phase preparative HPLC, using acetonitrile-0.1% TFA/water-0.1% TFA buffers. Homogeneity was assessed by analytical HPLC and mass spectrometry and determined to be >95% for each peptide.

Certain uncommon amino acids were purchased from the following vendors: Fmoc-Doc-OH and Fmoc-AEPA-OH were purchased from Chem-Impex International, Inc. (Wood Dale, Ill., USA). Fmoc-Caeg (Bhoc)-OH was purchased from PerSeptive Biosystems (Framingham, Mass., USA). Bhoc stands for benzhydryloxycarbonyl.

Synthesis of Dopamine Agonists

The methods for synthesizing many dopamine agonists are also well documented and are within the ability of a person of ordinary skill in the art. Further synthetic procedures are provided in the reaction schemes and examples as shown in FIGS. 1-A to 1-M.

Synthesis of Somatostatin-Dopamine Chimers

Somatostatin-dopamine chimers may be synthesized according to the following reaction schemes and examples. Starting material and intermediates for such compounds are commercially available or are prepared using standard methods, e.g., see Pharmazie 39, 537 (1984); collect Czech. Chem. Commun. 33, 577 (1966); Helv. Chim. Acta 32, 1947, (1949), U.S. Pat. No. 5,097,031; U.S. Pat. No. 3,901,894; EP 0003667; and U.S. Pat. No. 4,526,892. Methods for the synthesis of peptides are known to the skilled artisan (e.g., see Stewart et al., Solid Phase Synthesis, Pierce Chemical, $2^{nd}$ Ed. 1984; G. A. Grant; Synthetic peptide; WH., Freenand Co., New York, 1992; M. Bodenszky A. Bodansky, The Practice of Peptide Synthesis, Spring Venlag. N.Y. 1984).

Other somatostatin-dopamine chimers that suppress growth hormone and prolactin secretion and are useful in the treatment of acromegaly are described in Saveanu et al. (J. Clin. Endocrin. and Metab. 87:5545-5552, 2002), hereby incorporated by reference.

The following examples are provided to illustrate the invention. They are not meant to limit the invention in any way.

EXAMPLE 1

Dop2-DLys(Dop2)-DPhe-cyclo[Cys-3ITyr-DTrp-Lys-Thr-Cys]-Thr-$NE_2$

The Dop2-DLys(Dop2)-DPhe-cyclo[Cys-3ITyr-DTrp-Lys-Thr-Cys]-Thr-$NH_2$ peptide was automatically synthesized on an ACT 396 peptide synthesizer (Advanced ChemTech, Louisville, Ky.) using Fluorenylmethyloxycarbonyl (Fmoc) chemistry. A RINK AMIDE 4-methylbenzylhydrylamine (MBHA) resin (Novabiochem., San Diego, Calif.) with substitution of 0.66 mmol/g was used (sub: 0.66 mmol/g, 76 mg, 50 µmol scale). The Fmoc amino acids used are Fmoc-DTrp(Boc)-OH, Fmoc-Lys(Boc)-OH, Fmoc-Thr(But)-OH, Fmoc-DPhe-OH, Fmoc-Cys(Trt)-OH, and Fmoc-DLys(Dde))-OH from NOVABIOCHEM (San Diego, Calif.) and Fmoc-3ITyr-OH from CHEM-IMPEX INTERNATIONAL, Inc. (Wood Dale, Ill.). The synthesis was carried out on a 50 µmol scale. For each reaction cycle, the ACT 396 peptide synthesizer was programmed to perform: (1) washing with N-methylpyrrolidone (NMP) twice; (2) removing Fmoc protecting group with 20% piperidine in NMP for 1×5 min and 1×25 min; (3) washing with NMP twice; and (4) double coupling with 4× fold excess of Fmoc protected amino acid (0.20 mmol), HOBt (0.2 mmol), and N,N'-diisopropylcarbodiimide (DIC) (0.2 mmol) in N,N-dimethylformamide (DMF) for 1 hour per coupling. The resin was coupled successively according to the sequence.

After the peptide chain was assembled, the Fmoc group was removed and the resin was washed completely using NMP and dichloromethane (DCM). The resin was transferred into a reaction vessel on a shaker and treated with 2% hydrozine in DMF for 2×30 minutes to remove Dde protecting group in the side chain of DLys. After washing successively with DMF, MeOH and DCM, the resin was shaken overnight with Dop2-OH (54 mg, 3.0 eq), bromo-tris-pyrrolidino-phosphonium hexafluorophosphate (PyBrop, 82 mg, 3.4 eq), 1-hydroxy-7-azabenzotriazole (HOAT, 0.4 mg, 3.0 eq), pentalflurophenol (18.4 mg, 4 eq), DMAP (0.25 mL of 0.1 M in DMF, 1.0 eq) and diisopropylethyl amine (DIEA) (53 µL, 4 eq).

After washing successively with DMF, MeOH and DCM, the resin was treated with a mixture of TFA (4.75 mL), $H_2O$ (0.4 mL), and triisopropylsilane (TIS, 0.425 mL) for 2 hours. The resin was removed by filtration. The filtrate was poured into 70 mL of ether. The precipitate formed was filtered off and washed thoroughly with ether. This crude product was dissolved in 5 mL of aqueous acetic acid solution (water/acetic acid=1:1). The solution was then diluted with 50 mL of $H_2O$ and 20 mL of acetonitrile, to which was added, dropwise, iodine in methanol until the solution acquired a sustained yellow hue. The solution was stirred slowly for 1 hour and the reaction was terminated by adding aqueous $Na_2S_2O_3$ solution. The crude product was purified on reverse-phase preparative HPLC using a column of C18 DYNAMAX-100A° (4×43 cm, Varian, Walnut Creek, Calif.). The column was eluted with a liner gradient from 90% A and 10% B to 60% A and 40% B in an hour where A was 0.1% TFA in water and B was 0.1% TFA in acetonitrile. Fractions containing a major component by ultraviolet (UV) absorption were pooled and lyophilized. The purity was 95.7% based on an analytical HPLC analysis. Electro-spray ionization mass spectrometry (ESI mass) analysis gave the molecular weight at 1982.6 (in agreement with the calculated molecular weight of 1983.3).

EXAMPLE 2

Dop2-DPhe-Doc-DPhe-cyclo[Cys-3ITyr(Dop2)-DTrp-Lys-Val-Cys]-Thr-$NH_2$

The Dop2-DPhe-Doc-DPhe-cyclo[Cys-3ITyr(Dop2)-DTrp-Lys-Val-Cys]-Thr-$NH_2$ compound was synthesized substantially according to the procedure described for the synthesis of Dop2-DLys(Dop2)-DPhe-cyclo[Cys-3ITyr-DTrp-Lys-Thr-Cys]-Thr-$NH_2$ (as described above in Example 1) with the following changes. After the assembly of the peptide chain, the resin was transferred into a reaction vessel on a shaker and treated with 25% piperidine in DMF for 30 minutes to remove the Fmoc protecting group at the N-terminus. After washing successively with DMF, MeOH and DCM, the resin was shaken overnight with Dop2-OH (3.0 eq), PyBrop (3.4 eq), HOAT (3.0 eq), DMAP (1.0 eq) and DIEA (4 eq). After cleavage and purification, the desired product was found to have a purity of 95% based on an analytical HPLC analysis. ESI mass analysis gave the molecular weight at 2145.9 (in agreement with the calculated molecular weight of 2145.6).

EXAMPLE 3

Dop2-Lys(Dop2)-DTyr-DTyr-cyclo[Cys-Tyr-DTrp-Lys-Abu-Cys]-Thr-$NH_2$

The titled compound was synthesized substantially according to the procedure described for the synthesis of Dop2-DPhe-Doc-DPhe-c[Cys-3ITyr(Dop2)-DTrp-Lys-Val-Cys]-Thr-$NH_2$ (described above in Example 2) except that Fmoc-Lys(Fmoc)-OH was used for the coupling of the last Lys residue at the N-terminus. The product was found to be homogenous and the purity was 93.9% by HPLC. ESI mass-analysis gave the molecular weight at 2020.9 (in agreement with the calculated molecular weight of 2020.1).

EXAMPLE 4

Dop2-DPhe-cyclo[Cys-3ITyr-DTrp-Lys-Thr-Cys]-Thr-$NH_2$

The titled compound was synthesized substantially according to the procedure described for the synthesis of Dop2-DPhe-Doc-DPhe-c[Cys-3ITyr(Dop2)-DTrp-Lys-Val-Cys]-Thr-$NH_2$ (described above in Example 1). The purity of the final product was 93.9% based on an analytical HPLC analysis. ESI mass analysis gave the molecular weight at 1514.50 (in agreement with the calculated molecular weight of 1514.63).

EXAMPLE 5

Synthesis of Intermediate Compound (3) as shown in FIG. 2

A mixture of R(−)norapomorphine compound 1 (from Sigma, 200 mg, 0.79 mmol) and p-toluenesulfonic acid monohydrate (451 mg, 2.37 mmol) in acetone (20 mL) is stirred at room temperature overnight. The solvent is removed under reduced pressure. The residue is dissolved in methylene chloride (30 mL) and washed with saturated $NaHCO_3$ aqueous solution (2 times) and brine (2 times), dried over anhydrous $MgSO_4$, filtered, and concentrated in vacuo. The residue is purified by using column chromatography on silica, yielding acetonide-R(−)norapomorphine, yielding compound 2.

To a mixture of compound 2 (167 mg, 0.57 mmol) and N,N-diisopropylethylamine (219 mg, 1.7 mmol) in methylene chloride (20 mL) is added dropwise bromoacetic acid (236 mg, 1.7 mmol) at 0° C. The mixture is then warmed to room temperature and stirred for 6 hours. The solution is washed with brine (2 times), dried over anhydrous $MgSO_4$, filtered, and concentrated in vacuo. The residue is purified by using column chromatography on silica, yielding intermediate compound 3.

EXAMPLE 6

Figure 3:
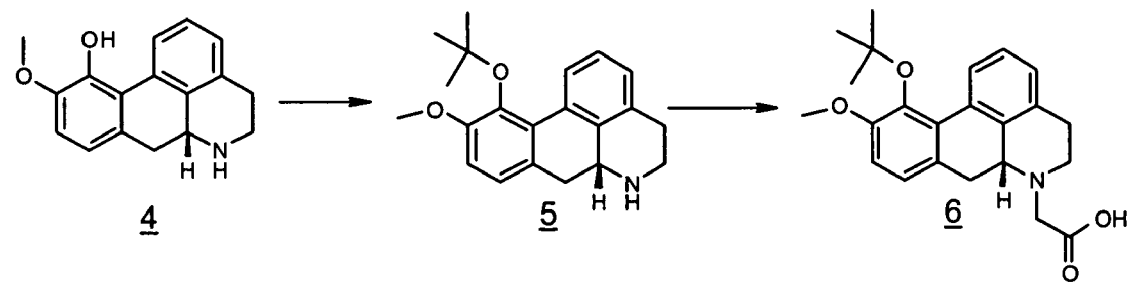

Synthesis of Intermediate Compound (6) as shown in FIG. 3

The mixture of R(-)norapomorphine 4 (200 mg, 0.748 mmol), 2-methylpropene (83.9 mg, 1.50 mmol), and a catalytic amount of concentrated $H_2SO_4$ in $CH_2Cl_2$ (20 mL) is stirred at room temperature overnight. The solution is washed with saturated $NaHCO_3$ in aqueous solution (2 times) and brine (2 times), dried over anhydrous $MgSO_4$, filtered, and concentrated in vacuo. The residue is purified by using column chromatography on silica, yielding compound 5.

To a mixture of compound 5 (150 mg, 0.486 mmol) and N,N-diisopropylethylamine (188 mg, 1.46 mmol) in methylene chloride (20 mL) is added dropwise bromoacetic acid (203 mg, 1.46 mmol) at 0° C. The mixture is then warmed to room temperature and stirred for 6 hours. The solution is washed with brine (2 times) and dried over anhydrous $MgSO_4$, filtered, and concentrated in vacuo. The residue is purified by using column chromatography on silica, yielding intermediate compound 6.

EXAMPLE 7

Figure 4:
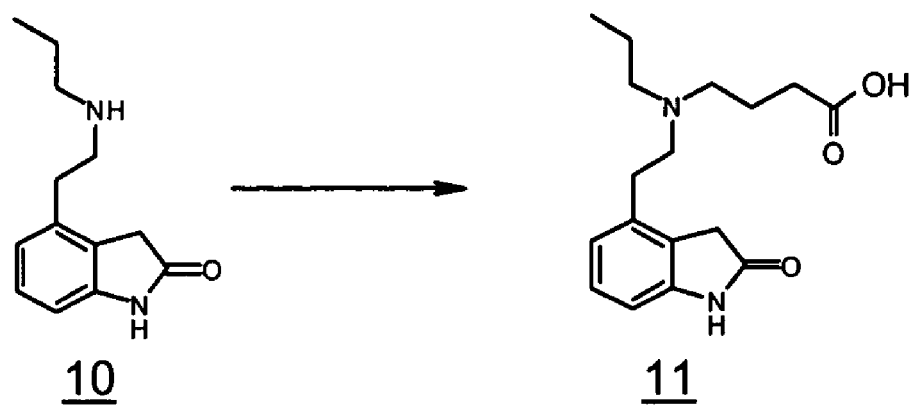

Synthesis of Intermediate Compound (11) as shown in FIG. 4

To a mixture of indolone 10 (WO 9415918, 218 mg, 1.00 mmol) and N,N-diisopropylethylamine (258 mg, 2.0 mmol) in methylene chloride (20 mL) is added 4-iodobutyric acid (214 mg, 1.0 mmol). The resulting solution is stirred at room temperature overnight. The solution is concentrated in vacuo. The residue is purified by using column chromatography on silica, yielding intermediate compound 11.

EXAMPLE 8

Figure 5:
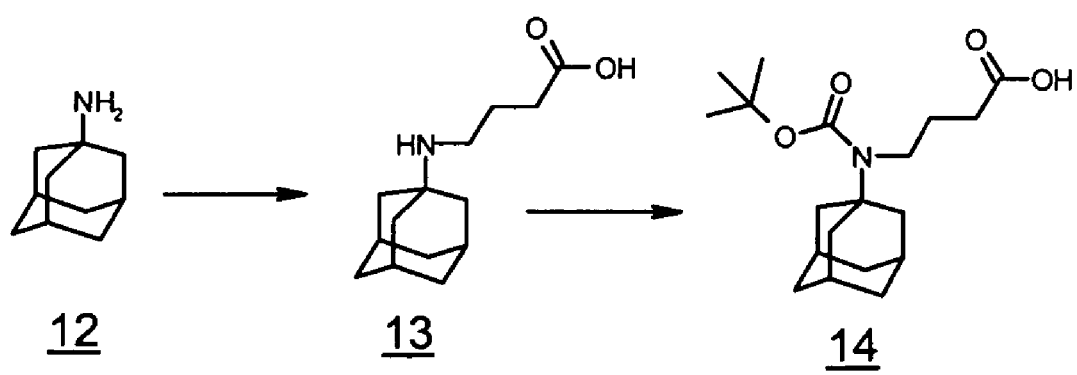

Synthesis of Intermediate Compound (14) as shown in FIG. 5

To a mixture of 1-adamantanamine hydrochloride 12 (Aldrich, 187 mg, 1.00 mmol) and N,N-diisopropylethylamine (387 mg, 3.0 mmol) in methylene chloride (20 mL) is added 4-iodobutyric acid (214 mg, 1.0 mmol). The resulting solution is stirred at room temperature overnight. The solution is washed with brine (2 times), dried over anhydrous $MgSO_4$, filtered, and concentrated in vacuo. The residue is purified by using column chromatography on silica, yielding compound 13.

To a solution of compound 13 (190 mg, 0.8 mmol) in dioxane (6 mL) and water (3 mL) is added 1N NaOH (1.0 mL) at 0° C. To the resulting solution is added di-tert-butyl dicarbonate (192 mg, 0.88 mmol) over 30 min. The mixture is stirred at room temperature for 12 hours. Dioxane is removed under reduced pressure. To the resulting water solution is added ethyl acetate. The pH of the solution is adjusted to about pH 3 by adding 0.2 N HCl solution at 0° C. The organic layer is separated, washed with water (twice), dried over anhydrous $MgSO_4$, filtered, and concentrated in vacuo. The residue is purified by using column chromatography on silica, yielding intermediate compound 14.

EXAMPLE 9

Figure 6:
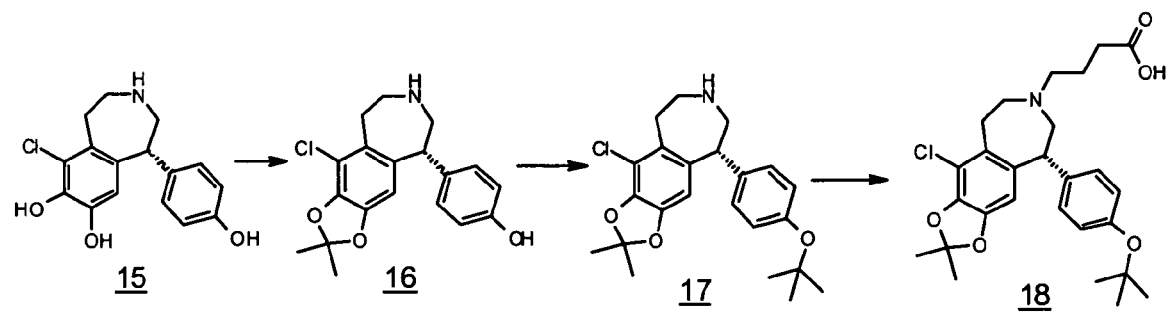

Synthesis of Intermediate Compound (18) as shown in FIG. 6

The mixture of fenoldopam 15 (from Sigma, 306 mg, 1.00 mmol) and p-toluenesulfonicacid monohydrate (476 mg, 2.50 mmol) in acetone (30 mL) is stirred at room temperature overnight. The solvent is removed under reduced pressure. The residue is dissolved in methylene chloride (30 mL) and washed with saturated $NaHCO_3$ aqueous solution (2 times) and brine (2 times), dried over anhydrous $MgSO_4$, filtered, and concentrated in vacuo. The residue is purified by using column chromatography on silica, yielding acetonide-fenoldopam 16.

A mixture of acetonide-fenoldopam 16 (277 mg, 0.80 mmol), 2-methylpropene (67.0 mg, 1.20 mmol), and a catalytic amount of concentrated $H_2SO_4$ in $CH_2Cl_2$ (20 mL) is stirred at room temperature overnight. The solution is washed with saturated $NaHCO_3$ aqueous solution (2 times) and brine (2 times) and dried over anhydrous $MgSO_4$, filtered and concentrated in vacuo. The residue is purified by using column chromatography on silica, yielding compound 17.

To a mixture of 17 (201 mg, 0.50 mmol) and *N,N-diisopropylethylamine (129 mg, 1.0 mmol) in methylene chloride (20 mL) is added 4-iodobutyric acid (107 mg, 0.5 mmol). The resulting solution is stirred at room temperature overnight. The solution is washed with brine (2 times), dried over anhydrous $MgSO_4$, filtered and concentrated in vacuo. The residue is purified by using column chromatography on silica, yielding intermediate compound 18.

EXAMPLE 10

Figure 7:
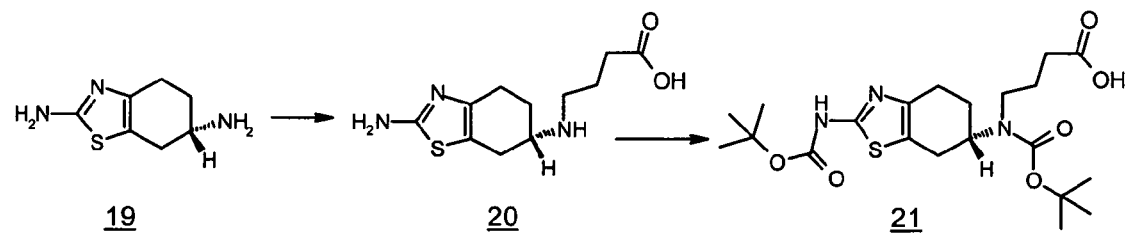

Synthesis of Intermediate Compound (21) as shown in FIG. 7

To a solution of 19 (169 mg, 1.0 mmol) in dioxane (20 mL) and water (10 mL) is added 4-iodobutyric acid (214 mg, 1.0 mmol). The resulting solution is stirred for 24 hours. During this period of time, the pH of the solution is kept at 7-8 by adding 0.5 N NaOH solution. The solvents are removed under reduced pressure. The residue is purified using column chromatography on silica, yielding compound 20.

To a solution of 20 (179 mg, 0.7 mmol) in dioxane (6 mL) and water (3 mL) is added 1N NaOH (2.1 mL) at 0° C. To the resulting solution is added di-tert-butyl dicarbonate (336 mg, 1.54 mmol) over the course of 30 minutes. The mixture is stirred at room temperature for 12 hours. Dioxane is removed under reduced pressure. To the resulting water solution is added ethyl acetate. The pH of the solution is adjusted to about pH 3 by the addition of 0.2 N HCl solution at 0° C. The organic layer is separated, washed with water (twice), dried over anhydrous $MgSO_4$, filtered and concentrated in vacuo. The residue is purified by using column chromatography on silica, yielding intermediate compound 21.

EXAMPLE 11

Figure 8:
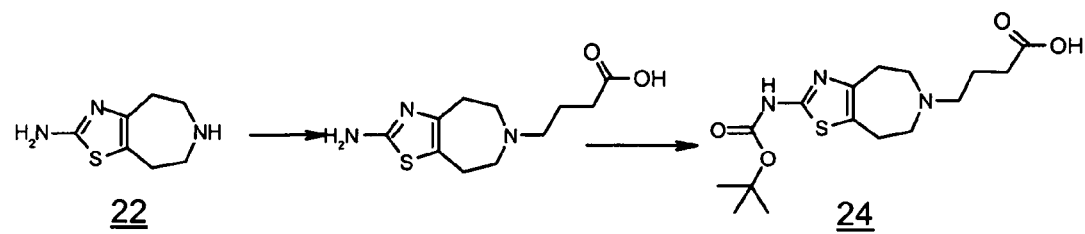

Synthesis of Intermediate Compound (24) as shown in FIG. 8

To a solution of 22 (169 mg, 1.0 mmol) in dioxane (20 mL) and water (10 mL) is added 4-iodobutyric acid (214 mg, 1.0 mmol). The resulting solution is stirred for 24 hours. During this period of time, the pH of the solution is kept at 7-8 by adding 0.5 N NaOH solution. The solvents are removed under reduced pressure. The residue is purified using column chromatography on silica, yielding compound 23.

To a solution of 23 (179 mg, 0.7 mmol) in dioxane (6 mL) and water (3 mL) is added 1N NaOH (1.4 mL) at 0° C. To the resulting solution is added di-tert-butyl dicarbonate (168 mg, 0.77 mmol) over the course of 30 minutes. The mixture is stirred at room temperature for 12 hours. The pH of the solution is adjusted to about 4-5 by addition of 0.2 N HCl solution at 0° C. The solution is concentrated in vacuo. The residue is purified by using column chromatography on silica, yielding intermediate compound 24.

EXAMPLE 12

Figure 9:
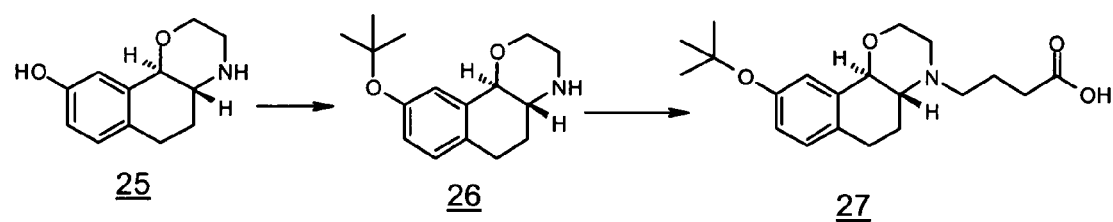

Synthesis of Intermediate Compound (27) as shown in FIG. 9

A mixture of 25 (205 mg, 1.00 mmol), 2-methylpropene (84 mg, 1.50 mmol), and concentrated $H_2SO_4$ in $CH_2Cl_2$ (20 mL) is stirred at room temperature overnight. The solution is washed with saturated $NaHCO_3$ in aqueous solution (2 times) and brine (2 times) and dried over anhydrous $MgSO_4$, filtered, and concentrated in vacuo. The residue is purified using column chromatography on silica, yielding compound 26.

To a mixture of 1-adamantanamine hydrochloride 26 (209 mg, 0.8 mmol) and N,N-diisopropylethylamine (310 mg, 2.4 mmol) in methylene chloride (20 mL) is added 4-iodobutyric acid (171 mg, 0.8 mmol). The resulting solution is stirred at room temperature overnight. The solution is concentrated in vacuo. The residue is purified using column chromatography on silica, yielding intermediate compound 27.

Synthesis of Other Compounds

The compounds listed below can be synthesized according to the procedures described above.

For the introduction of Dop1, Dop2, Dop3 or Dop4 residue(s) into peptides, Dop1-OH, Dop2-OH, Dop3-OH or Dop4-OH (WO 02/100888 A1) was used during the syntheses, respectively.

For the synthesis of the Dop5 containing peptides, Fmoc-Dopa(acetonide)-OH (Novabiochem, San Diego, Calif.) was used.

For the Dop6 residue in peptides, compound 11 is used during the synthesis.

For the Dop7 residue in peptides, compound 21 is used during the synthesis.

For the Dop8 residue in peptides, compound 14 is used during the synthesis.

For the Dop9 residue in peptides, compound 24 is used during the synthesis.

For the Dop10 residue in peptides, compound 3 is used during the synthesis.

For the Dop11 residue in peptides, compound 6 is used during the synthesis.

For the Dop12 residue in peptides, compound 27 is used during the synthesis.

For the Dop13 residue in peptides, compound 18 is used during the synthesis.

Table 1 lists somatostatin-dopamine chimeric analogs likely to have somatostatin and dopamine activity in vitro or in vivo.

TABLE 1

Dop2-DPhe-Doc-DPhe-cyclo[Cys-3ITyr-DTrp-Lys-Val-Cys]-Thr-NH₂

Ac-Lys(Dop2)-DTyr-DTyr-cyclo[Cys-Tyr-DTrp-Lys-Abu-Cys]-Thr-NH₂

Ac-DLys(Dop2)-DPhe-cyclo[Cys-3ITyr-DTrp-Lys-Thr-Cys]-Thr-NH₂

Dop2-Lys(Ac)-DTyr-DTyr-cyclo[Cys-Tyr-DTrp-Lys-Abu-Cys]-Thr-NH₂

Dop2-DLys(Ac)-DPhe-cyclo[Cys-3ITyr-DTrp-Lys-Thr-Cys]-Thr-NH₂

Dop3-DPhe-cyclo[Cys-Tyr-DTrp-Lys-Abu-Cys]-Thr-NH₂

Dop4-DPhe-cyclo[Cys-Tyr-DTrp-Lys-Abu-Cys]-Thr-NH₂

Dop3-Aepa-DPhe-cyclo[Cys-Tyr-DTrp-Lys-Abu-Cys]-Thr-NH₂

Dop4-Aepa-DPhe-cyclo[Cys-Tyr-DTrp-Lys-Abu-Cys]-Thr-NH₂

Dop5-DPhe-cyclo[Cys-Tyr-DTrp-Lys-Abu-Cys]-Thr-NH₂

Dop6-DPhe-cyclo[Cys-Tyr-DTrp-Lys-Abu-Cys]-Thr-NH₂

Dop7-DPhe-cyclo[Cys-Tyr-DTrp-Lys-Abu-Cys]-Thr-NH₂

Dop8-DPhe-cyclo[Cys-Tyr-DTrp-Lys-Abu-Cys]-Thr-NH₂

Dop9-DPhe-cyclo[Cys-Tyr-DTrp-Lys-Abu-Cys]-Thr-NH₂

Dop10-DPhe-cyclo[Cys-Tyr-DTrp-Lys-Abu-Cys]-Thr-NH₂

Dop11-DPhe-cyclo[Cys-Tyr-DTrp-Lys-Abu-Cys]-Thr-NH₂

Dop12-DPhe-cyclo[Cys-Tyr-DTrp-Lys-Abu-Cys]-Thr-NH₂

Dop13-DPhe-cyclo[Cys-Tyr-DTrp-Lys-Abu-Cys]-Thr-NH₂

Dop5-cyclo[Cys-Tyr-DTrp-Lys-Abu-Cys]-Thr-NH₂

Dop6-cyclo[Cys-Tyr-DTrp-Lys-Abu-Cys]-Thr-NH₂

Dop7-cyclo[Cys-Tyr-DTrp-Lys-Abu-Cys]-Thr-NH₂

Dop8-cyclo[Cys-Tyr-DTrp-Lys-Abu-Cys]-Thr-NH₂

Dop9-cyclo[Cys-Tyr-DTrp-Lys-Abu-Cys]-Thr-NH₂

Dop10-cyclo[Cys-Tyr-DTrp-Lys-Abu-Cys]-Thr-NH₂

Dop11-cyclo[Cys-Tyr-DTrp-Lys-Abu-Cys]-Thr-NH₂

Dop12-cyclo[Cys-Tyr-DTrP-Lys-Abu-Cys]-Thr-NH₂

Dop13-cyclo[Cys-Tyr-DTrp-Lys-Abu-Cys]-Thr-NH₂

Dop5-D2Nal-cyclo[Cys-Tyr-DTrp-Lys-Val-Cys]-Thr-NH₂

Dop6-D2Nal-cyclo[Cys-Tyr-DTrp-Lys-Val-Cys]-Thr-NH₂

Dop7-D2Nal-cyclo[Cys-Tyr-DTrp-Lys-Val-Cys]-Thr-NH₂

Dop8-D2Nal-cyclo[Cys-Tyr-DTrp-Lys-Val-Cys]-Thr-NH₂

Dop9-D2Nal-cyclo[Cys-Tyr-DTrp-Lys-Val-Cys]-Thr-NH₂

Dop10-D2Nal-cyclo[Cys-Tyr-DTrp-Lys-Val-Cys]-Thr-NH₂

Dop11-D2Nal-cyclo[Cys-Tyr-DTrp-Lys-Val-Cys]-Thr-NH₂

Dop12-D2Nal-cyclo[Cys-Tyr-DTrp-Lys-Val-Cys]-Thr-NH₂

TABLE 1-continued

Dop13-D2Nal-cyclo[Cys-Tyr-DTrp-Lys-Val-Cys]-Thr-NH₂

Dop5-cyclo[Cys-Tyr-DTrp-Lys-Val-Cys]-Thr-NH₂

Dop6-cyclo[Cys-Tyr-DTrp-Lys-Val-Cys]-Thr-NH₂

Dop7-cyclo[Cys-Tyr-DTrp-Lys-Val-Cys]-Thr-NH₂

Dop8-cyclo[Cys-Tyr-DTrp-Lys-Val-Cys]-Thr-NH₂

Dop9-cyclo[Cys-Tyr-DTrp-Lys-Val-Cys]-Thr-NH₂

Dop10-cyclo[Cys-Tyr-DTrp-Lys-Val-Cys]-Thr-NH₂

Dop11-cyclo[Cys-Tyr-DTrp-Lys-Val-Cys]-Thr-NH₂

Dop12-cyclo[Cys-Tyr-DTrp-Lys-Val-Cys]-Thr-NH₂

Dop13-cyclo[Cys-Tyr-DTrp-Lys-Val-Cys]-Thr-NH₂

Dop5-DPhe-cyclo[Cys-Phe-DTrp-Lys-Thr-Cys]-Thr-ol

Dop6-DPhe-cyclo[Cys-Phe-DTrp-Lys-Thr-Cys]-Thr-ol

Dop7-DPhe-cyclo[Cys-Phe-DTrp-Lys-Thr-Cys]-Thr-ol

Dop8-DPhe-cyclo[Cys-Phe-DTrp-Lys-Thr-Cys]-Thr-ol

Dop9-DPhe-cyclo[Cys-Phe-DTrp-Lys-Thr-Cys]-Thr-ol

Dop10-DPhe-cyclo[Cys-Phe-DTrp-Lys-Thr-Cys]-Thr-ol

Dop11-DPhe-cyclo[Cys-Phe-DTrp-Lys-Thr-Cys]-Thr-ol

Dop12-DPhe-cyclo[Cys-Phe-DTrp-Lys-Thr-Cys]-Thr-ol

Dop13-DPhe-cyclo[Cys-Phe-DTrp-Lys-Thr-Cys]-Thr-ol

Dop5-cyclo[Cys-Phe-DTrp-Lys-Thr-Cys]-Thr-ol

Dop6-cyclo[Cys-Phe-DTrp-Lys-Thr-Cys]-Thr-ol

Dop7-cyclo[Cys-Phe-DTrp-Lys-Thr-Cys]-Thr-ol

Dop8-cyclo[Cys-Phe-DTrp-Lys-Thr-Cys]-Thr-ol

Dop9-cyclo[Cys-Phe-DTrp-Lys-Thr-Cys]-Thr-ol

Dop10-cyclo[Cys-Phe-DTrp-Lys-Thr-Cys]-Thr-ol

Dop11-cyclo[Cys-Phe-DTrp-Lys-Thr-Cys]-Thr-ol

Dop12-cyclo[Cys-Phe-DTrp-Lys-Thr-Cys]-Thr-al

Dop13-cyclo[Cys-Phe-DTrp-Lys-Thr-Cys]-Thr-ol

Dop5-DPhe-cyclo[Cys-Tyr-DTrp-Lys-Thr-Cys]-2Nal-NH₂

Dop6-DPhe-cyclo[Cys-Tyr-DTrp-Lys-Thr-Cys]-2Nal-NH₂

Dop7-DPhe-cyclo[Cys-Tyr-DTrp-Lys-Thr-Cys]-2Nal-NH₂

Dop8-DPhe-cyclo[Cys-Tyr-DTrp-Lys-Thr-Cys]-2Nal-NH₂

Dop9-DPhe-cyclo[Cys-Tyr-DTrp-Lys-Thr-Cys]-2Nal-NH₂

Dop10-DPhe-cyclo[Cys-Tyr-DTrp-Lys-Thr-Cys]-2Nal-NH₂

Dop11-DPhe-cyclo[Cys-Tyr-DTrp-Lys-Thr-Cys]-2Nal-NH₂

Dop12-DPhe-cyclo[Cys-Tyr-DTrp-Lys-Thr-Cys]-2Nal-NH₂

Dop13-DPhe-cyclo[Cys-Tyr-DTrp-Lys-Thr-Cys]-2Nal-NH₂

Dop5-cyclo[Cys-Tyr-DTrp-Lys-Thr-Cys]-2Nal-NH₂

Dop6-cyclo[Cys-Tyr-DTrp-Lys-Thr-Cys]-2Nal-NH₂

Dop7-cyclo[Cys-Tyr-DTrp-Lys-Thr-Cys]-2Nal-NH₂

Dop8-cyclo[Cys-Tyr-DTrp-Lys-Thr-Cys]-2Nal-NH₂

Dop9-cyclo[Cys-Tyr-DTrp-Lys-Thr-Cys]-2Nal-NH₂

Dop10-cyclo[Cys-Tyr-DTrp-Lys-Thr-Cys]-2Nal-NH₂

Dop11-cyclo[Cys-Tyr-DTrp-Lys-Thr-Cys]-2Nal-NH₂

Dop12-cyclo[Cys-Tyr-DTrp-Lys-Thr-Cys]-2Nal-NH₂

Dop13-cyclo[Cys-Tyr-DTrp-Lys-Thr-Cys]-2Nal-NH₂

Dop1-DPhe-cyclo[Cys-3ITyr-DTrp-Lys-Thr-Cys]-Thr-NH₂

Dop2-DPhe-cyclo[Cys-3ITyr-DTrp-Lys-Thr-Cys]-Thr-NH₂

Dop1-Aepa-DPhe-cyclo[Cys-3ITyr-DTrp-Lys-Thr-Cys]-Thr-NH₂

Dop2-Aepa-DPhe-cyclo[Cys-3ITyr-DTrp-Lys-Thr-Cys]-Thr-NH₂

Dop3-Aepa-DPhe-cyclo[Cys-3ITyr-DTrp-Lys-Thr-Cys]-Thr-NH₂

Dop4-Aepa-DPhe-cyclo[Cys-3ITyr-DTrp-Lys-Thr-Cys]-Thr-NH₂

Dop3-DPhe-cyclo[Cys-3ITyr-DTrp-Lys-Thr-Cys]-Thr-NH₂

Dop4-DPhe-cyclo[Cys-3ITyr-DTrp-Lys-Thr-Cys]-Thr-NH₂

Dop5-DPhe-cyclo[Cys-3ITyr-DTrp-Lys-Thr-Cys]-Thr-NH₂

Dop6-DPhe-cyclo[Cys-3ITyr-DTrp-Lys-Thr-Cys]-Thr-NH₂

Dop7-DPhe-cyclo[Cys-3ITyr-DTrp-Lys-Thr-Cys]-Thr-NH₂

Dop8-DPhe-cyclo[Cys-3ITyr-DTrp-Lys-Thr-Cys]-Thr-NH₂

Dop9-DPhe-cyclo[Cys-3ITyr-DTrp-Lys-Thr-Cys]-Thr-NH₂

Dop10-DPhe-cyclo[Cys-3ITyr-DTrp-Lys-Thr-Cys]-Thr-NH₂

Dop11-DPhe-cyclo[Cys-3ITyr-DTrp-Lys-Thr-Cys]-Thr-NH₂

Dop12-DPhe-cyclo[Cys-3ITyr-DTrp-Lys-Thr-Cys]-Thr-NH₂

Dop13-DPhe-cyclo[Cys-3ITyr-DTrp-Lys-Thr-Cys]-Thr-NH₂

Dop3-cyclo[Cys-3ITyr-DTrp-Lys-Thr-Cys]-Thr-NH₂

Dop4-cyclo[Cys-3ITyr-DTrp-Lys-Thr-Cys]-Thr-NH₂

Dop5-cyclo[Cys-3ITyr-DTrp-Lys-Thr-Cys]-Thr-NH₂

Dop6-cyclo[Cys-3ITyr-DTrp-Lys-Thr-Cys]-Thr-NH₂

Dop7-cyclo[Cys-3ITyr-DTrp-Lys-Thr-Cys]-Thr-NH₂

TABLE 1-continued

Dop8-cyclo[Cys-3ITyr-DTrp-Lys-Thr-Cys]-Thr-NH$_2$

Dop9-cyclo[Cys-3ITyr-DTrp-Lys-Thr-Cys]-Thr-NH$_2$

Dop10-cyclo[Cys-3ITyr-DTrp-Lys-Thr-Cys]-Thr-NH$_2$

Dop11-cyclo[Cys-3ITyr-DTrp-Lys-Thr-Cys]-Thr-NH$_2$

Dop12-cyclo[Cys-3ITyr-DTrp-Lys-Thr-Cys]-Thr-NH$_2$

Dop13-cyclo[Cys-3ITyr-DTrp-Lys-Thr-Cys]-Thr-NH$_2$

Dop1-Caeg-cyclo[DCys-3Pal-DTrp-Lys-DCys]-Thr(Bzl)-Tyr-NH$_2$

Dop2-Caeg-cyclo[DCys-3Pal-DTrp-Lys-DCys]-Thr(Bzl)-Tyr-NH$_2$

Dop3-Caeg-cyclo[DCys-3Pal-DTrp-Lys-DCys]-Thr(Bzl)-Tyr-NH$_2$

Dop4-Caeg-cyclo[DCys-3Pal-DTrp-Lys-DCys]-Thr(Bzl)-Tyr-NH$_2$

Dop1-Aepa-Caeg-cyclo[DCys-3Pal-DTrp-Lys-DCys]-Thr(Bzl)-Tyr-NH$_2$

Dop2-Aepa-Caeg-cyclo[DCys-3Pal-DTrp-Lys-DCys]-Thr(Bzl)-Tyr-NH$_2$

Dop3-Aepa-Caeg-cyclo[DCys-3Pal-DTrp-Lys-DCys]-Thr(Bzl)-Tyr-NH$_2$

Dop4-Aepa-Caeg-cyclo[DCys-3Pal-DTrp-Lys-DCys]-Thr(Bzl)-Tyr-NH$_2$

Dop5-Caeg-cyclo[DCys-3Pal-DTrp-Lys-DCys]-Thr(Bzl)-Tyr-NH$_2$

Dop6-Caeg-cyclo[DCys-3Pal-DTrp-Lys-DCys]-Thr(Bzl)-Tyr-NH$_2$

Dop7-Caeg-cyclo[DCys-3Pal-DTrp-Lys-DCys]-Thr(Bzl)-Tyr-NH$_2$

Dop8-Caeg-cyclo[DCys-3Pal-DTrp-Lys-DCys]-Thr(Bzl)-Tyr-NH$_2$

Dop9-Caeg-cyclo[DCys-3Pal-DTrp-Lys-DCys]-Thr(Bzl)-Tyr-NH$_2$

Dop10-Caeg-cyclo[DCys-3Pal-DTrp-Lys-DCys]-Thr(Bzl)-Tyr-NH$_2$

Dop11-Caeg-cyclo[DCys-3Pal-DTrp-Lys-DCys]-Thr(Bzl)-Tyr-NH$_2$

Dop12-Caeg-cyclo[DCys-3Pal-DTrp-Lys-DCys]-Thr(Bzl)-Tyr-NH$_2$

Dop13-Caeg-cyclo[DCys-3Pal-DTrp-Lys-DCys]-Thr(Bzl)-Tyr-NH$_2$

Dop1-Caeg-cyclo[DCys-Phe-DTrp-Lys-DCys]-Ser(Bzl)-Tyr-NH$_2$

Dop2-Caeg-cyclo[DCys-Phe-DTrp-Lys-DCys]-Ser(Bzl)-Tyr-NH$_2$

Dop3-Caeg-cyclo[DCys-Phe-DTrp-Lys-DCys]-Ser(Bzl)-Tyr-NH$_2$

Dop4-Caeg-cyclo[DCys-Phe-DTrp-Lys-DCys]-Ser(Bzl)-Tyr-NH$_2$

Dop1-Aepa-Caeg-cyclo[DCys-Phe-DTrp-Lys-DCys]-Ser(Bzl)-Tyr-NH$_2$

Dop2-Aepa-Caeg-cyclo[DCys-Phe-DTrp-Lys-DCys]-Ser(Bzl)-Tyr-NH$_2$

Dop3-Aepa-Caeg-cyclo[DCys-Phe-DTrp-Lys-DCys]-Ser(Bzl)-Tyr-NH$_2$

Dop4-Aepa-Caeg-cyclo[DCys-Phe-DTrp-Lys-DCys]-Ser(Bzl)-Tyr-NH$_2$

Dop5-Aepa-Caeg-cyclo[DCys-Phe-DTrp-Lys-DCys]-Ser(Bzl)-Tyr-NH$_2$

Dop6-Caeg-cyclo[DCys-Phe-DTrp-Lys-DCys]-Ser(Bzl)-Tyr-NH$_2$

Dop7-Caeg-cyclo[DCys-Phe-DTrp-Lys-DCys]-Ser(Bzl)-Tyr-NH$_2$

Dop8-Caeg-cyclo[DCys-Phe-DTrp-Lys-DCys]-Ser(Bzl)-Tyr-NH$_2$

Dop9-Caeg-cyclo[DCys-Phe-DTrp-Lys-DCys]-Ser(Bzl)-Tyr-NH$_2$

Dop10-Caeg-cyclo[DCys-Phe-DTrp-Lys-DCys]-Ser(Bzl)-Tyr-NH$_2$

Dop11-Caeg-cyclo[DCys-Phe-DTrp-Lys-DCys]-Ser(Bzl)-Tyr-NH$_2$

Dop12-Caeg-cyclo[DCys-Phe-DTrp-Lys-DCys]-Ser(Bzl)-Tyr-NH$_2$

Dop13-Caeg-cyclo[DCys-Phe-DTrp-Lys-DCys]-Ser(Bzl)-Tyr-NH$_2$

Dop5-cyclo[Cys-Phe-Phe-DTrp-Lys-Thr-Phe-Cys]-NH$_2$

Dop6-cyclo[Cys-Phe-Phe-DTrp-Lys-Thr-Phe-Cys]-NH$_2$

Dop7-cyclo[Cys-Phe-Phe-DTrp-Lys-Thr-Phe-Cys]-NH$_2$

Dop8-cyclo[Cys-Phe-Phe-DTrp-Lys-Thr-Phe-Cys]-NH$_2$

Dop9-cyclo[Cys-Phe-Phe-DTrp-Lys-Thr-Phe-Cys]-NH$_2$

Dop10-cyclo[Cys-Phe-Phe-DTrp-Lys-Thr-Phe-Cys]-NH$_2$

Dop11-cyclo[Cys-Phe-Phe-DTrp-Lys-Thr-Phe-Cys]-NH$_2$

Dop12-cyclo[Cys-Phe-Phe-DTrp-Lys-Thr-Phe-Cys]-NH$_2$

Dop13-cyclo[Cys-Phe-Phe-DTrp-Lys-Thr-Phe-Cys]-NH$_2$

Dop5-DPhe-cyclo[Cys-Phe-(N-Me)DTrp-Lys-Thr-Cys]-Thr-NH$_2$

Dop6-DPhe-cyclo[Cys-Phe-(N-Me)DTrp-Lys-Thr-Cys]-Thr-NH$_2$

Dop7-DPhe-cyclo[Cys-Phe-(N-Me)DTrp-Lys-Thr-Cys]-Thr-NH$_2$

Dop8-DPhe-cyclo[Cys-Phe-(N-Me)DTrp-Lys-Thr-Cys]-Thr-NH$_2$

Dop9-DPhe-cyclo[Cys-Phe-(N-Me)DTrp-Lys-Thr-Cys]-Thr-NH$_2$

Dop10-DPhe-cyclo[Cys-Phe-(N-Me)DTrp-Lys-Thr-Cys]-Thr-NH$_2$

Dop11-DPhe-cyclo[Cys-Phe-(N-Me)DTrp-Lys-Thr-Cys]-Thr-NH$_2$

Dop13-DPhe-cyclo[Cys-Phe-(N-Me)DTrp-Lys-Thr-Cys]-Thr-NH$_2$

Dop13-DPhe-cyclo[Cys-Phe-(N-Me)DTrp-Lys-Thr-Cys]-Thr-NH$_2$

TABLE 1-continued

Dop5-cyclo[Cys-Phe-(N-Me)DTrp-Lys-Thr-Cys]-Thr-NH$_2$

Dop6-cyclo[Cys-Phe-(N-Me)DTrp-Lys-Thr-Cys]-Thr-NH$_2$

Dop7-cyclo[Cys-Phe-(N-Me)DTrp-Lys-Thr-Cys]-Thr-NH$_2$

Dop8-cyclo[Cys-Phe-(N-Me)DTrp-Lys-Thr-Cys]-Thr-NH$_2$

Dop9-cyclo[Cys-Phe-(N-Me)DTrp-Lys-Thr-Cys]-Thr-NH$_2$

Dop10-cyclo[Cys-Phe-(N-Me)DTrp-Lys-Thr-Cys]-Thr-NH$_2$

Dop11-cyclo[Cys-Phe-(N-Me)DTrp-Lys-Thr-Cys]-Thr-NH$_2$

Dop12-cyclo[Cys-Phe-(N-Me)DTrp-Lys-Thr-Cys]-Thr-NH$_2$

Dop13-cyclo[Cys-Phe-(N-Me)DTrp-Lys-Thr-Cys]-Thr-NH$_2$

Dop2-Lys(Dop2)-cyclo[Cys-Tyr-DTrp-Lys-Abu-Cys]-Thr-NH$_2$

Dop2-DLys(Dop2)-cyclo[Cys-Tyr-DTrp-Lys-Abu-Cys]-Thr-NH$_2$

Dop2-Lys(Dop2)-DPhe-cyclo[Cys-Tyr-DTrp-Lys-Abu-Cys]-Thr-NH$_2$

Dop2-DLys(Dop2)-DPhe-cyclo[Cys-Tyr-DTrp-Lys-Abu-Cys]-Thr-NH$_2$

Dop2-Lys(Dop2)-Lys-DTyr-DTyr-cyclo[Cys-Tyr-DTrp-Lys-Abu-Cys]-Thr-NH$_2$

Dop2-DLys(Dop2)-Lys-DTyr-DTyr-cyclo[Cys-Tyr-DTrp-Lys-Abu-Cys]-Thr-NH$_2$

Dop2-DLys(Dop2)-DTyr-DTyr-cyclo[Cys-Tyr-DTrp-Lys-Abu-Cys]-Thr-NH$_2$

Dop1-Lys(Dop1)-DPhe-cyclo[Cys-Tyr-DTrp-Lys-Abu-Cys]-Thr-NH$_2$

Dop1-Lys(Dop1)-Aepa-DPhe-cyclo[Cys-Tyr-DTrp-Lys-Abu-Cys]-Thr-NH$_2$

Dop1-Lys(Dop1)-cyclo[Cys-Tyr-DTrp-Lys-Abu-Cys]-Thr-NH$_2$

Dop1-Lys(Dop1)-Lys-DTyr-DTyr-cyclo[Cys-Tyr-DTrp-Lys-Abu-Cys]-Thr-NH$_2$

Dop1-Lys(Dop1)-DTyr-DTyr-cyclo[Cys-Tyr-DTrp-Lys-Abu-Cys]-Thr-NH$_2$

Dop1-DLys(Dop1)-DPhe-cyclo[Cys-Tyr-DTrp-Lys-Abu-Cys]-Thr-NH$_2$

Dop1-DLys(Dop1)-Aepa-DPhe-cyclo[Cys-Tyr-DTrp-Lys-Abu-Cys]-Thr-NH$_2$

Dop1-DLys(Dop1)-cyclo[Cys-Tyr-DTrp-Lys-Abu-Cys]-Thr-NH$_2$

Dop1-DLys(Dop1)-Lys-DTyr-DTyr-cyclo[Cys-Tyr-DTrp-Lys-Abu-Cys]-Thr-NH$_2$

Dop1-DLys(Dop1)-DTyr-DTyr-cyclo[Cys-Tyr-DTrp-Lys-Abu-Cys]-Thr-NH$_2$

Dop1-Lys(Dop1)-D2Nal-cyclo[Cys-Tyr-DTrp-Lys-Val-Cys]-Thr-NH$_2$

Dop1-Lys(Dop1)-cyclo[Cys-Tyr-DTrp-Lys-Val-Cys]-Thr-NH$_2$

Dop1-DLys(Dop1)-Lys-DTyr-DTyr-cyclo[Cys-Tyr-DTrp-Lys-Abu-Cys]-Thr-NH$_2$

Dop1-Lys(Dop1)-DTyr-DTyr-cyclo[Cys-Tyr-DTrp-Lys-Val-Cys]-Thr-NH$_2$

Dop1-Lys(Dop1)-DPhe-cyclo[Cys-Tyr-DTrp-Lys-Thr-Cys]-2Nal-NH$_2$

Dop1-Lys(Dop1)-cyclo[Cys-Tyr-DTrp-Lys-Thr-Cys]-2Nal-NH$_2$

Dop1-Lys(Dop1)-Lys-DTyr-DTyr-cyclo[Cys-Tyr-DTrp-Lys-Thr-Cys]-2Nal-NH$_2$

Dop1-Lys(Dop1)-DTyr-DTyr-cyclo[Cys-Tyr-DTrp-Lys-Thr-Cys]-2Nal-NH$_2$

Dop1-Lys(Dop1)-DPhe-cyclo[Cys-Phe-DTrp-Lys-Thr-Cys]-Thr-ol

Dop1-Lys(Dop1)-cyclo[Cys-Phe-DTrp-Lys-Thr-Cys]-Thr-ol

Dop1-Lys(Dop1)-Lys-DTyr-DTyr-cyclo[Cys-Phe-DTrp-Lys-Thr-Cys]-Thr-ol

Dop1-Lys(Dop1)-DTyr-DTyr-cyclo[Cys-Phe-DTrp-Lys-Thr-Cys]-Thr-ol

Dop1-Lys(Dop2)-DPhe-cyclo[Cys-Tyr-DTrp-Lys-Val-Cys]-Trp-NH$_2$

Dop1-Lys(Dop2)-cyclo[Cys-Tyr-DTrp-Lys-Val-Cys]-Trp-NH$_2$

Dop1-Lys(Dop2)-Lys-DTyr-DTyr-cyclo[Cys-Tyr-DTrp-Lys-Val-Cys]-Trp-NH$_2$

Dop1-Lys(Dop2)-DTyr-DTyr-cyclo[Cys-Tyr-DTrp-Lys-Val-Cys]-Trp-NH$_2$

Dop2-Lys(Dop2)-DPhe-cyclo[Cys-Tyr-DTrp-Lys-Abu-Cys]-Thr-NH$_2$

Dop2-Lys(Dop2)-Aepa-DPhe-cyclo[Cys-Tyr-DTrp-Lys-Abu-Cys]-Thr-NH$_2$

Dop2-Lys(Dop2)-cyclo[Cys-Tyr-DTrp-Lys-Abu-Cys]-Thr-NH$_2$

Dop2-Lys(Dop2)-Lys-DTyr-DTyr-cyclo[Cys-Tyr-DTrp-Lys-Abu-Cys]-Thr-NH$_2$

Dop2-Lys(Dop2)-DTyr-DTyr-cyclo[Cys-Tyr-DTrp-Lys-Abu-Cys]-Thr-NH$_2$

Dop2-Lys(Dop2)-Aepa-DTyr-DTyr-cyclo[Cys-Tyr-DTrp-Lys-Abu-Cys]-Thr-NH$_2$

Dop2-DLys(Dop2)-DPhe-cyclo[Cys-Tyr-DTrp-Lys-Abu-Cys]-Thr-NH$_2$

Dop2-DLys(Dop2)-Aepa-DPhe-cyclo[Cys-Tyr-DTrp-Lys-Abu-Cys]-Thr-NH$_2$

Dop2-DLys(Dop2)-cyclo[Cys-Tyr-DTrp-Lys-Abu-Cys]-Thr-NH$_2$

Dop2-DLys(Dop2)-Lys-DTyr-DTyr-cyclo[Cys-Tyr-DTrp-Lys-Abu-Cys]-Thr-NH$_2$

Dop2-DLys(Dop2)-DTyr-DTyr-cyclo[Cys-Tyr-DTrp-Lys-Abu-Cys]-Thr-NH$_2$

Dop2-DLys(Dop2)-Aepa-DTyr-DTyr-cyclo[Cys-Tyr-DTrp-Lys-Abu-Cys]-Thr-NH$_2$

TABLE 1-continued

Dop2-Lys(Dop2)-D2Nal-cyclo[Cys-Tyr-DTrp-Lys-Val-Cys]-Thr-NH$_2$

Dop2-Lys(Dop2)-cyclo[Cys-Tyr-DTrp-Lys-Val-Cys]-Thr-NH$_2$

Dop2-Lys(Dop2)-Lys-DTyr-DTyr-cyclo[Cys-Tyr-DTrp-Lys-Val-Cys]-Thr-NH$_2$

Dop2-Lys(Dop2)-DTyr-DTyr-cyclo[Cys-Tyr-DTrp-Lys-Val-Cys]-Thr-NH$_2$

Dop2-Lys(Dop2)-DPhe-cyclo[Cys-Tyr-DTrp-Lys-Thr-Cys]-2Nal-NH$_2$

Dop2-Lys(Dop2)-cyclo[Cys-Tyr-DTrp-Lys-Thr-Cys]-2Nal-NH$_2$

Dop2-Lys(Dop2)-Lys-DTyr-DTyr-cyclo[Cys-Tyr-DTrp-Lys-Thr-Cys]-2Nal-NH$_2$

Dop2-Lys(Dop2)-DTyr-DTyr-cyclo[Cys-Tyr-DTrp-Lys-Thr-Cys]-2Nal-NH$_2$

Dop2-Lys(Dop2)-DPhe-cyclo[Cys-Phe-DTrp-Lys-Thr-Cys]-Thr-ol

Dop2-Lys(Dop2)-cyclo[Cys-Phe-DTrp-Lys-Thr-Cys]-Thr-ol

Dop2-Lys(Dop2)-Lys-DTyr-DTyr-cyclo[Cys-Phe-DTrp-Lys-Thr-Cys]-Thr-ol

Dop2-Lys(Dop2)-DTyr-DTyr-cyclo[Cys-Phe-DTrp-Lys-Thr-Cys]-Thr-ol

Dop2-Lys(Dop2)-DPhe-cyclo[Cys-Tyr-DTrp-Lys-Val-Cys]-Trp-NH$_2$

Dop2-Lys(Dop2)-cyclo[Cys-Tyr-DTrp-Lys-Val-Cys]-Trp-NH$_2$

Dop2-Lys(Dop2)-Lys-DTyr-DTyr-cyclo[Cys-Tyr-DTrp-Lys-Val-Cys]-Trp-NH$_2$

Dop2-Lys(Dop2)-DTyr-DTyr-cyclo[Cys-Tyr-DTrp-Lys-Val-Cys]-Trp-NH$_2$

Dop3-Lys(Dop3)-DPhe-cyclo[Cys-Tyr-DTrp-Lys-Abu-Cys]-Thr-NH$_2$

Dop3-Lys(Dop3)-Aepa-DPhe-cyclo[Cys-Tyr-DTrp-Lys-Abu-Cys]-Thr-NH$_2$

Dop3-Lys(Dop3)-cyclo[Cys-Tyr-DTrp-Lys-Abu-Cys]-Thr-NH$_2$

Dop3-Lys(Dop3)-Lys-DTyr-DTyr-cyclo[Cys-Tyr-DTrp-Lys-Abu-Cys]-Thr-NH$_2$

Dop3-Lys(Dop3)-DTyr-DTyr-cyclo[Cys-Tyr-DTrp-Lys-Abu-Cys]-Thr-NH$_2$

Dop3-DLys(Dop3)-DPhe-cyclo[Cys-Tyr-DTrp-Lys-Abu-Cys]-Thr-NH$_2$

Dop3-DLys(Dop3)-Aepa-DPhe-cyclo[Cys-Tyr-DTrp-Lys-Abu-Cys]-Thr-NH$_2$

Dop3-DLys(Dop3)-cyclo[Cys-Tyr-DTrp-Lys-Abu-Cys]-Thr-NH$_2$

Dop3-DLys(Dop3)-Lys-DTyr-DTyr-cyclo[Cys-Tyr-DTrp-Lys-Abu-Cys]-Thr-NH$_2$

Dop3-DLys(Dop3)-DTyr-DTyr-cyclo[Cys-Tyr-DTrp-Lys-Abu-Cys]-Thr-NH$_2$

TABLE 1-continued

Dop3-Lys(Dop3)-D2Nal-cyclo[Cys-Tyr-DTrp-Lys-Val-Cys]-Thr-NH$_2$

Dop3-Lys(Dop3)-cyclo[Cys-Tyr-DTrp-Lys-Val-Cys]-Thr-NH$_2$

Dop3-Lys(Dop3)-Lys-DTyr-DTyr-cyclo[Cys-Tyr-DTrp-Lys-Val-Cys]-Thr-NH$_2$

Dop3-Lys(Dop3)-DTyr-DTyr-cyclo[Cys-Tyr-DTrp-Lys-Val-Cys]-Thr-NH$_2$

Dop3-Lys(Dop3)-DPhe-cyclo[Cys-Tyr-DTrp-Lys-Thr-Cys]-2Nal-NH$_2$

Dop3-Lys(Dop3)-cyclo[Cys-Tyr-DTrp-Lys-Thr-Cys]-2Nal-NH$_2$

Dop3-Lys(Dop3)-Lys-DTyr-DTyr-cyclo[Cys-Tyr-DTrp-Lys-Thr-Cys]-2Nal-NH$_2$

Dop3-Lys(Dop3)-DTyr-DTyr-cyclo[Cys-Tyr-DTrp-Lys-Thr-Cys]-2Nal-NH$_2$

Dop3-Lys(Dop3)-DPhe-cyclo[Cys-Phe-DTrp-Lys-Thr-Cys]-Thr-ol

Dop3-Lys(Dop3)-cyclo[Cys-Phe-DTrp-Lys-Thr-Cys]-Thr-ol

Dop3-Lys(Dop3)-Lys-DTyr-DTyr-cyclo[Cys-Phe-DTrp-Lys-Thr-Cys]-Thr-ol

Dop3-Lys(Dop3)-DTyr-DTyr-cyclo[Cys-Phe-DTrp-Lys-Thr-Cys]-Thr-ol

Dop3-Lys(Dop3)-DPhe-cyclo[Cys-Tyr-DTrp-Lys-Val-Cys]-Trp-NH$_2$

Dop3-Lys(Dop3)-cyclo[Cys-Tyr-DTrp-Lys-Val-Cys]-Trp-NH$_2$

Dop3-Lys(Dop3)-Lys-DTyr-DTyr-cyclo[Cys-Tyr-DTrp-Lys-Val-Cys]-Trp-NH$_2$

Dop3-Lys(Dop3)-DTyr-DTyr-cyclo[Cys-Tyr-DTrp-Lys-Val-Cys]-2Nal-NH$_2$

Dop4-Lys(Dop4)-DPhe-cyclo[Cys-Tyr-DTrp-Lys-Abu-Cys]-Thr-NH$_2$

Dop4-Lys(Dop4)-Aepa-DPhe-cyclo[Cys-Tyr-DTrp-Lys-Abu-Cys]-Thr-NH$_2$

Dop4-Lys(Dop4)-cyclo[Cys-Tyr-DTrp-Lys-Abu-Cys]-Thr-NH$_2$

Dop4-Lys(Dop4)-Lys-DTyr-DTyr-cyclo[Cys-Tyr-DTrp-Lys-Abu-Cys]-Thr-NH$_2$

Dop4-Lys(Dop4)-DTyr-DTyr-cyclo[Cys-Tyr-DTrp-Lys-Abu-Cys]-Thr-NH$_2$

Dop4-DLys(Dop4)-DPhe-cyclo[Cys-Tyr-DTrp-Lys-Abu-Cys]-Thr-NH$_2$

Dop4-DLys(Dop4)-Aepa-DPhe-cyclo[Cys-Tyr-DTrp-Lys-Abu-Cys]-Thr-NH$_2$

Dop4-DLys(Dop4)-cyclo[Cys-Tyr-DTrp-Lys-Abu-Cys]-Thr-NH$_2$

Dop4-DLys(Dop4)-Lys-DTyr-DTyr-cyclo[Cys-Tyr-DTrp-Lys-Abu-Cys]-Thr-NH$_2$

Dop4-DLys(Dop4)-DTyr-DTyr-cyclo[Cys-Tyr-DTrp-Lys-Abu-Cys]-Thr-NH$_2$

Dop4-Lys(Dop4)-D2Nal-cyclo[Cys-Tyr-DTrp-Lys-Val-Cys]-Thr-NH$_2$

TABLE 1-continued

Dop4-Lys(Dop4)-cyclo[Cys-Tyr-DTrp-Lys-Val-Cys]-Thr-NH$_2$

Dop4-Lys(Dop4)-Lys-DTyr-DTyr-cyclo[Cys-Tyr-DTrp-Lys-Val-Cys]-Thr-NH$_2$

Dop4-Lys(Dop4)-DTyr-DTyr-cyclo[Cys-Tyr-DTrp-Lys-Val-Cys]-Thr-NH$_2$

Dop4-Lys(Dop4)-DPhe-cyclo[Cys-Tyr-DTrp-Lys-Thr-Cys]-2Nal-NH$_2$

Dop4-Lys(Dop4)-cyclo[Cys-Tyr-DTrp-Lys-Thr-Cys]-2Nal-NH$_2$

Dop4-Lys(Dop4)-Lys-DTyr-DTyr-cyclo[Cys-Tyr-DTrp-Lys-Thr-Cys]-2Nal-NH$_2$

Dop4-Lys(Dop4)-DTyr-DTyr-cyclo[Cys-Tyr-DTrp-Lys-Thr-Cys]-2Nal-NH$_2$

Dop4-Lys(Dop4)-DPhe-cyclo[Cys-Phe-DTrp-Lys-Thr-Cys]-Thr-ol

Dop4-Lys(Dop4)-cyclo[Cys-Phe-DTrp-Lys-Thr-Cys]-Thr-ol

Dop4-Lys(Dop4)-Lys-DTyr-DTyr-cyclo[Cys-Phe-DTrp-Lys-Thr-Cys]-Thr-ol

Dop4-Lys(Dop4)-DTyr-DTyr-cyclo[Cys-Phe-DTrp-Lys-Thr-Cys]-Thr-ol

Dop4-Lys(Dop4)-DPhe-cyclo[Cys-Tyr-DTrp-Lys-Val-Cys]-Trp-NH$_2$

Dop4-Lys(Dop4)-cyclo[Cys-Tyr-DTrp-Lys-Val-Cys]-Trp-NH$_2$

Dop4-Lys(Dop4)-Lys-DTyr-DTyr-cyclo[Cys-Tyr-DTrp-Lys-Val-Cys]-Trp-NH$_2$

Dop4-Lys(Dop4)-DTyr-DTyr-cyclo[Cys-Tyr-DTrp-Lys-Val-Cys]-Trp-NH$_2$

Dop5-Lys(Dop5)-DPhe-cyclo[Cys-Tyr-DTrp-Lys-Abu-Cys]-Thr-NH$_2$

Dop5-Lys(Dop5)-cyclo[Cys-Tyr-DTrp-Lys-Abu-Cys]-Thr-NH$_2$

Dop5-Lys(Dop5)-Lys-DTyr-DTyr-cyclo[Cys-Tyr-DTrp-Lys-Abu-Cys]-Thr-NH$_2$

Dop5-Lys(Dop5)-DTyr-DTyr-cyclo[Cys-Tyr-DTrp-Lys-Abu-Cys]-Thr-NH$_2$

Dop5-DLys(Dop5)-DPhe-cyclo[Cys-Tyr-DTrp-Lys-Abu-Cys]-Thr-NH$_2$

Dop5-DLys(Dop5)-cyclo[Cys-Tyr-DTrp-Lys-Abu-Cys]-Thr-NH$_2$

Dop5-DLys(Dop5)-Lys-DTyr-DTyr-cyclo[Cys-Tyr-DTrp-Lys-Abu-Cys]-Thr-NH$_2$

Dop5-DLys(Dop5)-DTyr-DTyr-cyclo[Cys-Tyr-DTrp-Lys-Abu-Cys]-Thr-NH$_2$

Dop5-Lys(Dop5)-D2Nal-cyclo[Cys-Tyr-DTrp-Lys-Val-Cys]-Thr-NH$_2$

Dop5-Lys(Dop5)-cyclo[Cys-Tyr-DTrp-Lys-Val-Cys]-Thr-NH$_2$

Dop5-Lys(Dop5)-Lys-DTyr-DTyr-cyclo[Cys-Tyr-DTrp-Lys-Val-Cys]-Thr-NH$_2$

Dop5-Lys(Dop5)-DTyr-DTyr-cyclo[Cys-Tyr-DTrp-Lys-Val-Cys]-Thr-NH$_2$

Dop5-Lys(Dop5)-DPhe-cyclo[Cys-Tyr-DTrp-Lys-Thr-Cys]-2Nal-NH$_2$

Dop5-Lys(Dop5)-cyclo[Cys-Tyr-DTrp-Lys-Thr-Cys]-2Nal-NH$_2$

Dop5-Lys(Dop5)-Lys-DTyr-DTyr-cyclo[Cys-Tyr-DTrp-Lys-Thr-Cys]-2Nal-NH$_2$

Dop5-Lys(Dop5)-DTyr-DTyr-cyclo[Cys-Tyr-DTrp-Lys-Thr-Cys]-2Nal-NH$_2$

Dop5-Lys(Dop5)-DPhe-cyclo[Cys-Phe-DTrp-Lys-Thr-Cys]-Thr-ol

Dop5-Lys(Dop5)-cyclo[Cys-Phe-DTrp-Lys-Thr-Cys]-Thr-ol

Dop5-Lys(Dop5)-Lys-DTyr-DTyr-cyclo[Cys-Phe-DTrp-Lys-Thr-Cys]-Thr-ol

Dop5-Lys(Dop5)-DTyr-DTyr-cyclo[Cys-Phe-DTrp-Lys-Thr-Cys]-Thr-ol

Dop5-Lys(Dop5)-DPhe-cyclo[Cys-Tyr-DTrp-Lys-Val-Cys]-Trp-NH$_2$

Dop5-Lys(Dop5)-cyclo[Cys-Tyr-DTrp-Lys-Val-Cys]-Trp-NH$_2$

Dop5-Lys(Dop5)-Lys-DTyr-DTyr-cyclo[Cys-Tyr-DTrp-Lys-Val-Cys]-Trp-NH$_2$

Dop5-Lys(Dop5)-DTyr-DTyr-cyclo[Cys-Tyr-DTrp-Lys-Val-Cys]-Trp-NH$_2$

Dop6-Lys(Dop6)-DPhe-cyclo[Cys-Tyr-DTrp-Lys-Abu-Cys]-Thr-NH$_2$

Dop6-Lys(Dop6)-cyclo[Cys-Tyr-DTrp-Lys-Abu-Cys]-Thr-NH$_2$

Dop6-Lys(Dop6)-Lys-DTyr-DTyr-cyclo[Cys-Tyr-DTrp-Lys-Abu-Cys]-Thr-NH$_2$

Dop6-Lys(Dop6)-DTyr-DTyr-cyclo[Cys-Tyr-DTrp-Lys-Abu-Cys]-Thr-NH$_2$

Dop6-DLys(Dop6)-DPhe-cyclo[Cys-Tyr-DTrp-Lys-Abu-Cys]-Thr-NH$_2$

Dop6-DLys(Dop6)-cyclo[Cys-Tyr-DTrp-Lys-Abu-Cys]-Thr-NH$_2$

Dop6-DLys(Dop6)-Lys-DTyr-DTyr-cyclo[Cys-Tyr-DTrp-Lys-Abu-Cys]-Thr-NH$_2$

Dop6-DLys(Dop6)-DTyr-DTyr-cyclo[Cys-Tyr-DTrp-Lys-Abu-Cys]-Thr-NH$_2$

Dop6-Lys(Dop6)-D2Nal-cyclo[Cys-Tyr-DTrp-Lys-Val-Cys]-Thr-NH$_2$

Dop6-Lys(Dop6)-cyclo[Cys-Tyr-DTrp-Lys-Val-Cys]-Thr-NH$_2$

Dop6-Lys(Dop6)-Lys-DTyr-DTyr-cyclo[Cys-Tyr-DTrp-Lys-Val-Cys]-Thr-NH$_2$

Dop6-Lys(Dop6)-DTyr-DTyr-cyclo[Cys-Tyr-DTrp-Lys-Val-Cys]-Thr-NH$_2$

Dop6-Lys(Dop6)-DPhe-cyclo[Cys-Tyr-DTrp-Lys-Thr-Cys]-2Nal-NH$_2$

TABLE 1-continued

Dop6-Lys(Dop6)-cyclo[Cys-Tyr-DTrp-Lys-Thr-Cys]-2Nal-NH$_2$

Dop6-Lys(Dop6)-Lys-DTyr-DTyr-cyclo[Cys-Tyr-DTrp-Lys-Thr-Cys]-2Nal-NH$_2$

Dop6-Lys(Dop6)-DTyr-DTyr-cyclo[Cys-Tyr-DTrp-Lys-Thr-Cys]-2Nal-NH$_2$

Dop6-Lys(Dop6)-DPhe-cyclo[Cys-Phe-DTrp-Lys-Thr-Cys]-Thr-ol

Dop6-Lys(Dop6)-cyclo[Cys-Phe-DTrp-Lys-Thr-Cys]-Thr-ol

Dop6-Lys(Dop6)-Lys-DTyr-DTyr-cyclo[Cys-Phe-DTrp-Lys-Thr-Cys]-Thr-ol

Dop6-Lys(Dop6)-DTyr-DTyr-cyclo[Cys-Phe-DTrp-Lys-Thr-Cys]-Thr-ol

Dop6-Lys(Dop6)-DPhe-cyclo[Cys-Tyr-DTrp-Lys-Val-Cys]-Trp-NH$_2$

Dop6-Lys(Dop6)-cyclo[Cys-Tyr-DTrp-Lys-Val-Cys]-Trp-NH$_2$

Dop6-Lys(Dop6)-Lys-DTyr-DTyr-cyclo[Cys-Tyr-DTrp-Lys-Val-Cys]-Trp-NH$_2$

Dop6-Lys(Dop6)-DTyr-DTyr-cyclo[Cys-Tyr-DTrp-Lys-Val-Cys]-Trp-NH$_2$

Dop7-Lys(Dop7)-DPhe-cyclo[Cys-Tyr-DTrp-Lys-Abu-Cys]-Thr-NH$_2$

Dop7-Lys(Dop7)-cyclo[Cys-Tyr-DTrp-Lys-Abu-Cys]-Thr-NH$_2$

Dop7-DLys(Dop7)-DPhe-cyclo[Cys-Tyr-DTrp-Lys-Abu-Cys]-Thr-NH$_2$

Dop7-DLys(Dop7)-cyclo[Cys-Tyr-DTrp-Lys-Abu-Cys]-Thr-NH$_2$

Dop7-Lys(Dop7)-D2Nal-cyclo[Cys-Tyr-DTrp-Lys-Val-Cys]-Thr-NH$_2$

Dop7-Lys(Dop7)-cyclo[Cys-Tyr-DTrp-Lys-Val-Cys]-Thr-NH$_2$

Dop7-Lys(Dop7)-DPhe-cyclo[Cys-Tyr-DTrp-Lys-Thr-Cys]-2Nal-NH$_2$

Dop7-Lys(Dop7)-cyclo[Cys-Tyr-DTrp-Lys-Thr-Cys]-2Nal-NH$_2$

Dop7-Lys(Dop7)-DPhe-cyclo[Cys-Phe-DTrp-Lys-Thr-Cys]-Thr-ol

Dop7-Lys(Dop7)-cyclo[Cys-Phe-DTrp-Lys-Thr-Cys]-Thr-ol

Dop7-Lys(Dop7)-DPhe-cyclo[Cys-Tyr-DTrp-Lys-Val-Cys]-Trp-NH$_2$

Dop7-Lys(Dop7)-cyclo[Cys-Tyr-DTrp-Lys-Val-Cys]-Trp-NH$_2$

Dop8-Lys(Dop8)-DPhe-cyclo[Cys-Tyr-DTrp-Lys-Abu-Cys]-Thr-NH$_2$

Dop8-Lys(Dop8)-cyclo[Cys-Tyr-DTrp-Lys-Abu-Cys]-Thr-NH$_2$

Dop8-DLys(Dop8)-DPhe-cyclo[Cys-Tyr-DTrp-Lys-Abu-Cys]-Thr-NH$_2$

Dop8-DLys(Dop8)-cyclo[Cys-Tyr-DTrp-Lys-Abu-Cys]-Thr-NH$_2$

Dop8-Lys(Dop8)-D2Nal-cyclo[Cys-Tyr-DTrp-Lys-Val-Cys]-Thr-NH$_2$

Dop8-Lys(Dop8)-cyclo[Cys-Tyr-DTrp-Lys-Val-Cys]-Thr-NH$_2$

Dop8-Lys(Dop8)-DPhe-cyclo[Cys-Tyr-DTrp-Lys-Thr-Cys]-2Nal-NH$_2$

Dop8-Lys(Dop8)-cyclo[Cys-Tyr-DTrp-Lys-Thr-Cys]-2Nal-NH$_2$

Dop8-Lys(Dop8)-DPhe-cyclo[Cys-Phe-DTrp-Lys-Thr-Cys]-Thr-ol

Dop8-Lys(Dop8)-cyclo[Cys-Phe-DTrp-Lys-Thr-Cys]-Thr-ol

Dop8-Lys(Dop8)-DPhe-cyclo[Cys-Tyr-DTrp-Lys-Val-Cys]-Trp-NH$_2$

Dop8-Lys(Dop8)-cyclo[Cys-Tyr-DTrp-Lys-Val-Cys]-Trp-NH$_2$

Dop9-Lys(Dop9)-DPhe-cyclo[Cys-Tyr-DTrp-Lys-Abu-Cys]-Thr-NH$_2$

Dop9-Lys(Dop9)-cyclo[Cys-Tyr-DTrp-Lys-Abu-Cys]-Thr-NH$_2$

Dop9-DLys(Dop9)-DPhe-cyclo[Cys-Tyr-DTrp-Lys-Abu-Cys]-Thr-NH$_2$

Dop9-DLys(Dop9)-cyclo[Cys-Tyr-DTrp-Lys-Abu-Cys]-Thr-NH$_2$

Dop9-Lys(Dop9)-D2Nal-cyclo[Cys-Tyr-DTrp-Lys-Val-Cys]-Thr-NH$_2$

Dop9-Lys(Dop9)-cyclo[Cys-Tyr-DTrp-Lys-Val-Cys]-Thr-NH$_2$

Dop9-Lys(Dop9)-DPhe-cyclo[Cys-Tyr-DTrp-Lys-Thr-Cys]-2Nal-NH$_2$

Dop9-Lys(Dop9)-cyclo[Cys-Tyr-DTrp-Lys-Thr-Cys]-2Nal-NH$_2$

Dop9-Lys(Dop9)-DPhe-cyclo[Cys-Phe-DTrp-Lys-Thr-Cys]-Thr-ol

Dop9-Lys(Dop9)-cyclo[Cys-Phe-DTrp-Lys-Thr-Cys]-Thr-ol

Dop9-Lys(Dop9)-DPhe-cyclo[Cys-Tyr-DTrp-Lys-Val-Cys]-Trp-NH$_2$

Dop9-Lys(Dop9)-cyclo[Cys-Tyr-DTrp-Lys-Val-Cys]-Trp-NH$_2$

Dop10-Lys(Dop10)-DPhe-cyclo[Cys-Tyr-DTrp-Lys-Abu-Cys]-Thr-NH$_2$

Dop10-Lys(Dop10)-cyclo[Cys-Tyr-DTrp-Lys-Abu-Cys]-Thr-NH$_2$

Dop10-DLys(Dop10)-DPhe-cyclo[Cys-Tyr-DTrp-Lys-Abu-Cys]-Thr-NH$_2$

Dop10-DLys(Dop10)-cyclo[Cys-Tyr-DTrp-Lys-Abu-Cys]-Thr-NH$_2$

Dop10-Lys(Dop10)-D2Nal-cyclo[Cys-Tyr-DTrp-Lys-Val-Cys]-Thr-NH$_2$

TABLE 1-continued

Dop10-Lys(Dop10)-cyclo[Cys-Tyr-DTrp-Lys-Val-Cys]-Thr-NH₂

Dop10-Lys(Dop10)-DPhe-cyclo[Cys-Tyr-DTrp-Lys-Thr-Cys]-2Nal-NH₂

Dop10-Lys(Dop10)-cyclo[Cys-Tyr-DTrp-Lys-Thr-Cys]-2Nal-NH₂

Dop10-Lys(Dop10)-DPhe-cyclo[Cys-IPhe-DTrp-Lys-Thr-Cys]-Thr-ol

Dop10-Lys(Dop10)-cyclo[Cys-Phe-DTrp-Lys-Thr-Cys]-Thr-ol

Dop10-Lys(Dop10)-DPhe-cyclo[Cys-Tyr-DTrp-Lys-Val-Cys]-Trp-NH₂

Dop10-Lys(Dop10)-cyclo[Cys-Tyr-DTrp-Lys-Val-Cys]-Trp-NH₂

Dop11-Lys(Dop11)-DPhe-cyclo[Cys-Tyr-DTrp-Lys-Abu-Cys]-Thr-NH₂

Dop11-Lys(Dop11)-cyclo[Cys-Tyr-DTrp-Lys-Abu-Cys]-Thr-NH₂

Dop11-DLys(Dop11)-DPhe-cyclo[Cys-Tyr-DTrp-Lys-Abu-Cys]-Thr-NH₂

Dop11-DLys(Dop11)-cyclo[Cys-Tyr-DTrp-Lys-Abu-Cys]-Thr-NH₂

Dop11-Lys(Dop11)-D2Nal-cyclo[Cys-Tyr-DTrp-Lys-Val-Cys]-Thr-NH₂

Dop11-Lys(Dop11)-cyclo[Cys-Tyr-DTrp-Lys-Val-Cys]-Thr-NH₂

Dop11-Lys(Dop11)-DPhe-cyclo[Cys-Tyr-DTrp-Lys-Thr-Cys]-2Nal-NH₂

Dop11-Lys(Dop11)-cyclo[Cys-Tyr-DTrp-Lys-Thr-Cys]-2Nal-NH₂

Dop11-Lys(Dop11)-DPhe-cyclo[Cys-Phe-DTrp-Lys-Thr-Cys]-Thr-ol

Dop11-Lys(Dop11)-cyclo[Cys-Phe-DTrp-Lys-Thr-Cys]-Thr-ol

Dop11-Lys(Dop11)-DPhe-cyclo[Cys-Tyr-DTrp-Lys-Val-Cys]-Trp-NH₂

Dop11-Lys(Dop11)-cyclo[Cys-Tyr-DTrp-Lys-Val-Cys]-Trp-NH₂

Dop12-Lys(Dop12)-DPhe-cyclo[Cys-Tyr-DTrp-Lys-Abu-Cys]-Thr-NH₂

Dop12-Lys(Dop12)-cyclo[Cys-Tyr-DTrp-Lys-Abu-Cys]-Thr-NH₂

Dop12-DLys(Dop12)-DPhe-cyclo[Cys-Tyr-DTrp-Lys-Abu-Cys]-Thr-NH₂

Dop12-DLys(Dop12)-cyclo[Cys-Tyr-DTrp-Lys-Abu-Cys]-Thr-NH₂

Dop12-Lys(Dop12)-D2Nal-cyclo[Cys-Tyr-DTrp-Lys-Val-Cys]-Thr-NH₂

Dop12-Lys(Dop12)-cyclo[Cys-Tyr-DTrp-Lys-Val-Cys]-Thr-NH₂

Dop12-Lys(Dop12)-DPhe-cyclo[Cys-Tyr-DTrp-Lys-Thr-Cys]-2Nal-NH₂

Dop12-Lys(Dop12)-cyclo[Cys-Tyr-DTrp-Lys-Thr-Cys]-2Nal-NH₂

Dop12-Lys(Dop12)-DPhe-cyclo[Cys-Phe-DTrp-Lys-Thr-Cys]-Thr-ol

Dop12-Lys(Dop12)-cyclo[Cys-Phe-DTrp-Lys-Thr-Cys]-Thr-ol

Dop12-Lys(Dop12)-DPhe-cyclo[Cys-Tyr-DTrp-Lys-Val-Cys]-Trp-NH₂

Dop12-Lys(Dop12)-cyclo[Cys-Tyr-DTrp-Lys-Val-Cys]-Trp-NH₂

Dop13-Lys(Dop13)-DPhe-cyclo[Cys-Tyr-DTrp-Lys-Abu-Cys]-Thr-NH₂

Dop13-Lys(Dop13)-cyclo[Cys-Tyr-DTrp-Lys-Abu-Cys]-Thr-NH₂

Dop13-DLys(Dop10)-DPhe-cyclo[Cys-Tyr-DTrp-Lys-Abu-Cys]-Thr-NH₂

Dop13-DLys(Dop13)-cyclo[Cys-Tyr-DTrp-Lys-Abu-Cys]-Thr-NH₂

Dop13-Lys(Dop13)-D2Nal-cyclo[Cys-Tyr-DTrp-Lys-Val-Cys]-Thr-NH₂

Dop13-Lys(Dop13)-cyclo[Cys-Tyr-DTrp-Lys-Val-Cys]-Thr-NH₂

Dop13-Lys(Dop13)-DPhe-cyclo[Cys-Tyr-DTrp-Lys-Thr-Cys]-2Nal-NH₂

Dop13-Lys(Dop13)-cyclo[Cys-Tyr-DTrp-Lys-Thr-Cys]-2Nal-NH₂

Dop13-Lys(Dop13)-DPhe-cyclo[Cys-Phe-DTrp-Lys-Thr-Cys]-Thr-ol

Dop13-Lys(Dop13)-cyclo[Cys-Phe-DTrp-Lys-Thr-Cys]-Thr-ol

Dop13-Lys(Dop13)-DPhe-cyclo[Cys-Tyr-DTrp-Lys-Val-Cys]-Trp-NH₂

Dop13-Lys(Dop13)-cyclo[Cys-Tyr-DTrp-Lys-Val-Cys]-Trp-NH₂

Dop1-Lys(Dop1)-Caeg-cyclo[DCys-3Pal-DTrp-Lys-DCys]-Thr(Bzl)-Tyr-NH₂

Dop1-Lys(Dop1)-Caeg-cyclo[DCys-Phe-DTrp-Lys-DCys]-Ser(Bzl)-Tyr-NH₂

Dop1-DLys(Dop1)-Caeg-cyclo[DCys-3Pal-DTrp-Lys-DCys]-Ser(Bzl)-Tyr-NH₂

Dop1-DLys(Dop1)-Caeg-cyclo[DCys-Phe-DTrp-Lys-DCys]-Ser(Bzl)-Tyr-NH₂

Dop1-DLys(Dop1)-Lys-Caeg-cyclo[DCys-3Pal-DTrp-Lys-DCys]-Thr(Bzl)-Tyr-NH₂

Dop1-DLys(Dop1)-Lys-Caeg-cyclo[DCys-Phe-DTrp-Lys-DCys]-Ser(Bzl)-Tyr-NH₂

Dop1-DLys(Dop1)-Lys-Caeg-cyclo[DCys-3Pal-DTrp-Lys-DCys]-Thr(Bzl)-Tyr-NH₂

Dop1-DLys(Dop1)-Lys-Caeg-cyclo[DCys-Phe-DTrp-Lys-DCys]-Ser(Bzl)-Tyr-NH₂

Dop1-Lys(Dop1)-Aepa-Caeg-cyclo[DCys-3Pal-DTrp-Lys-DCys]-Thr(Bzl)-Tyr-NH₂

TABLE 1-continued

Dop1-Lys(Dop1)-Aepa-Caeg-cyclo[DCys-Phe-DTrp-Lys-DCys]-Ser(Bzl)-Tyr-NH₂

Dop1-DLys(Dop1)-Aepa-Caeg-cyclo[DCys-3Pal-DTrp-Lys-DCys]-Thr(Bzl)-Tyr-NH₂

Dop1-DLys(Dop1)-Aepa-Caeg-cyclo[DCys-Phe-DTrp-Lys-DCys]-Ser(Bzl)-Tyr-NH₂

Dop1-Lys(Dop1)-Lys-Aepa-Caeg-cyclo[DCys-3Pal-DTrp-Lys-DCys]-Thr(Bzl)-Tyr-NH₂

Dop1-Lys(Dop1)-Lys-Aepa-Caeg-cyclo[DCys-Phe-DTrp-Lys-DCys]-Ser(Bzl)-Tyr-NH₂

Dop1-DLys(Dop1)-Lys-Aepa-Caeg-cyclo[DCys-3Pal-DTrp-Lys-DCys]-Thr(Bzl)-Tyr-NH₂

Dop1-DLys(Dop1)-Lys-Aepa-Caeg-cyclo[DCys-Phe-DTrp-Lys-DCys]-Ser(Bzl)-Tyr-NH₂

Dop2-Lys(Dop2)-Caeg-cyclo[DCys-3Pal-DTrp-Lys-DCys]-Thr(Bzl)-Tyr-NH₂

Dop2-Lys(Dop2)-Caeg-cyclo[DCys-Phe-DTrp-Lys-DCys]-Ser(Bzl)-Tyr-NH₂

Dop2-DLys(Dop2)-Caeg-cyclo[DCys-3Pal-DTrp-Lys-DCys]-Thr(Bzl)-Tyr-NH₂

Dop2-DLys(Dop2)-Caeg-cyclo[DCys-Phe-DTrp-Lys-DCys]-Ser(Bzl)-Tyr-NH₂

Dop2-Lys(Dop2)-Lys-Caeg-cyclo[DCys-3Pal-DTrp-Lys-DCys]-Thr(Bzl)-Tyr-NH₂

Dop2-Lys(Dop2)-Lys-Caeg-cyclo[DCys-Phe-DTrp-Lys-DCys]-Ser(Bzl)-Tyr-NH₂

Dop2-DLys(Dop2)-Lys-Caeg-cyclo[DCys-3Pal-DTrp-Lys-DCys]-Thr(Bzl)-Tyr-NH₂

Dop2-DLys(Dop2)-Lys-Caeg-cyclo[DCys-Phe-DTrp-Lys-DCys]-Ser(Bzl)-Tyr-NH₂

Dop2-Lys(Dop2)-Aepa-Caeg-cyclo[DCys-3Pal-DTrp-Lys-DCys]-Thr(Bzl)-Tyr-NH₂

Dop2-Lys(Dop2)-Aepa-Caeg-cyclo[DCys-Phe-DTrp-Lys-DCys]-Ser(Bzl)-Tyr-NH₂

Dop2-DLys(Dop2)-Aepa-Caeg-cyclo[DCys-3Pal-DTrp-Lys-DCys]-Thr(Bzl)-Tyr-NH₂

Dop2-DLys(Dop2)-Aepa-Caeg-cyclo[DCys-Phe-DTrp-Lys-DCys]-Ser(Bzl)-Tyr-NH₂

Dop2-Lys(Dop2)-Lys-Aepa-Caeg-cyclo[DCys-3Pal-DTrp-Lys-DCys]-Thr(Bzl)-Tyr-NH₂

Dop2-DLys(Dop2)-Lys-Aepa-Caeg-cyclo[DCys-Phe-DTrp-Lys-DCys]-Ser(Bzl)-Tyr-NH₂

Dop2-DLys(Dop2)-Lys-Aepa-Caeg-cyclo[DCys-3Pal-DTrp-Lys-DCys]-Thr(Bzl)-Tyr-NH₂

Dop2-DLys(Dop2)-Lys-Aepa-Caeg-cyclo[DCys-Phe-DTrp-Lys-DCys]-Ser(Bzl)-Tyr-NH₂

Dop3-Lys(Dop3)-Caeg-cyclo[DCys-3Pal-DTrp-Lys-DCys]-Thr(Bzl)-Tyr-NH₂

Dop3-Lys(Dop3)-Caeg-cyclo[DCys-Phe-DTrp-Lys-DCys]-Ser(Bzl)-Tyr-NH₂

Dop3-Lys(Dop3)-Lys-Caeg-cyclo[DCys-3Pal-DTrp-Lys-DCys]-Thr(Bzl)-Tyr-NH₂

Dop3-Lys(Dop3)-Lys-Caeg-cyclo[DCys-Phe-DTrp-Lys-DCys]-Ser(Bzl)-Tyr-NH₂

Dop3-Lys(Dop3)-Aepa-Caeg-cyclo[DCys-3Pal-DTrp-Lys-DCys]-Thr(Bzl)-Tyr-NH₂

Dop3-Lys(Dop3)-Aepa-Caeg-cyclo[DCys-Phe-DTrp-Lys-DCys]-Ser(Bzl)-Tyr-NH₂

Dop3-DLys(Dop3)-Caeg-cyclo[DCys-3Pal-DTrp-Lys-DCys]-Thr(Bzl)-Tyr-NH₂

Dop3-DLys(Dop3)-Caeg-cyclo[DCys-Phe-DTrp-Lys-DCys]-Ser(Bzl)-Tyr-NH₂

Dop3-DLys(Dop3)-Lys-Caeg-cyclo[DCys-3Pal-DTrp-Lys-DCys]-Thr(Bzl)-Tyr-NH₂

Dop3-DLys(Dop3)-Lys-Caeg-cyclo[DCys-Phe-DTrp-Lys-DCys]-Ser(Bzl)-Tyr-NH₂

Dop3-DLys(Dop3)-Aepa-Caeg-cyclo[DCys-3Pal-DTrp-Lys-DCys]-Thr(Bzl)-Tyr-NH₂

Dop3-DLys(Dop3)-Aepa-Caeg-cyclo[DCys-Phe-DTrp-Lys-DCys]-Ser(Bzl)-Tyr-NH₂

Dop4-Lys(Dop4)-Caeg-cyclo[DCys-3Pal-DTrp-Lys-DCys]-Thr(Bzl)-Tyr-NH₂

Dop4-Lys(Dop4)-Caeg-cyclo[DCys-Phe-DTrp-Lys-DCys]-Ser(Bzl)-Tyr-NH₂

Dop4-Lys(Dop4)-Lys-Caeg-cyclo[DCys-3Pal-DTrp-Lys-DCys]-Thr(Bzl)-Tyr-NH₂

Dop4-Lys(Dop4)-Lys-Caeg-cyclo[DCys-Phe-DTrp-Lys-DCys]-Ser(Bzl)-Tyr-NH₂

Dop4-Lys(Dop4)-Aepa-Caeg-cyclo[DCys-3Pal-DTrp-Lys-DCys]-Thr(Bzl)-Tyr-NH₂

Dop4-Lys(Dop4)-Aepa-Caeg-cyclo[DCys-Phe-DTrp-Lys-DCys]-Ser(Bzl)-Tyr-NH₂

Dop4-Lys(Dop4)-Lys-Aepa-Caeg-cyclo[DCys-3Pal-DTrp-Lys-DCys]-Thr(Bzl)-Tyr-NH₂

Dop4-Lys(Dop4)-Lys-Aepa-Caeg-cyclo[DCys-Phe-DTrp-Lys-DCys]-Ser(Bzl)-Tyr-NH₂

Dop4-DLys(Dop4)-Caeg-cyclo[DCys-3Pal-DTrp-Lys-DCys]-Thr(Bzl)-Tyr-NH₂

Dop4-DLys(Dop4)-Caeg-cyclo[DCys-Phe-DTrp-Lys-DCys]-Ser(Bzl)-Tyr-NH₂

Dop4-DLys(Dop4)-Lys-Caeg-cyclo[DCys-3Pal-DTrp-Lys-DCys]-Thr(Bzl)-Tyr-NH₂

Dop4-DLys(Dop4)-Lys-Caeg-cyclo[DCys-Phe-DTrp-Lys-DCys]-Ser(Bzl)-Tyr-NH₂

Dop4-DLys(Dop4)-Aepa-Caeg-cyclo[DCys-3Pal-DTrp-Lys-DCys]-Thr(Bzl)-Tyr-NH₂

Dop4-DLys(Dop4)-Aepa-Caeg-cyclo[DCys-Phe-DTrp-Lys-DCys]-Ser(Bzl)-Tyr-NH₂

Dop4-DLys(Dop4)-Lys-Aepa-Caeg-cyclo[DCys-3Pal-DTrp-Lys-DCys]-Thr(Bzl)-Tyr-NH₂

Dop4-DLys(Dop4)-Lys-Aepa-Caeg-cyclo[DCys-Phe-DTrp-Lys-DCys]-Ser(Bzl)-Tyr-NH₂

Dop5-Lys(Dop5)-Caeg-cyclo[DCys-3Pal-DTrp-Lys-DCys]-Thr(Bzl)-Tyr-NH₂

TABLE 1-continued

Dop5-Lys(Dop5)-Caeg-cyclo[DCys-Phe-DTrp-Lys-DCys]-Ser(Bzl)-Tyr-NH$_2$

Dop5-DLys(Dop5)-Caeg-cyclo[DCys-3Pal-DTrp-Lys-DCys]-Thr(Bzl)-Tyr-NH$_2$

Dop5-DLys(Dop5)-Caeg-cyclo[DCys-Phe-DTrp-Lys-DCys]-Ser(Bzl)-Tyr-NH$_2$

Dop5-Lys(Dop5)-Lys-Caeg-cyclo[DCys-3Pal-DTrp-Lys-DCys]-Thr(Bzl)-Tyr-NH$_2$

Dop5-Lys(Dop5)-Lys-Caeg-cyclo[DCys-Phe-DTrp-Lys-DCys]-Ser(Bzl)-Tyr-NH$_2$

Dop5-DLys(Dop5)-Lys-Caeg-cyclo[DCys-3Pal-DTrp-Lys-DCys]-Thr(Bzl)-Tyr-NH$_2$

Dop5-DLys(Dop5)-Lys-Caeg-cyclo[DCys-Phe-DTrp-Lys-DCys]-Ser(Bzl)-Tyr-NH$_2$

Dop6-Lys(Dop6)-Caeg-cyclo[DCys-3Pal-DTrp-Lys-DCys]-Thr(Bzl)-Tyr-NH$_2$

Dop6-Lys(Dop6)-Caeg-cyclo[DCys-Phe-DTrp-Lys-DCys]-Ser(Bzl)-Tyr-NH$_2$

Dop6-DLys(Dop6)-Caeg-cyclo[DCys-3Pal-DTrp-Lys-DCys]-Thr(Bzl)-Tyr-NH$_2$

Dop6-DLys(Dop6)-Caeg-cyclo[DCys-3Pal-DTrp-Lys-DCys]-Thr(Bzl)-Tyr-NH$_2$

Dop6-Lys(Dop6)-Lys-Caeg-cyclo[DCys-3Pal-DTrp-Lys-DCys]-Thr(Bzl)-Tyr-NH$_2$

Dop6-Lys(Dop6)-Lys-Caeg-cyclo[DCys-Phe-DTrp-Lys-DCys]-Thr(Bzl)-Tyr-NH$_2$

Dop6-DLys(Dop6)-Lys-Caeg-cyclo[DCys-3Pal-DTrp-Lys-DCys]-Thr(Bzl)-Tyr-NH$_2$

Dop6-DLys(Dop6)-Lys-Caeg-cyclo[DCys-Phe-DTrp-Lys-DCys]-Ser(Bzl)-Tyr-NH$_2$

Dop7-Lys(Dop7)-Caeg-cyclo[DCys-3Pal-DTrp-Lys-DCys]-Thr(Bzl)-Tyr-NH$_2$

Dop7-Lys(Dop7)-Caeg-cyclo[DCys-Phe-DTrp-Lys-DCys]-Ser(Bzl)-Tyr-NH$_2$

Dop7-Lys(Dop7)-Lys-Caeg-cyclo[DCys-3Pal-DTrp-Lys-DCys]-Thr(Bzl)-Tyr-NH$_2$

Dop7-Lys(Dop7)-Lys-Caeg-cyclo[DCys-Phe-DTrp-Lys-DCys]-Ser(Bzl)-Tyr-NH$_2$

Dop8-Lys(Dop8)-Caeg-cyclo[DCys-3Pal-DTrp-Lys-DCys]-Thr(Bzl)-Tyr-NH$_2$

Dop8-Lys(Dop8)-Caeg-cyclo[DCys-Phe-DTrp-Lys-DCys]-Ser(Bzl)-Tyr-NH$_2$

Dop8-Lys(Dop8)-Lys-Caeg-cyclo[DCys-3Pal-DTrp-Lys-DCys]-Thr(Bzl)-Tyr-NH$_2$

Dop8-Lys(Dop8)-Lys-Caeg-cyclo[DCys-Phe-DTrp-Lys-DCys]-Ser(Bzl)-Tyr-NH$_2$

Dop9-Lys(Dop9)-Caeg-cyclo[DCys-3Pal-DTrp-Lys-DCys]-Thr(Bzl)-Tyr-NH$_2$

Dop9-Lys(Dop9)-Caeg-cyclo[DCys-Phe-DTrp-Lys-DCys]-Ser(Bzl)-Tyr-NH$_2$

Dop9-Lys(Dop9)-Lys-Caeg-cyclo[DCys-3Pal-DTrp-Lys-DCys]-Thr(Bzl)-Tyr-NH$_2$

TABLE 1-continued

Dop9-Lys(Dop9)-Lys-Caeg-cyclo[DCys-Phe-DTrp-Lys-DCys]-Ser(Bzl)-Tyr-NH$_2$

Dop10-Lys(Dop10)-Caeg-cyclo[DCys-3Pal-DTrp-Lys-DCys]-Thr(Bzl)-Tyr-NH$_2$

Dop10-Lys(Dop10)-Caeg-cyclo[DCys-Phe-DTrp-Lys-DCys]-Ser(Bzl)-Tyr-NH$_2$

Dop10-Lys(Dop10)-Lys-Caeg-cyclo[DCys-3Pal-DTrp-Lys-DCys]-Thr(Bzl)-Tyr-NH$_2$

Dop10-Lys(Dop10)-Lys-Caeg-cyclo[DCys-Phe-DTrp-Lys-DCys]-Ser(Bzl)-Tyr-NH$_2$

Dop11-Lys(Dop11)-Caeg-cyclo[DCys-3Pal-DTrp-Lys-DCys]-Thr(Bzl)-Tyr-NH$_2$

Dop11-Lys(Dop11)-Caeg-cyclo[DCys-Phe-DTrp-Lys-DCys]-Ser(Bzl)-Tyr-NH$_2$

Dop11-Lys(Dop11)-Lys-Caeg-cyclo[DCys-3Pal-DTrp-Lys-DCys]-Thr(Bzl)-Tyr-NH$_2$

Dop11-Lys(Dop11)-Lys-Caeg-cyclo[DCys-Phe-DTrp-Lys-DCys]-Ser(Bzl)-Tyr-NH$_2$

Dop12-Lys(Dop12)-Caeg-cyclo[DCys-3Pal-DTrp-Lys-DCys]-Thr(Bzl)-Tyr-NH$_2$

Dop12-Lys(Dop12)-Caeg-cyclo[DCys-Phe-DTrp-Lys-DCys]-Ser(Bzl)-Tyr-NH$_2$

Dop12-Lys(Dop12)-Lys-Caeg-cyclo[DCys-3Pal-DTrp-Lys-DCys]-Thr(Bzl)-Tyr-NH$_2$

Dop12-Lys(Dop12)-Lys-Caeg-cyclo[DCys-Phe-DTrp-Lys-DCys]-Ser(Bzl)-Tyr-NH$_2$

Dop13-Lys(Dop13)-Caeg-cyclo[DCys-3Pal-DTrp-Lys-DCys]-Thr(Bzl)-Tyr-NH$_2$

Dop13-Lys(Dop13)-Caeg-cyclo[DCys-Phe-DTrp-Lys-DCys]-Ser(Bzl)-Tyr-NN$_2$

Dop13-Lys(Dop13)-Lys-Caeg-cyclo[DCys-3Pal-DTrp-Lys-DCys]-Thr(Bzl)-Tyr-NH$_2$

Dop13-Lys(Dop13)-Lys-Caeg-cyclo[DCys-Phe-DTrp-Lys-DCys]-Ser(Bzl)-Tyr-NH$_2$

Dop1-Lys(Dop1)-cyclo[Cys-Phe-Phe-DTrp-Lys-Thr-Phe-Cys]-NH$_2$

Dop1-Lys(Dop1)-DPhe-cyclo[Cys-Phe-(N-Me)DTrp-Lys-Thr-Cys]-Thr-NH$_2$

Dop1-DLys(Dop1)-cyclo[Cys-Phe-Phe-DTrp-Lys-Thr-Phe-Cys]-NH$_2$

Dop1-DLys(Dop1)-DPhe-cyclo[Cys-Phe-(N-Me)DTrp-Lys-Thr-Cys]-Thr-NH$_2$

Dop1-Lys(Dop1)-cyclo[Cys-Phe-(N-Me)DTrp-Lys-Thr-Cys]-Thr-NH$_2$

Dop1-DLys(Dop1)-cyclo[Cys-Phe-(N-Me)DTrp-Lys-Thr-Cys]-Thr-NH$_2$

Dop2-Lys(Dop2)-cyclo[Cys-Phe-Phe-DTrp-Lys-Thr-Phe-Cys]-NH$_2$

Dop2-Lys(Dop2)-DPhe-cyclo[Cys-Phe-(N-Me)DTrp-Lys-Thr-Cys]Thr-NH$_2$

Dop2-DLys(Dop2)-cyclo[Cys-Phe-Phe-DTrp-Lys-Thr-Phe-Cys]-NH$_2$

TABLE 1-continued

Dop2-DLys(Dop2)-DPhe-cyclo[Cys-Phe-(N-Me)DTrp-Lys-Thr-Cys]-Thr-NH$_2$

Dop2-Lys(Dop2)-cyclo[Cys-Phe-(N-Me)DTrp-Lys-Thr-Cys]-Thr-NH$_2$

Dop2-DLys(Dop2)-cyclo[Cys-Phe-(N-Me)DTrp-Lys-Thr-Cys]-Thr-NH$_2$

Dop3-Lys(Dop3)-cyclo[Cys-Phe-Phe-DTrp-Lys-Thr-Phe-Cys]-NH$_2$

Dop3-Lys(Dop3)-DPhe-cyclo[Cys-Phe-(N-Me)DTrp-Lys-Thr-Cys]-Thr-NH$_2$

Dop3-Lys(Dop3)-cyclo[Cys-Phe-(N-Me)DTrp-Lys-Thr-Cys]-Thr-NH$_2$

Dop4-Lys(Dop4)-cyclo[Cys-Phe-Phe-DTrp-Lys-Thr-Phe-Cys-NH$_2$

Dop4-Lys(Dop4)-DPhe-cyclo[Cys-Phe-(N-Me)DTrp-Lys-Thr-Cys]-Thr-NH$_2$

Dop4-Lys(Dop4)-cyclo[Cys-Phe-(N-Me)DTrp-Lys-Thr-Cys]-Thr-NH$_2$

Dop5-Lys(Dop5)-cyclo[Cys-Phe-Phe-DTrp-Lys-Thr-Phe-Cys]-NH$_2$

Dop5-Lys(Dop5)-DPhe-cyclo[Cys-Phe-(N-Me)DTrp-Lys-Thr-Cys]-Thr-NH$_2$

Dop5-DLys(Dop5)-cyclo[Cys-Phe-Phe-DTrp-Lys-Thr-Phe-Cys]-NH$_2$

Dop5-DLys(Dop5)-DPhe-cyclo[Cys-Phe-(N-Me)DTrp-Lys-Thr-Cys]-Thr-NH$_2$

Dop5-Lys(Dop5)-cyclo[Cys-Phe-(N-Me)DTrp-Lys-Thr-Cys]-Thr-NH$_2$

Dop5-DLys(Dop5)-cyclo[Cys-Phe-(N-Me)DTrp-Lys-Thr-Cys]-Thr-NH$_2$

Dop6-Lys(Dop6)-cyclo[Cys-Phe-Phe-DTrp-Lys-Thr-Phe-Cys]-NH$_2$

Dop6-Lys(Dop6)-DPhe-cyclo[Cys-Phe-(N-Me)DTrp-Lys-Thr-Cys]-Thr-NH$_2$

Dop6-DLys(Dop6)-cyclo[Cys-Phe-Phe-DTrp-Lys-Thr-Phe-Cys]-NH$_2$

Dop6-DLys(Dop6)-DPhe-cyclo[Cys-Phe-(N-Me)DTrp-Lys-Thr-Cys]-Thr-NH$_2$

Dop6-Lys(Dop6)-cyclo[Cys-Phe-(N-Me)DTrp-Lys-Thr-Cys]-Thr-NH$_2$

Dop6-DLys(Dop6)-cyclo[Cys-Phe-(N-Me)DTrp-Lys-Thr-Cys]-Thr-NH$_2$

Dop7-Lys(Dop7)-cyclo[Cys-Phe-Phe-DTrp-Lys-Thr-Phe-Cys]-NH$_2$

Dop7-Lys(Dop7)-DPhe-cyclo[Cys-Phe-(N-Me)DTrp-Lys-Thr-Cys]-Thr-NH$_2$

Dop7-Lys(Dop7)-cyclo[Cys-Phe-(N-Me)DTrp-Lys-Thr-Cys]-Thr-NH$_2$

Dop8-Lys(Dop8)-cyclo[Cys-Phe-Phe-DTrp-Lys-Thr-Phe-Cys]-NH$_2$

Dop8-Lys(Dop8)-DPhe-cyclo[Cys-Phe-(N-Me)DTrp-Lys-Thr-Cys]-Thr-NH$_2$

Dop9-Lys(Dop9)-cyclo[Cys-Phe-Phe-DTrp-Lys-Thr-Phe-Cys]-NH$_2$

Dop9-Lys(Dop9)-DPhe-cyclo[Cys-Phe-(N-Me)DTrp-Lys-Thr-Cys]-Thr-NH$_2$

Dop10-Lys(Dop10)-cyclo[Cys-Phe-Phe-DTrp-Lys-Thr-Phe-Cys]-NH$_2$

Dop10-Lys(Dop10)-DPhe-cyclo[Cys-Phe-(N-Me)DTrp-Lys-Thr-Cys]-Thr-NH$_2$

Dop11-Lys(Dop11)-cyclo[Cys-Phe-Phe-DTrp-Lys-Thr-Phe-Cys]-NH$_2$

Dop11-Lys(Dop11)-DPhe-cyclo[Cys-Phe-(N-Me)DTrp-Lys-Thr-Cys]-Thr-NH$_2$

Dop12-Lys(Dop12)-cyclo[Cys-Phe-Phe-DTrp-Lys-Thr-Phe-Cys]-NH$_2$

Dop12-Lys(Dop12)-DPhe-cyclo[Cys-Phe-(N-Me)DTrp-Lys-Thr-Cys]-Thr-NH$_2$

Dop13-Lys(Dop13)-cyclo[Cys-Phe-Phe-DTrp-Lys-Thr-Phe-Cys]-NH$_2$

Dop13-Lys(Dop13)-DPhe-cyclo[Cys-Phe-(N-Me)DTrp-Lys-Thr-Cys]-Thr-NH$_2$

Dop1-DPhe-cyclo[Cys-3ITyr(Dop1)-DTrp-Lys-Val-Cys]-Thr-NH$_2$

Dop1-DPhe-Doc-DPhe-cyclo[Cys-3ITyr(Dop1)-DTrp-Lys-Val-Cys]-Thr-NH$_2$

Dop1-DLys(Dop1)-DPhe-cyclo[Cys-3ITyr-DTrp-Lys-Thr-Cys-Thr-NH$_2$

Dop1-DLys(Dop1)-Aepa-DPhe-cyclo[Cys-3ITyr-DTrp-Lys-Thr-Cys]-Thr-NH$_2$

Dop1-Lys(Dop1)-DTyr-DTyr-cyclo[Cys-3ITyr-DTrp-Lys-Thr-Cys]-Thr-NH$_2$

Dop1-Lys(Dop1)-DPhe-cyclo[Cys-3ITyr-DTrp-Lys-Thr-Cys]-Thr-NH$_2$

Dop1-Lys(Dop1)-Aepa-DPhe-cyclo[Cys-3ITyr-DTrp-Lys-Thr-Cys]-Thr-NH$_2$

Dop1-DLys(Dop1)-cyclo[Cys-3ITyr-DTrp-Lys-Thr-Cys]-Thr-NH$_2$

Dop1-Lys(Dop1)-cyclo[Cys-3ITyr-DTrp-Lys-Thr-Cys]-Thr-NH$_2$

Dop1-Lys(Dop1)-Lys-DTyr-DTyr-cyclo[Cys-3ITyr-DTrp-Lys-Thr-Cys]-Thr-NH$_2$

Dop1-DLys(Dop1)-DTyr-DTyr-cyclo[Cys-3ITyr-DTrp-Lys-Thr-Cys]-Thr-NH$_2$

Dop1-DLys(Dop1)-Lys-DTyr-DTyr-cyclo[Cys-3ITyr-DTrp-Lys-Thr-Cys]-Thr-NH$_2$

Dop1-DLys(Dop1)-DPhe-cyclo[Cys-3ITyr-DTrp-Lys-Abu-Cys]-Thr-NH$_2$

Dop1-DLys(Dop1)-Aepa-DPhe-cyclo[Cys-3ITyr-DTrp-Lys-Abu-Cys]-Thr-NH$_2$

Dop1-Lys(Dop1)-DTyr-DTyr-cyclo[Cys-3ITyr-DTrp-Lys-Abu-Cys]-Thr-NH$_2$

Dop1-Lys(Dop1)-DPhe-cyclo[Cys-3ITyr-DTrp-Lys-Abu-Cys]-Thr-NH$_2$

TABLE 1-continued

Dop1-Lys(Dop1)-Aepa-DPhe-cyclo[Cys-3ITyr-DTrp-Lys-Abu-Cys]-Thr-NH$_2$

Dop1-DLys(Dop1)-cyclo[Cys-3ITyr-DTrp-Lys-Abu-Cys]-Thr-NH$_2$

Dop1-Lys(Dop1)-cyclo[Cys-3ITyr-DTrp-Lys-Abu-Cys]-Thr-NH$_2$

Dop1-Lys(Dop1)-Lys-DTyr-DTyr-cyclo[Cys-3ITyr-DTrp-Lys-Abu-Cys]-Thr-NH$_2$

Dop1-DLys(Dop1)-DTyr-DTyr-cyclo[Cys-3ITyr-DTrp-Lys-Abu-Cys]-Thr-NH$_2$

Dop1-DLys(Dop1)-Lys-DTyr-DTyr-cyclo[Cys-3ITyr-DTrp-Lys-Abu-Cys]-Thr-NH$_2$

Dop1-DLys(Dop1)-DPhe-cyclo[Cys-3ITyr-DTrp-Lys-Val-Cys]-Thr-NH$_2$

Dop1-DLys(Dop1)-Aepa-DPhe-cyclo[Cys-3ITyr-DTrp-Lys-Val-Cys]-Thr-NH$_2$

Dop1-Lys(Dop1)-DTyr-DTyr-cyclo[Cys-3ITyr-DTrp-Lys-Val-Cys]-Thr-NH$_2$

Dop1-Lys(Dop1)-DPhe-cyclo[Cys-3ITyr-DTrp-Lys-Val-Cys]-Thr-NH$_2$

Dop1-Lys(Dop1)-Aepa-DPhe-cyclo[Cys-3ITyr-DTrp-Lys-Val-Cys]-Thr-NH$_2$

Dop1-DLys(Dop1)-cyclo[Cys-3ITyr-DTrp-Lys-Val-Cys]-Thr-NH$_2$

Dop1-Lys(Dop1)-cyclo[Cys-3ITyr-DTrp-Lys-Val-Cys]-Thr-NH$_2$

Dop1-Lys(Dop1)-Lys-DTyr-DTyr-cyclo[Cys-3ITyr-DTrp-Lys-Val-Cys]-Thr-NH$_2$

Dop1-DLys(Dop1)-DTyr-DTyr-cyclo[Cys-3ITyr-DTrp-Lys-Val-Cys]-Thr-NH$_2$

Dop1-DLys(Dop1)-Lys-DTyr-DTyr-cyclo[Cys-3ITyr-DTrp-Lys-Val-Cys]-Thr-NH$_2$

Dop2-DPhe-cyclo[Cys-3ITyr(Dop2)-DTrp-Lys-Val-Cys]-Thr-NH$_2$

Dop2-Lys(Dop2)-DTyr-DTyr-cyclo[Cys-3ITyr-DTrp-Lys-Thr-Cys]-Thr-NH$_2$

Dop2-Lys(Dop2)-Aepa-DTyr-DTyr-cyclo[Cys-3ITyr-DTrp-Lys-Thr-Cys]-Thr-NH$_2$

Dop2-Lys(Dop2)-DPhe-cyclo[Cys-3ITyr-DTrp-Lys-Thr-Cys]-Thr-NH$_2$

Dop2-Lys(Dop2)-Aepa-DPhe-cyclo[Cys-3ITyr-DTrp-Lys-Thr-Cys]-Thr-NH$_2$

Dop2-DLys(Dop2)-DPhe-cyclo[Cys-3ITyr-DTrp-Lys-Thr-Cys]-Thr-NH$_2$ Example 1

Dop2-DLys(Dop2)-Aepa-DPhe-cyclo[Cys-3ITyr-DTrp-Lys-Thr-Cys]-Thr-NH$_2$

Dop2-DLys(Dop2)-cyclo[Cys-3ITyr-DTrp-Lys-Thr-Cys]-Thr-NH$_2$

Dop2-Lys(Dop2)-cyclo[Cys-3ITyr-DTrp-Lys-Thr-Cys]-Thr-NH$_2$

Dop2-Lys(Dop2)-Lys-DTyr-DTyr-cyclo[Cys-3ITyr-DTrp-Lys-Thr-Cys]-Thr-NH$_2$

Dop2-DLys(Dop2)-DTyr-DTyr-cyclo[Cys-3ITyr-DTrp-Lys-Thr-Cys]-Thr-NH$_2$

Dop2-DLys(Dop2)-Aepa-DTyr-DTyr-cyclo[Cys-3ITyr-DTrp-Lys-Thr-Cys]-Thr-NH$_2$

Dop2-DLys(Dop2)-Lys-DTyr-DTyr-cyclo[Cys-3ITyr-DTrp-Lys-Thr-Cys]-Thr-NH$_2$

Dop2-DLys(Dop2)-DPhe-cyclo[Cys-3ITyr-DTrp-Lys-Abu-Cys]-Thr-NH$_2$

Dop2-DLys(Dop2)-Aepa-DPhe-cyclo[Cys-3ITyr-DTrp-Lys-Abu-Cys]-Thr-NH$_2$

Dop2-Lys(Dop2)-DTyr-DTyr-cyclo[Cys-3ITyr-DTrp-Lys-Abu-Cys]-Thr-NH$_2$

Dop2-Lys(Dop2)-DPhe-cyclo[Cys-3ITyr-DTrp-Lys-Abu-Cys]-Thr-NH$_2$

Dop2-Lys(Dop2)-Aepa-DPhe-cyclo[Cys-3ITyr-DTrp-Lys-Abu-Cys]-Thr-NH$_2$

Dop2-DLys(Dop2)-cyclo[Cys-3ITyr-DTrp-Lys-Abu-Cys]-Thr-NH$_2$

Dop2-Lys(Dop2)-cyclo[Cys-3ITyr-DTrp-Lys-Abu-Cys]-Thr-NH$_2$

Dop2-Lys(Dop2)-Lys-DTyr-DTyr-cyclo[Cys-3ITyr-DTrp-Lys-Abu-Cys]-Thr-NH$_2$

Dop2-DLys(Dop2)-DTyr-DTyr-cyclo[Cys-3ITyr-DTrp-Lys-Abu-Cys]-Thr-NH$_2$

Dop2-DLys(Dop2)-Lys-DTyr-DTyr-cyclo[Cys-3ITyr-DTrp-Lys-Abu-Cys]-Thr-NH$_2$

Dop2-DLys(Dop2)-DPhe-cyclo[Cys-3ITyr-DTrp-Lys-Val-Cys]-Thr-NH$_2$

Dop2-DLys(Dop2)-Aepa-DPhe-cyclo[Cys-3ITyr-DTrp-Lys-Val-Cys]-Thr-NH$_2$

Dop2-Lys(Dop2)-DTyr-DTyr-cyclo[Cys-3ITyr-DTrp-Lys-Val-Cys]-Thr-NH$_2$

Dop2-Lys(Dop2)-DPhe-cyclo[Cys-3ITyr-DTrp-Lys-Val-Cys]-Thr-NH$_2$

Dop2-Lys(Dop2)-Aepa-DPhe-cyclo[Cys-3ITyr-DTrp-Lys-Val-Cys]-Thr-NH$_2$

Dop2-DLys(Dop2)-cyclo[Cys-3ITyr-DTrp-Lys-Val-Cys]-Thr-NH$_2$

Dop2-Lys(Dop2)-cyclo[Cys-3ITyr-DTrp-Lys-Val-Cys]-Thr-NH$_2$

Dop2-Lys(Dop2)Lys-DTyr-DTyr-cyclo[Cys-3ITy-DTrp-Lys-Val-Cys]-Thr-NH$_2$

Dop2-DLys(Dop2)-DTyr-DTyr-cyclo[Cys-3ITyr-DTrp-Lys-Val-Cys]-Thr-NH$_2$

Dop2-DLys(Dop2)-Lys-DTyr-DTyr-cyclo[Cys-3ITyr-DTrp-Lys-Val-Cys]-Thr-NH$_2$

Dop3-Lys(Dop3)-DPhe-cyclo[Cys-3ITyr-DTrp-Lys-Thr-Cys]-Thr-NH$_2$

Dop4-Lys(Dop4)-DPhe-cyclo[Cys-3ITyr-DTrp-Lys-Thr-Cys]-Thr-NH$_2$

Dop3-Lys(Dop3)-Aepa-DPhe-cyclo[Cys-3ITyr-DTrp-Lys-Thr-Cys]-Thr-NH$_2$

TABLE 1-continued

Dop4-Lys(Dop4)-Aepa-DPhe-cyclo[Cys-3ITyr-DTrp-Lys-Thr-Cys]-Thr-NH$_2$

Dop5-DLys(Dop5)-DPhe-cyclo[Cys-3ITyr-DTrp-Lys-Thr-Cys]-Thr-NH$_2$

Dop5-Lys(Dop5)-DTyr-DTyr-cyclo[Cys-3ITyr-DTrp-Lys-Thr-Cys]-Thr-NH$_2$

Dop5-Lys(Dop5)-DPhe-cyclo[Cys-3ITyr-DTrp-Lys-Thr-Cys]-Thr-NH$_2$

Dop5-DLys(Dop5)-cyclo[Cys-3ITyr-DTrp-Lys-Thr-Cys]-Thr-NH$_2$

Dop5-Lys(Dop5)-cyclo[Cys-3ITyr-DTrp-Lys-Thr-Cys]-Thr-NH$_2$

Dop5-Lys(Dop5)-Lys-DTyr-DTyr-cyclo[Cys-3ITyr-DTrp-Lys-Thr-Cys]-Thr-NH$_2$

Dop5-DLys(Dop5)-DTyr-DTyr-cyclo[Cys-3ITyr-DTrp-Lys-Thr-Cys]-Thr-NH$_2$

Dop5-DLys(Dop5)-Lys-DTyr-DTyr-cyclo[Cys-3ITyr-DTrp-Lys-Thr-Cys]-Thr-NH$_2$

Dop5-DLys(Dop5)-DPhe-cyclo[Cys-3ITyr-DTrp-Lys-Abu-Cys]-Thr-NH$_2$

Dop5-Lys(Dop5)-DTyr-DTyr-cyclo[Cys-3ITyr-DTrp-Lys-Abu-Cys]-Thr-NH$_2$

Dop5-Lys(Dop5)-DPhe-cyclo[Cys-3ITyr-DTrp-Lys-Abu-Cys]-Thr-NH$_2$

Dop5-DLys(Dop5)-cyclo[Cys-3ITyr-DTrp-Lys-Abu-Cys]-Thr-NH$_2$

Dop5-Lys(Dop5)-cyclo[Cys-3ITyr-DTrp-Lys-Abu-Cys]-Thr-NH$_2$

Dop5-Lys(Dop5)-Lys-DTyr-DTyr-cyclo[Cys-3ITyr-DTrp-Lys-Abu-Cys]-Thr-NH$_2$

Dop5-DLys(Dop5)-DTyr-DTyr-cyclo[Cys-3ITyr-DTrp-Lys-Abu-Cys]-Thr-NH$_2$

Dop5-DLys(Dop5)-Lys-DTyr-DTyr-cyclo[Cys-3ITyr-DTrp-Lys-Abu-Cys]-Thr-NH$_2$

Dop5-DLys(Dop5)-DPhe-cyclo[Cys-3ITyr-DTrp-Lys-Val-Cys]-Thr-NH$_2$

Dop5-Lys(Dop5)-DTyr-DTyr-cyclo[Cys-3ITyr-DTrp-Lys-Val-Cys]-Thr-NH$_2$

Dop5-Lys(Dop5)-DPhe-cyclo[Cys-3ITyr-DTrp-Lys-Val-Cys]-Thr-NH$_2$

Dop5-DLys(Dop5)-cyclo[Cys-3ITyr-DTrp-Lys-Val-Cys]-Thr-NH$_2$

Dop5-Lys(Dop5)-cyclo[Cys-3ITyr-DTrp-Lys-Val-Cys]-Thr-NH$_2$

Dop5-Lys(Dop5)-Lys-DTyr-DTyr-cyclo[Cys-3ITyr-DTrp-Lys-Val-Cys]-Thr-NH$_2$

Dop5-DLys(Dop5)-DTyr-DTyr-cyclo[Cys-3ITyr-DTrp-Lys-Val-Cys]-Thr-NH$_2$

Dop5-DLys(Dop5)-Lys-DTyr-DTyr-cyclo[Cys-3ITyr-DTrp-Lys-Val-Cys]-Thr-NH$_2$

Dop6-Lys(Dop6)-cyclo[Cys-3ITyr-DTrp-Lys-Thr-Cys]-Thr-NH$_2$

Dop7-Lys(Dop7)-cyclo[Cys-3ITyr-DTrp-Lys-Thr-Cys]-Thr-NH$_2$

Dop8-Lys(Dop8)-cyclo[Cys-3ITyr-DTrp-Lys-Thr-Cys]-Thr-NH$_2$

Dop9-Lys(Dop9)-cyclo[Cys-3ITyr-DTrp-Lys-Thr-Cys]-Thr-NH$_2$

Dop10-Lys(Dop10)-cyclo[Cys-3ITyr-DTrp-Lys-Thr-Cys]-Thr-NH$_2$

Dop11-Lys(Dop11)-cyclo[Cys-3ITyr-DTrp-Lys-Thr-Cys]-Thr-NH$_2$

Dop12-Lys(Dop12)-cyclo[Cys-3ITyr-DTrp-Lys-Thr-Cys]-Thr-NH$_2$

Dop13-Lys(Dop13)-cyclo[Cys-3ITyr-DTrp-Lys-Thr-Cys]-Thr-NH$_2$

Dop6-Lys(Dop6)-DPhe-cyclo[Cys-3ITyr-DTrp-Lys-Thr-Cys]-Thr-NH$_2$

Dop7-Lys(Dop7)-DPhe-cyclo[Cys-3ITyr-DTrp-Lys-Thr-Cys]-Thr-NH$_2$

Dop8-Lys(Dop8)-DPhe-cyclo[Cys-3ITyr-DTrp-Lys-Thr-Cys]-Thr-NH$_2$

Dop9-Lys(Dop9)-DPhe-cyclo[Cys-3ITyr-DTrp-Lys-Thr-Cys]-Thr-NH$_2$

Dop10-Lys(Dop10)-DPhe-cyclo[Cys-3ITyr-DTrp-Lys-Thr-Cys]-Thr-NH$_2$

Dop11-Lys(Dop11)-DPhe-cyclo[Cys-3ITyr-DTrp-Lys-Thr-Cys]-Thr-NH$_2$

Dop12-Lys(Dop12)-DPhe-cyclo[Cys-3ITyr-DTrp-Lys-Thr-Cys]-Thr-NH$_2$

Dop13-Lys(Dop13)-DPhe-cyclo[Cys-3ITyr-DTrp-Lys-Thr-Cys]-Thr-NH$_2$

Some of the compounds of the instant invention have at least one asymmetric center. Additional asymmetric centers may be present in the molecule depending upon the nature of the various substituents of the molecule. Each such asymmetric center will produce two optical isomers and it is intended that all such optical isomers, as separated, pure or partially purified optical isomers, racemic mixtures or diastereomeric mixtures thereof, are included within the scope of the instant invention.

The compounds of the instant invention generally can be provided in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts can be formed by taking about 1 equivalent of a compound of the invention and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention features pharmaceutical compositions comprising, as an active ingredient, at least one compound of the invention in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dose of an active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

Preferred dosage ranges are from 0.01 to 10.0 mg/kg of body weight. Such dosages may be administered, for example, daily as a single dose or divided into multiple doses.

Somatostatin Receptor Specificity and Selectivity Assay

Specificity and selectivity of the somatostatin analogues used to synthesize the somatostatin-dopamine chimers was determined by a radioligand binding assay on CHO-K1 cells stably transfected with each of the SSTR subtypes, as follows. Somatostatin analogs are also described in U.S. Patent Application Publication No. 02210006790. The complete coding sequences of genomic fragments of the SSTR 1 (e.g., Genbank accession No. M81829), SSTR 2 (e.g., Genbank accession No. M81830), SSTR 3 (e.g., Genbank accession No. L07062), and SSTR 4 (e.g., Genbank accession No. AL049651) genes and a cDNA clone for SSTR 5 (e.g., Genbank accession No. D16827) was subcloned into the mammalian expression vector pCMV (Life Technologies, Milano, Italy). Other SSTR sequences are known to the skilled artisan. Clonal cell lines stably expressing SSTR's 1-5 were obtained by transfection into CHO-K1 cells (ATCC, Manassas, Va., USA) using the calcium phosphate co-precipitation method (Davis L, et al., 1994 In: Basic methods in Molecular Biology, 2nd edition, Appleton & Lange, Norwalk, Conn., USA: 611-646). The plasmid pRSV-neo (ATCC) was included as a selectable marker. Clonal cell lines were selected in RPMI 1640 media containing 0.5 mg/ml of G418 (Life Technologies, Milano, Italy), ring cloned, and expanded into culture.

Membranes for in vitro receptor binding assays were obtained by homogenizing the CHO-K1 cells expressing the SSTR's subtypes in ice-cold 50 mM Tris-HCl and centrifuging twice at 39000 g (10 min), with an intermediate resuspension in fresh buffer. The final pellets were resuspended in 10 mM Tris-HCl for assay.

For the SSTR 1, 3, 4, and 5 assays, aliquots of the membrane preparations were incubated 90 minutes at 25° C. with 0.05 nM $[^{125}I$-Tyr11]SS-14 in 50 mM HEPES (pH 7.4) containing 10 mg/ml bovine serum albumin (BSA), 5 mM $MgCl_2$, 200 KIU/ml Trasylol, 0.02 mg/ml bacitracin, and 0.02 mg/ml phenylmethylsuphonyl fluoride. The final assay volume was 0.3 ml.

For the SSTR 2 assay, 0.05 nM $[^{125}I]$MK-678 was employed as the radioligand and the incubation time was 90 minutes at 25° C. The incubations were terminated by rapid filtration through GF/C glass microfibre filters (Whatman Co.) (pre-soaked in 0.3% polyethylenimine) using a BRANDEL filtration manifold. Each tube and filter was washed three times with 5 ml aliquots of ice-cold buffer. Specific binding was defined as the total radioligand bound minus that bound in the presence of 1000 nM SS-14 for SSTR 1, 3, 4, and 5, or 1000 nM MK-678 for SSTR2.

Dopamine Receptor Specificity and Selectivity Assay

Specificity and selectivity for the dopamine-2 receptor of the dopamine analogues used to synthesize the somatostatin-dopamine chimers may be determined by a radioligand binding assay as follows.

Crude membranes were prepared by homogenization of frozen rat corpus striatum (Zivic Laboratories, Pittsburgh, Pa.) in 20 ml of ice-cold 50 mM Tris-HCl with a BRINKMAN POLYTRON cell disrupter (setting 6, 15 sec). Buffer was added to obtain a final volume of 40 ml, and the homogenate was centrifuged in a SORVAL SS-34 rotor at 39,000 g for 10 minutes at 0-4° C. The resulting supernatant was decanted and discarded. The pellet was rehomogenized in ice-cold buffer, pre-incubated at 37° C. for 10 min, diluted, and centrifuged as before. The final pellet was resuspended in buffer and held on ice for the receptor binding assay.

For assay, aliquots of the washed membrane preparations and test compounds were incubated for 15 minutes (37° C.) with 0.25 nM $[^3H]$spiperone (16.5 Ci.mmol, New England Nuclear, Boston, Mass.) in 50 mM Tris HCl, 120 mM NaCl, 5 mM KCl, 2 mM $CaCl_2$, 1 mM $MgCl_2$. The final assay volume was 1.0 ml. The incubations were terminated by rapid filtration through GF/B glass fibre filters using a Brandel filtration manifold. Each tube and filter was then washed three times with 5-ml aliquots of ice-cold buffer. Specific binding was defined as the total radioligand bound minus that bound in the presence of 1000 nM (+) butaclamol.

Inhibition of cAMP Intracellular Production

The agonist activity of a somatostatin test compound is determined by the following assay.

CHO-K1 cells expressing human somatostatin (SRIF-14) subtype receptors are seeded in 24-well tissue culture plates in RPMI 1640 media with 10% fetal calf serum (FCS).

Cells at $10^5$ cells/well are washed 2 times by 0.5 ml RPMI 1640 media. Hank's balanced salt solution supplemented with 0.5 mM 3-isobutyl-1-methylxanthine ("IBMX"), and the cells are incubated for 30 minutes at 37° C. Cyclic AMP production is stimulated by the addition of 10 μM forskolin ("FSK") (Sigma Chemical Co., St. Louis, Mo.) for 30 minutes at 37° C.

The agonist effect of a compound is measured by the addition of the test compound ($10^{-10}$ M to $10^{-6}$ M) for five minutes prior to the addition of FSK (10 μM). The reaction is terminated by the addition of 500 ul of ice-cold absolute alcohol, and the supernatant is transferred to a 12×75 mm glass tube for cAMP determination. cAMP is measured using radioimmunoassay kit (Perkin-Elmer, Boston, Mass.).

OTHER EMBODIMENTS

Various modifications and variations of the described method and system of the invention will be apparent to those skilled in the art without departing from the scope and spirit of the invention. Although the invention has been described in connection with specific desired embodiments, it should be understood that the invention as claimed should not be unduly limited to such specific embodiments. Indeed, various modifications of the described modes for carrying out the invention that are obvious to those skilled in the fields of medicine, immunology, pharmacology, endocrinology, or related fields are intended to be within the scope of the invention.

All publications mentioned in this specification, including PCT/US02/17859, are herein incorporated by reference to the same extent as if the disclosure of each independent publication was explicitly provided herein.

What is claimed is:

1. A chimeric analog: Dop2-DLys(Dop2)-cyclo[Cys-Tyr-DTrp-Lys-Abu-Cys]-Thr-NH$_2$, or a pharmaceutically acceptable salt thereof.

2. A method of eliciting a dopamine receptor agonist effect in a subject in need thereof, comprising administering an effective amount of the chimeric analog of claim 1 to a subject in need thereof.

* * * * *